(12) United States Patent
Savelieva

(10) Patent No.: US 12,128,112 B2
(45) Date of Patent: *Oct. 29, 2024

(54) GENE THERAPY DNA VECTORS BASED ON VTVAF17

(71) Applicants: OBSCHESTVO S OGRANICHENNOI OTVETSTVENNOSTJU "PRORYVNYE INNOVATSIONNYE TEKHNOLOGII", Moscow (RU); CELL AND GENE THERAPY LTD, London (GB)

(72) Inventor: Natalia Savelieva, Wienna (AT)

(73) Assignees: OOO "PRORYVNYE INNOVATSIONNYE TEKHNOLOGII", Moscow (RU); CELL AND GENE THERAPY LTD, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 17/272,587

(22) PCT Filed: Aug. 14, 2019

(86) PCT No.: PCT/RU2019/000575
§ 371 (c)(1),
(2) Date: Mar. 1, 2021

(87) PCT Pub. No.: WO2020/050743
PCT Pub. Date: Mar. 12, 2020

(65) Prior Publication Data
US 2021/0308282 A1    Oct. 7, 2021

(30) Foreign Application Priority Data
Sep. 5, 2018 (RU) .......................... RU2018131844

(51) Int. Cl.
*A61K 48/00* (2006.01)
*C12N 1/20* (2006.01)
*C12N 15/10* (2006.01)
*C12N 15/70* (2006.01)
*C12N 15/85* (2006.01)

(52) U.S. Cl.
CPC ........ *A61K 48/005* (2013.01); *A61K 48/0016* (2013.01); *C12N 1/205* (2021.05); *C12N 15/1003* (2013.01); *C12N 15/70* (2013.01); *C12N 15/85* (2013.01)

(58) Field of Classification Search
CPC .. A61K 48/005; A61K 48/0016; C12N 1/205; C12N 15/1003; C12N 15/70; C12N 15/85; C12N 2810/85; C07K 14/4702
See application file for complete search history.

(56) References Cited

U.S. PATENT DOCUMENTS

| | | | |
|---|---|---|---|
| 9,550,998 B2 | 1/2017 | Williams | |
| 9,644,211 B2 | 5/2017 | Mayrhofer | |
| 11,149,279 B2 * | 10/2021 | Savelieva | ............... C12N 9/14 |
| 2015/0191735 A1 * | 7/2015 | Williams | ............... C12N 15/70 |
| | | | 435/69.3 |
| 2021/0310021 A1 * | 10/2021 | Savelieva | ............. C12N 15/70 |

FOREIGN PATENT DOCUMENTS

| | | |
|---|---|---|
| RU | 2011110736 A | 9/2012 |
| RU | 2548809 C2 | 4/2015 |
| RU | 2015140941 A | 3/2017 |
| RU | 2658428 C9 | 6/2018 |

* cited by examiner

*Primary Examiner* — Jeremy C Flinders
*Assistant Examiner* — Alexander W Nicol
(74) *Attorney, Agent, or Firm* — Nadya Reingand

(57) ABSTRACT

Produced the gene therapy DNA vectors based on the gene therapy DNA vector VTvaf17 for the treatment of diseases featuring disruption of mucociliary transport, mucolytic function and development of mucostasis. The gene therapy DNA vector contains the coding region of the SKI, TGFB3, TIMP2 or FMOD therapeutic genes. Methods of producing or use a gene therapy DNA vector based on gene therapy DNA vector VTvaf17 carrying SKI, TGFB3, TIMP2 or FMOD therapeutic genes. The methods of producing strain for production of gene therapy DNA vector for treatment of diseases featuring disruption of mucociliary transport and development of mucostasis. Escherichia coli strain SCS 110-AF/VTvaf17-SKI, SCS 110-AF/VTvaf17-TGFB3, SCS110-AF/VTvaf17-TIMP2 or SCSI 10-AF/VTvaf17-FMOD obtains by the method described above carrying gene therapy DNA vector VTvaf17-SKI, VTvaf17-TGFB3, VTvaf17-TIMP2 or VTvaf17-FMOD. The method of producing a gene therapy DNA vector carrying SKI, TGFB3, TIMP2 or FMOD therapeutic gene uses on an industrial scale.

4 Claims, 19 Drawing Sheets
Specification includes a Sequence Listing.

SEQUENCE LISTING

<160> NUMBER OF SEQ ID NOS: 20

<210> SEQ ID NO 1
<211> LENGTH: 5369
<212> TYPE: DNA
<213> ORGANISM: Homo Sapiens

<400> SEQUENCE: 1

```
cgtgaggctc cggtgcccgt cagtgggcag agcgcacatc gcccacagtc cccgagaagt      60
tggggggagg ggtcggcaat tgaaccggtg cctagagaaa gtggcgcggg gtaaactggg     120
aaagtgatgt cgtgtactgg ctccgccttt ttcccgaggg tgggggagaa ccgtatataa     180
gtgcagtagt cgccgtgaac gttctttttc gcaacgggtt tgccgccaga acacaggtaa     240
gtgccgtgtg tggttcccgc gggcctggcc tctttacggg ttatggccct tgcgtgcctt     300
gaattacttc cacgccctg gctgcagtac gtgattcttg atcccgagct tcgggttgga     360
agtgggtggg agagttcgag gccttgcgct taaggagccc cttcgcctcg tgcttgagtt     420
gaggcctggc ttgggcgctg gggccgccgc gtgcgaatct ggtggcacct tcgcgcctgt     480
ctcgctgctt tcgataagtc tctagccatt taaaattttt gatgacctgc tgcgacgctt     540
tttttctggc aagatagtct tgtaaatgcg ggccaagatc tgcacactgg tatttcggtt     600
tttgggcccg cgggcggcga cggggcccgt gcgtcccagc gcacatgttc ggcgaggcgg     660
ggcctgcgag cgcggccacc gagaatcgga cgggggtagt ctcaagctgg ccggcctgct     720
ctggtgcctg gcctcgcgcc gccgtgtatc gccccgccct gggcggcaag gctggcccgg     780
tcggcaccag ttgcgtgagc ggaaagatgg ccgcttcccg gccctgctgc agggagctca     840
aaatggagga cgcggcgctc gggagagcgg gcgggtgagt cacccacaca aaggaaaagg     900
gcctttccgt cctcagccgt cgcttcatgt gactccacgg agtaccgggc gccgtccagg     960
cacctcgatt agttctcgag cttttggagt acgtcgtctt taggttgggg ggaggggttt    1020
tatgcgatgg agtttcccca cactgagtgg gtggagactg aagttaggcc agcttggcac    1080
ttgatgtaat tctccttgga atttgccctt tttgagtttg gatcttggtt cattctcaag    1140
cctcagacag tggttcaaag ttttttttctt ccatttcagg tgtcgtgaaa actacccta    1200
aaagccagga tccggtaccg aggagatctg ccgccgcgat cgccatggag gcggcggcag    1260
gcggccgcgg ctgtttccag ccgcacccgg ggctgcagaa gacgctggag cagttccacc    1320
tgagctccat gagctgctg gcggccccgg ccgctttctc ggcgcgctgg gcgcaggagg    1380
cctacaagaa ggagagcgcc aaggaggcgg gcgcggccgc ggtgccggcg ccggtgcccg    1440
cagccaccga gccgccgccc gtgctgcacc tgcccgccat ccagccgccg ccgccgtgc    1500
tgcccgggcc cttcttcatg ccgtccgacc gctccaccga gcgctgcgag accgtactgg    1560
aaggcgagac catctcgtgc ttcgtggtgg gaggcgagaa gcgcctgtgt ctgccgcaga    1620
ttctcaactc ggtgctgcgc gacttctcgc tgcagcagat caacgcggtg tgcgacgagc    1680
tccacatcta ctgctcgcgc tgcacggccg accagctgga gatcctcaaa gtcatgggca    1740
tcctgccctt ctcggcgccc tcgtgcgggc tcatcaccaa gacggacgcc gagcgcctgt    1800
```

```
gcaacgcgct gctctacggc ggcgcctacc cgccgccctg caagaaggag ctggccgcca   1860
gcctggcgct gggcctggag ctcagcgagc gcagcgtccg cgtgtaccac gagtgcttcg   1920
gcaagtgtaa ggggctgctg gtgcccgagc tctacagcag cccgagcgcc gcctgcatcc   1980
agtgcctgga ctgccgcctc atgtaccgc cgcacaagtt cgtggtgcac tcgcacaagg    2040
ccctggagaa ccggacctgc cactggggct tcgactcggc caactggcgg gcctacatcc   2100
tgctgagcca ggattacacg ggcaaggagg agcaggcgcg cctcggccgc tgcctggacg   2160
acgtgaagga gaaattcgac tatggcaaca agtacaagcg gcgggtgccc cgggtctcct   2220
ctgagcctcc ggcctccata agacccaaaa cagatgacac ctcttcccag tccccgcgc    2280
cttccgaaaa ggacaagccg tccagctggc tgcggacctt ggccggctct ccaataaga    2340
gcctgggctg tgttcaccct cgccagcgcc tctctgcttt ccgacctgg tccccgcag     2400
tgtcagcgag tgagaaagag ctctccccac acctcccggc cctcatccga cagcttct     2460
actcctacaa gagctttgag acagccgtgg cgcccaacgt ggcctcgca ccgccggccc    2520
agcagaaggt tgtgagcagc cctccgtgtg ccgccgccgt ctcccgggcc ccgagcctc    2580
tcgccacttg cacccagcct cggaagcgga agctgactgt ggacacccca ggagccccag   2640
agacgctggc gcccgtggct gccccagagg aggacaagga ctcggaggcg gaggtggaag   2700
ttgaaagcag ggaggaattc acctcctcct tgtcctcgct ctcttcccg tcctttacct    2760
catccagctc cgccaaggac ctgggctccc cgggtgcgcg tgccctgccc tcggccgtcc   2820
ctgatgctgc ggccctgcc gacgccccca gtgggctgga ggcggagctg gagcacctgc    2880
ggcaggcact ggagggcggc ctggacacca aggaagccaa agagaagttc ctgcatgagg   2940
tggtcaagat gcgcgtgaag caggaggaga agctcagcgc agccctgcag gccaagcgca   3000
gcctccacca ggagctggag ttcctacgcg tggccaagaa ggagaagctg cgggaggcca   3060
cggaggccaa gcgtaacctg cggaaggaga tcgagcgtct ccgcgccgag aacgagaaga   3120
agatgaaaga ggccaacgag tcacggctgc gcctgaagcg ggagctggag caggcgcggc   3180
aggcccgggt gtgcgacaag ggctgcgagg cgggccgcct gcgcgccaag tactcggccc   3240
agatcgaaga cctgcaggtg aagctgcagc acgcggaggc ggaccgggag cagctgcggg   3300
ccgacctgct gcgggagcgc gaggcccggg agcacctgga gaaggtggtg aaggagctgc   3360
aggaacagct gtgccgcgg gcccgccccg aggctgcggg cagcgagggc gctgcggagc    3420
tggagccgta agcttggtac cgaattccct gtgaccctc cccagtgcct ctcctggccc    3480
tggaagttgc cactccagtg cccaccagcc ttgtcctaat aaaattaagt tgcatcattt    3540
tgtctgacta ggtgtccttc tataatatta tggggtggag ggggtggta tggagcaagg    3600
ggcaagttgg gaagacaacc tgtagggcct gcggggtcta ttgggaacca agctggagtg   3660
cagtggcaca atcttggctc actgcaatct ccgcctcctg ggttcaagcg attctcctgc   3720
ctcagcctcc cgagttgttg ggattccagg catgcatgac caggctcagc taattttgt    3780
ttttttggta gagacggggt ttcaccatat tggccaggct ggtctccaac tcctaatctc   3840
aggtgatcta cccaccttgg cctcccaaat tgctgggatt acaggcgtga accactgctc   3900
ccttccctgt cctacgcgt agaattggta aagagagtcg tgtaaaatat cgagttcgca    3960
catcttgttg tctgattatt gattttggc gaaaccattt gatcatatga caagatgtgt    4020
atctacctta acttaatgat tttgataaaa atcattaact agtccatggc tgcctcgcgc   4080
gtttcggtga tgacggtgaa aacctctgac acatgcagct cccggagacg gtcacagctt   4140
gtctgtaagc ggatgccggg agcagacaag cccgtcaggg cgcgtcagcg ggtgttggcg   4200
```

-continued

```
ggtgtcgggg cgcagccatg acccagtcac gtagcgatag cggagtgtat actggcttaa    4260
ctatgcggca tcagagcaga ttgtactgag agtgcaccat atgcggtgtg aaataccgca    4320
cagatgcgta aggagaaaat accgcatcag gcgctcttcc gcttcctcgc tcactgactc    4380
gctgcgctcg gtcgttcggc tgcggcgagc ggtatcagct cactcaaagg cggtaatacg    4440
gttatccaca gaatcagggg ataacgcagg aaagaacatg tgagcaaaag gccagcaaaa    4500
ggccaggaac cgtaaaaagg ccgcgttgct ggcgtttttc cataggctcc gcccccctga    4560
cgagcatcac aaaaatcgac gctcaagtca gaggtggcga aacccgacag gactataaag    4620
ataccaggcg tttccccctg gaagctccct cgtgcgctct cctgttccga ccctgccgct    4680
taccggatac ctgtccgcct ttctcccttc gggaagcgtg gcgctttctc atagctcacg    4740
ctgtaggtat ctcagttcgg tgtaggtcgt tcgctccaag ctgggctgtg tgcacgaacc    4800
ccccgttcag cccgaccgct gcgccttatc cggtaactat cgtcttgagt ccaacccggt    4860
aagacacgac ttatcgccac tggcagcagc cactggtaac aggattagca gagcgaggta    4920
tgtaggcggt gctacagagt tcttgaagtg gtggcctaac tacggctaca ctagaagaac    4980
agtatttggt atctgcgctc tgctgaagcc agttaccttc ggaaaaagag ttggtagctc    5040
ttgatccggc aaacaaacca ccgctggtag cggtggtttt tttgtttgca agcagcagat    5100
tacgcgcaga aaaaaggat ctcaagaaga tcctttgatc ttttctacgg ggtctgacgc    5160
tcagtggaac gaaaactcac gttaagggat tttggtcatg agattatcaa aaaggatctt    5220
cacctagatc cttttaaatt aaaaatgaag ttttaaatca atctaaagta tatatgagta    5280
aacttggtct gacagttacc aatgcttaat cagtgaggca cctatctcag cgatctgtct    5340
atttcgttca tccatagttg cctgactcc                                      5369
```

<210> SEQ ID NO 2
<211> LENGTH: 4393
<212> TYPE: DNA
<213> ORGANISM: Homo Sapiens

<400> SEQUENCE: 2

```
cgtgaggctc cggtgcccgt cagtgggcag agcgcacatc gcccacagtc cccgagaagt      60 tgggggagg ggtcggcaat tgaaccggtg cctagagaaa gtggcgcggg gtaaactggg     120
aaagtgatgt cgtgtactgg ctccgccttt ttcccgaggg tggggagaa ccgtatataa     180 gtgcagtagt cgccgtgaac gttctttttc gcaacgggtt tgccgccaga acacaggtaa     240
gtgccgtgtg tggttcccgc gggcctggcc tctttacggg ttatggccct tgcgtgcctt     300
gaattacttc cacgcccctg gctgcagtac gtgattcttg atcccgagct tcgggttgga     360
agtgggtggg agagttcgag gccttgcgct taaggagccc cttcgcctcg tgcttgagtt     420
gaggcctggc ttgggcgctg gggccgccgc gtgcgaatct ggtggcacct tcgcgcctgt     480
ctcgctgctt tcgataagtc tctagccatt taaaatttt gatgacctgc tgcgacgctt     540
tttttctggc aagatagtct tgtaaatgcg gccaagatc tgcacactgg tatttcggtt     600
tttggggccg cgggcggcga cggggcccgt gcgtcccagc gcacatgttc ggcgaggcgg     660
ggcctgcgag cgcggccacc gagaatcgga cgggggtagt ctcaagctgg ccggcctgct     720
ctggtgcctg gctcgcgcc gccgtgtatc gccccgccct gggcggcaag gctggcccgg     780
tcggcaccag ttgcgtgagc ggaaagatgg ccgcttcccg gccctgctgc agggagctca     840
aaatggagga cgcggcgctc gggagagcgg gcgggtgagt cacccacaca aaggaaaagg     900
```

```
gcctttccgt cctcagccgt cgcttcatgt gactccacgg agtaccgggc gccgtccagg    960
cacctcgatt agttctcgag cttttggagt acgtcgtctt taggttgggg ggagggggttt   1020
tatgcgatgg agtttcccca cactgagtgg gtggagactg aagttaggcc agcttggcac    1080
ttgatgtaat tctccttgga atttgccctt tttgagtttg gatcttggtt cattctcaag    1140
cctcagacag tggttcaaag ttttttttctt ccatttcagg tgtcgtgaaa actacccta    1200
aaagccagga tccaccatga agatgcactt gcaaagggct ctggtggtcc tggccctgct    1260
gaactttgcc acggtcagcc tctctctgtc cacttgcacc accttggact tcggccacat    1320
caagaagaag agggtggaag ccattagggg acagatcttg agcaagctca ggctcaccag    1380
ccccccctgag ccaacggtga tgacccacgt ccctatcag gtcctggccc tttacaacag    1440
cacccgggga ctgctggagg agatgcatgg ggagagggag gaaggctgca cccaggaaaa    1500
caccgagtcg gaatactatg ccaaagaaat ccataaattc gacatgatcc aggggctggc    1560
ggagcacaac gaactggctg tctgtcctaa aggaattacc tccaaggttt tccgcttcaa    1620
tgtgtcctca gtggagaaaa atagaaccaa cctattccga gcagaattcc gggtcttgcg    1680
ggtgcccaac cccagctcta agcggaatga gcagaggatc gagctcttcc agatccttcg    1740
gccagatgag cacattgcca acagcgcta tatcggtggc aagaatctgc ccacacgggg    1800
cactgccgag tggctgtcct ttgatgtcac tgacactgtg cgtgagtggc tgttgagaag    1860
agagtccaac ttaggtctag aaatcagcat tcactgtcca tgtcacacct ttcagcccaa    1920
tggagatatc ctggaaaaca ttcacgaggt gatggaaatc aaattcaaag gcgtggacaa    1980
tgaggatgac catggccgtg gagatctggg gcgcctcaag aagcagaagg atcaccacaa    2040
ccctcatcta atcctcatga tgattccccc acaccggctc gacaacccgg gccagggggg    2100
tcagaggaag aagcgggctt tggacaccaa ttactgcttc gcaacttgg aggagaactg     2160
ctgtgtgcgc ccctctaca ttgacttccg acaggatctg ggctggaagt gggtccatga     2220
acctaagggc tactatgcca acttctgctc aggcccttgc ccatacctcc gcagtgcaga    2280
cacaacccac agcacggtgc tgggactgta caacactctg aaccctgaag catctgcctc    2340
gccttgctgc gtgccccagg acctggagcc cctgaccatc ctgtactatg ttgggaggac    2400
ccccaaagtg gagcagctct ccaacatggt ggtgaagtct tgtaaatgta gctaagcttg    2460
gtaccgaatt ccctgtgacc cctcccagt gcctctcctg gccctggaag ttgccactcc     2520
agtgcccacc agccttgtcc taataaaatt aagttgcatc attttgtctg actaggtgtc    2580
cttctataat attatggggt ggagggggt ggtatggagc aaggggcaag ttgggaagac      2640
aacctgtagg gcctgcgggg tctattggga accaagctgg agtgcagtgg cacaatcttg    2700
gctcactgca atctccgcct cctgggttca agcgattctc ctgcctcagc ctcccgagtt    2760
gttgggattc caggcatgca tgaccaggct cagctaattt ttgtttttt ggtagagacg     2820
gggtttcacc atattggcca ggctggtctc caactcctaa tctcaggtga tctacccacc    2880
ttggcctccc aaattgctgg gattacaggc gtgaaccact gctcccttcc ctgtccttac    2940
gcgtagaatt ggtaaagaga gtcgtgtaaa atatcgagtt cgcacatctt gttgtctgat    3000
tattgatttt tggcgaaacc atttgatcat atgacaagat gtgtatctac cttaacttaa    3060
tgatttgat aaaaatcatt aactagtcca tggctgcctc gcgcgtttcg gtgatgacgg      3120
tgaaaacctc tgacacatgc agctcccgga cggtcaca gcttgtctgt aagcggatgc       3180
cgggagcaga caagcccgtc agggcgcgtc agcgggtgtt ggcgggtgtc ggggcgcagc    3240
catgacccag tcacgtagcg atagcggagt gtatactggc ttaactatgc ggcatcagag    3300
```

```
cagattgtac tgagagtgca ccatatgcgg tgtgaaatac cgcacagatg cgtaaggaga      3360
aaataccgca tcaggcgctc ttccgcttcc tcgctcactg actcgctgcg ctcggtcgtt      3420
cggctgcggc gagcggtatc agctcactca aaggcggtaa tacggttatc cacagaatca      3480
ggggataacg caggaaagaa catgtgagca aaaggccagc aaaaggccag gaaccgtaaa      3540
aaggccgcgt tgctggcgtt tttccatagg ctccgccccc ctgacgagca tcacaaaaat      3600
cgacgctcaa gtcagaggtg gcgaaacccg acaggactat aaagatacca ggcgtttccc      3660
cctggaagct ccctcgtgcg ctctcctgtt ccgaccctgc cgcttaccgg atacctgtcc      3720
gcctttctcc cttcgggaag cgtggcgctt tctcatagct cacgctgtag gtatctcagt      3780
tcggtgtagg tcgttcgctc caagctgggc tgtgtgcacg aaccccccgt tcagcccgac      3840
cgctgcgcct tatccggtaa ctatcgtctt gagtccaacc cggtaagaca cgacttatcg      3900
ccactggcag cagccactgg taacaggatt agcagagcga ggtatgtagg cggtgctaca      3960
gagttcttga agtggtggcc taactacggc tacactagaa gaacagtatt tggtatctgc      4020
gctctgctga agccagttac cttcggaaaa agagttggta gctcttgatc cggcaaacaa      4080
accaccgctg gtagcggtgg tttttttgtt tgcaagcagc agattacgcg cagaaaaaaa      4140
ggatctcaag aagatccttt gatcttttct acggggtctg acgctcagtg gaacgaaaac      4200
tcacgttaag ggattttggt catgagatta tcaaaaagga tcttcaccta gatccttta      4260 aattaaaaat gaagttttaa atcaatctaa agtatatatg agtaaacttg gtctgacagt      4320
taccaatgct taatcagtga ggcacctatc tcagcgatct gtctatttcg ttcatccata      4380
gttgcctgac tcc                                                        4393

<210> SEQ ID NO 3
<211> LENGTH: 3845
<212> TYPE: DNA
<213> ORGANISM: Homo Sapiens

<400> SEQUENCE: 3
cgtgaggctc cggtgcccgt cagtgggcag agcgcacatc gcccacagtc cccgagaagt        60
tggggggagg ggtcggcaat tgaaccggtg cctagagaaa gtggcgcggg gtaaactggg       120
aaagtgatgt cgtgtactgg ctccgccttt ttcccgaggg tgggggagaa ccgtatataa       180
gtgcagtagt cgccgtgaac gttcttttc gcaacgggtt tgccgccaga acacaggtaa       240
gtgccgtgtg tggttcccgc gggcctggcc tctttacggg ttatggccct tgcgtgcctt       300
gaattacttc cacgccctg gctgcagtac gtgattcttg atcccgagct tcgggttgga       360
agtgggtggg agagttcgag gccttgcgct taaggagccc cttcgcctcg tgcttgagtt       420
gaggcctggc ttgggcgctg gggccgccgc gtgcgaatct ggtggcacct tcgcgcctgt       480
ctcgctgctt tcgataagtc tctagccatt taaaattttt gatgacctgc tgcgacgctt       540
tttttctggc aagatagtct tgtaaatgcg ggccaagatc tgcacactgg tatttcggtt       600 tttgggccg cgggcggcga cggggcccgt gcgtcccagc gcacatgttc ggcgaggcgg       660
ggcctgcgag cgcggccacc gagaatcgga cgggggtagt ctcaagctgg ccggcctgct       720
ctggtgcctg gcctcgcgcc gccgtgtatc gccccgccct gggcggcaag gctggcccgg       780
tcggcaccag ttgcgtgagc ggaaagatgg ccgcttcccg gccctgctgc agggagctca       840
aaatggagga cgcggcgctc gggagagcgg gcgggtgagt cacccacaca aaggaaaagg       900
gcctttccgt cctcagccgt cgcttcatgt gactccacgg agtaccgggc gccgtccagg       960
```

-continued

```
cacctcgatt agttctcgag cttttggagt acgtcgtctt taggttgggg ggaggggttt    1020
tatgcgatgg agtttcccca cactgagtgg gtggagactg aagttaggcc agcttggcac    1080
ttgatgtaat tctccttgga atttgccctt tttgagtttg gatcttggtt cattctcaag    1140
cctcagacag tggttcaaag ttttttttctt ccatttcagg tgtcgtgaaa actacccta    1200 aaagccagga tccggtaccg aggagatctg ccgccgcgat cgccatgggc gccgcggccc    1260
gcaccctgcg gctggcgctc ggcctcctgc tgctggcgac gctgcttcgc ccggccgacg    1320
cctgcagctg ctccccggtg cacccgcaac aggcgttttg caatgcagat gtagtgatca    1380
gggccaaagc ggtcagtgag aaggaagtgg actctggaaa cgacatttat ggcaacccta    1440
tcaagaggat ccagtatgag atcaagcaga taaagatgtt caaagggcct gagaaggata    1500
tagagtttat ctacacggcc ccctcctcgg cagtgtgtgg ggtctcgctg gacgttggag    1560
gaaagaagga atatctcatt gcaggaaagg ccgaggggga cggcaagatg cacatcaccc    1620
tctgtgactt catcgtgccc tgggacaccc tgagcaccac ccagaagaag agcctgaacc    1680
acaggtacca gatgggctgc gagtgcaaga tcacgcgctg ccccatgatc ccgtgctaca    1740
tctcctcccc ggacgagtgc ctctggatgg actgggtcac agagaagaac atcaacgggc    1800
accaggccaa gttcttcgcc tgcatcaaga aagtgacgg ctcctgtgcg tggtaccgcg    1860
gcgcggcgcc ccccaagcag gagtttctcg acatcgagga cccataagct tggtaccgaa    1920
ttccctgtga cccctcccca gtgcctctcc tggccctgga agttgccact ccagtgccca    1980
ccagccttgt cctaataaaa ttaagttgca tcattttgtc tgactaggtg tccttctata    2040
atattatggg gtggaggggg gtggtatgga gcaaggggca agttgggaag acaacctgta    2100
gggcctgcgg ggtctattgg gaaccaagct ggagtgcagt ggcacaatct ggctcactg    2160 caatctccgc tcctgggtt caagcgattc tcctgcctca gcctcccgag ttgttgggat    2220
tccaggcatg catgaccagg ctcagctaat ttttgttttt ttggtagaga cggggtttca    2280
ccatattggc caggctggtc tccaactcct aatctcaggt gatctaccca ccttggcctc    2340
ccaaattgct gggattacag gcgtgaacca ctgctccctt ccctgtcctt acgcgtagaa    2400
ttggtaaaga gagtcgtgta aaatatcgag ttcgcacatc ttgttgtctg attattgatt    2460
tttggcgaaa ccatttgatc atatgacaag atgtgtatct accttaactt aatgattttg    2520
ataaaaatca ttaactagtc catggctgcc tcgcgcgttt cggtgatgac ggtgaaaacc    2580
tctgacacat gcagctcccg gagacggtca cagcttgtct gtaagcggat gccgggagca    2640
gacaagcccg tcagggcgcg tcagcgggtg ttggcgggtg tcggggcgca gccatgaccc    2700
agtcacgtag cgatagcgga gtgtatactg gcttaactat gcggcatcag agcagattgt    2760
actgagagtg caccatatgc ggtgtgaaat accgcacaga tgcgtaagga gaaaataccg    2820
catcaggcgc tcttccgctt cctcgctcac tgactcgctg cgctcggtcg ttcggctgcg    2880
gcgagcggta tcagctcact caaaggcggt aatacggtta ccacagaat caggggataa    2940 cgcaggaaag aacatgtgag caaaaggcca gcaaaaggcc aggaaccgta aaaaggccgc    3000
gttgctggcg ttttttccata ggctccgccc cctgacgag catcacaaaa atcgacgctc    3060
aagtcagagg tggcgaaacc cgacaggact ataaagatac caggcgtttc ccctggaag    3120 ctccctcgtg cgctctcctg ttccgaccct gccgcttacc ggatacctgt ccgcctttct    3180
cccttcggga agcgtggcgc tttctcatag ctcacgctgt aggtatctca gttcggtgta    3240
ggtcgttcgc tccaagctgg gctgtgtgca cgaaccccc gttcagcccg accgctgcgc    3300
cttatccggt aactatcgtc ttgagtccaa cccggtaaga cacgacttat cgccactggc    3360
```

-continued

| | |
|---|---|
| agcagccact ggtaacagga ttagcagagc gaggtatgta ggcggtgcta cagagttctt | 3420 |
| gaagtggtgg cctaactacg gctacactag aagaacagta tttggtatct gcgctctgct | 3480 |
| gaagccagtt accttcggaa aaagagttgg tagctcttga tccggcaaac aaaccaccgc | 3540 |
| tggtagcggt ggtttttttg tttgcaagca gcagattacg cgcagaaaaa aaggatctca | 3600 |
| agaagatcct ttgatctttt ctacggggtc tgacgctcag tggaacgaaa actcacgtta | 3660 |
| agggattttg gtcatgagat tatcaaaaag gatcttcacc tagatccttt taaattaaaa | 3720 |
| atgaagtttt aaatcaatct aaagtatata tgagtaaact tggtctgaca gttaccaatg | 3780 |
| cttaatcagt gaggcaccta tctcagcgat ctgtctattt cgttcatcca tagttgcctg | 3840 |
| actcc | 3845 |

<210> SEQ ID NO 4
<211> LENGTH: 4275
<212> TYPE: DNA
<213> ORGANISM: Homo Sapiens

<400> SEQUENCE: 4

| | |
|---|---|
| cgtgaggctc cggtgcccgt cagtgggcag agcgcacatc gcccacagtc cccgagaagt | 60 |
| tgggggagg ggtcggcaat tgaaccggtg cctagagaaa gtggcgcggg gtaaactggg | 120 |
| aaagtgatgt cgtgtactgg ctccgccttt tccccgaggg tgggggagaa ccgtatataa | 180 |
| gtgcagtagt cgccgtgaac gttctttttc gcaacgggtt tgccgccaga acacaggtaa | 240 |
| gtgccgtgtg tggttcccgc gggcctggcc tctttacggg ttatggccct tgcgtgcctt | 300 |
| gaattacttc cacgcccctg gctgcagtac gtgattcttg atcccgagct cgggttgga | 360 |
| agtgggtggg agagttcgag gccttgcgct taaggagccc cttcgcctcg tgcttgagtt | 420 |
| gaggcctggc ttgggcgctg gggccgccgc gtgcgaatct ggtggcacct tcgcgcctgt | 480 |
| ctcgctgctt tcgataagtc tctagccatt taaaatttt gatgacctgc tgcgacgctt | 540 |
| ttttttctggc aagatagtct tgtaaatgcg ggccaagatc tgcacactgg tatttcggtt | 600 |
| tttgggggccg cgggcggcga cggggcccgt gcgtcccagc gcacatgttc ggcgaggcgg | 660 |
| ggcctgcgag cgcggccacc gagaatcgga cgggggtagt ctcaagctgg ccggcctgct | 720 |
| ctggtgcctg gcctcgcgcc gccgtgtatc gccccgccct gggcggcaag gctggcccgg | 780 |
| tcggcaccag ttgcgtgagc ggaaagatgg ccgcttcccg gccctgctgc agggagctca | 840 |
| aaatggagga cgcggcgctc gggagagcgg gcgggtgagt cacccacaca aaggaaaagg | 900 |
| gccttttccgt cctcagccgt cgcttcatgt gactccacgg agtaccgggc gccgtccagg | 960 |
| cacctcgatt agttctcgag cttttggagt acgtcgtctt taggttgggg ggaggggttt | 1020 |
| tatgcgatgg agtttcccca cactgagtgg gtggagactg aagttaggcc agcttggcac | 1080 |
| ttgatgtaat tctccttgga atttgccctt tttgagtttg gatcttggtt cattctcaag | 1140 |
| cctcagacag tggttcaaag ttttttttctt ccatttcagg tgtcgtgaaa actacccta | 1200 |
| aaagccagga tccaccatgc agtggacctc cctcctgctg ctggcagggc tcttctccct | 1260 |
| ctcccaggcc cagtatgaag atgaccctca ttggtggttc cactacctcc gcagccagca | 1320 |
| gtccacctac tacgatccct atgaccctta cccgtatgag acctacgagc ttacccccta | 1380 |
| tggggtggat gaagggccag cctacaccta cggctctcca tcccctccag atccccgcga | 1440 |
| ctgcccccag gagtgcgact gcccacccaa cttccccacg gccatgtact gtgacaatcg | 1500 |
| caacctcaag tacctgccct tcgttccctc ccgcatgaag tatgtgtact tccagaacaa | 1560 |

```
ccagatcacc tccatccagg aaggcgtctt tgacaatgcc acagggctgc tctggattgc    1620
tctccacggc aaccagatca ccagtgataa ggtgggcagg aaggtcttct ccaagctgag    1680
gcacctggag aggctgtacc tggaccacaa caacctgacc cggatgcccg gtcccctgcc    1740
tcgatccctg agagagctcc atctcgacca caaccagatc tcacgggtcc caacaatgc     1800 tctggagggg ctggagaacc tcacggcctt gtacctccaa cacaatgaga tccaggaagt    1860
gggcagttcc atgaggggcc tccggtcact gatcttgctg gacctgagtt ataaccacct    1920
tcggaaggtg cctgatgggc tgccctcagc tcttgagcag ctgtacatgg agcacaacaa    1980
tgtctacacc gtccccgata gctacttccg ggggcgccc aagctgctgt atgtgcggct     2040
gtcccacaac agtctaacca acaatggcct ggcctccaac accttcaatt ccagcagcct    2100
ccttgagcta gacctctcct acaaccagct gcagaagatc cccccagtca acaccaacct    2160
ggagaacctc tacctccaag gcaataggat caatgagttc tccatcagca gcttctgcac    2220
cgtggtggac gtcgtgaact ctccaagct gcaggtgctg cgcctggacg ggaacgagat      2280
caagcgcagc gccatgcctg ccgacgcgcc cctctgcctg cgccttgcca gcctcatcga    2340
gatctaagaa ttccctgtga cccctcccca gtgcctctcc tggccctgga agttgccact    2400
ccagtgccca ccagccttgt cctaataaaa ttaagttgca tcattttgtc tgactaggtg    2460
tccttctata atattatggg gtggagggg gtggtatgga gcaaggggca agttgggaag      2520
acaacctgta gggcctgcgg ggtctattgg gaaccaagct ggagtgcagt ggcacaatct    2580
tggctcactg caatctccgc ctcctgggtt caagcgattc tcctgcctca gcctcccgag    2640
ttgttgggat tccaggcatg catgaccagg ctcagctaat ttttgttttt ttggtagaga    2700
cggggtttca ccatattggc caggctggtc tccaactcct aatctcaggt gatctaccca    2760
ccttggcctc ccaaattgct gggattacag gcgtgaacca ctgctccctt ccctgtcctt    2820
acgcgtagaa ttggtaaaga gagtcgtgta aaatatcgag ttcgcacatc ttgttgtctg    2880
attattgatt tttggcgaaa ccatttgatc atatgacaag atgtgtatct accttaactt    2940
aatgattttg ataaaaatca ttaactagtc catggctgcc tcgcgcgttt cggtgatgac    3000
ggtgaaaacc tctgacacat gcagctcccg gagacggtca cagcttgtct gtaagcggat    3060
gccgggagca gacaagcccg tcagggcgcg tcagcgggtg ttggcgggtg tcggggcgca    3120
gccatgaccc agtcacgtag cgatagcgga gtgtatactg gcttaactat gcggcatcag    3180
agcagattgt actgagagtg caccatatgc ggtgtgaaat accgcacaga tgcgtaagga    3240
gaaaataccg catcaggcgc tcttccgctt cctcgctcac tgactcgctg cgctcggtcg    3300
ttcggctgcg gcgagcggta tcagctcact caaaggcggt aatacggtta ccacagaat     3360 cagggggataa cgcaggaaag aacatgtgag caaaaggcca gcaaaaggcc aggaaccgta    3420
aaaaggccgc gttgctggcg ttttcccata ggctccgccc cctgacgag catcacaaaa     3480 atcgacgctc aagtcagagg tggcgaaacc cgacaggact ataaagatac caggcgtttc    3540
cccctggaag ctccctcgtg cgctctcctg ttccgaccct gccgcttacc ggatacctgt    3600
ccgcctttct cccttcggga agcgtggcgc tttctcatag ctcacgctgt aggtatctca    3660
gttcggtgta ggtcgttcgc tccaagctgg gctgtgtgca cgaaccccc gttcagcccg     3720 accgctgcgc cttatccggt aactatcgtc ttgagtccaa cccggtaaga cacgacttat    3780
cgccactggc agcagccact ggtaacagga ttagcagagc gaggtatgta ggcggtgcta    3840
cagagttctt gaagtggtgg cctaactacg gctacactag aagaacagta tttggtatct    3900
gcgctctgct gaagccagtt accttcggaa aaagagttgg tagctcttga tccggcaaac    3960
```

```
aaaccaccgc tggtagcggt ggttttttg  tttgcaagca gcagattacg cgcagaaaaa    4020
aaggatctca agaagatcct tgatctttt  ctacggggtc tgacgctcag tggaacgaaa    4080
actcacgtta agggattttg gtcatgagat tatcaaaaag gatcttcacc tagatccttt    4140
taaattaaaa atgaagtttt aaatcaatct aaagtatata tgagtaaact tggtctgaca    4200
gttaccaatg cttaatcagt gaggcaccta tctcagcgat ctgtctattt cgttcatcca    4260
tagttgcctg actcc                                                    4275
```

```
<210> SEQ ID NO 5
<211> LENGTH: 27
<212> TYPE: DNA
<213> ORGANISM: Artificial Sequence
<220> FEATURE:
<223> OTHER INFORMATION: Oligonucleotide SKI_F

<400> SEQUENCE: 5
caggatccgc gggagcggcc gggggag                                         27

<210> SEQ ID NO 6
<211> LENGTH: 27
<212> TYPE: DNA
<213> ORGANISM: Artificial Sequence
<220> FEATURE:
<223> OTHER INFORMATION: Oligonucleotide SKI_R

<400> SEQUENCE: 6
tataagctta cggctccagc tccgcag                                         27

<210> SEQ ID NO 7
<211> LENGTH: 21
<212> TYPE: DNA
<213> ORGANISM: Artificial Sequence
<220> FEATURE:
<223> OTHER INFORMATION: Oligonucleotide SKI_SF

<400> SEQUENCE: 7
tggacaccaa ggaagccaaa g                                               21

<210> SEQ ID NO 8
<211> LENGTH: 22
<212> TYPE: DNA
<213> ORGANISM: Artificial Sequence
<220> FEATURE:
<223> OTHER INFORMATION: Oligonucleotide SKI_SR

<400> SEQUENCE: 8
gctgttcctg cagctccttc ac                                              22

<210> SEQ ID NO 9
<211> LENGTH: 30
<212> TYPE: DNA
<213> ORGANISM: Artificial Sequence
<220> FEATURE:
<223> OTHER INFORMATION: Oligonucleotide TGFB3_F

<400> SEQUENCE: 9
ggatccacca tgaagatgca cttgcaaagg                                      30

<210> SEQ ID NO 10
<211> LENGTH: 33
<212> TYPE: DNA
<213> ORGANISM: Artificial Sequence
<220> FEATURE:
```

<223> OTHER INFORMATION: Oligonucleotide TGFB3_R

<400> SEQUENCE: 10
tataagctta gctacattta caagacttca cca                          33

<210> SEQ ID NO 11
<211> LENGTH: 20
<212> TYPE: DNA
<213> ORGANISM: Artificial Sequence
<220> FEATURE:
<223> OTHER INFORMATION: Oligonucleotide TGFB3_SF

<400> SEQUENCE: 11
tgagcacatt gccaaacagc                                         20

<210> SEQ ID NO 12
<211> LENGTH: 20
<212> TYPE: DNA
<213> ORGANISM: Artificial Sequence
<220> FEATURE:
<223> OTHER INFORMATION: Oligonucleotide TGFB3_SR

<400> SEQUENCE: 12
gaggcagatg cttcagggtt                                         20

<210> SEQ ID NO 13
<211> LENGTH: 26
<212> TYPE: DNA
<213> ORGANISM: Artificial Sequence
<220> FEATURE:
<223> OTHER INFORMATION: Oligonucleotide TIMP2_F

<400> SEQUENCE: 13
caggatccgg cccccgcccg cccagc                                  26

<210> SEQ ID NO 14
<211> LENGTH: 29
<212> TYPE: DNA
<213> ORGANISM: Artificial Sequence
<220> FEATURE:
<223> OTHER INFORMATION: Oligonucleotide TIMP2_R

<400> SEQUENCE: 14
tataagctta tgggtcctcg atgtcgaga                               29

<210> SEQ ID NO 15
<211> LENGTH: 20
<212> TYPE: DNA
<213> ORGANISM: Artificial Sequence
<220> FEATURE:
<223> OTHER INFORMATION: Oligonucleotide TIMP2_SF

<400> SEQUENCE: 15
gcaacaggcg ttttgcaatg                                         20

<210> SEQ ID NO 16
<211> LENGTH: 20
<212> TYPE: DNA
<213> ORGANISM: Artificial Sequence
<220> FEATURE:
<223> OTHER INFORMATION: Oligonucleotide TIMP2_SR

<400> SEQUENCE: 16
agggcacgat gaagtcacag                                         20

```
<210> SEQ ID NO 17
<211> LENGTH: 29
<212> TYPE: DNA
<213> ORGANISM: Artificial Sequence
<220> FEATURE:
<223> OTHER INFORMATION: Oligonucleotide FMOD_F

<400> SEQUENCE: 17
ggatccacca tgcagtggac ctccctcct                                      29

<210> SEQ ID NO 18
<211> LENGTH: 31
<212> TYPE: DNA
<213> ORGANISM: Artificial Sequence
<220> FEATURE:
<223> OTHER INFORMATION: Oligonucleotide FMOD_R

<400> SEQUENCE: 18
tatgaattct tagatctcga tgaggctggc a                                   31

<210> SEQ ID NO 19
<211> LENGTH: 20
<212> TYPE: DNA
<213> ORGANISM: Artificial Sequence
<220> FEATURE:
<223> OTHER INFORMATION: Oligonucleotide FMOD_SF

<400> SEQUENCE: 19
cctacaccta cggctctcca                                                20

<210> SEQ ID NO 20
<211> LENGTH: 20
<212> TYPE: DNA
<213> ORGANISM: Artificial Sequence
<220> FEATURE:
<223> OTHER INFORMATION: Oligonucleotide FMOD_SR

<400> SEQUENCE: 20
catccgggtc aggttgttgt                                                20
```

GENE THERAPY DNA VECTORS BASED ON VTVAF17

FIELD OF THE INVENTION

The invention refers to genetic engineering and can be used in biotechnology, medicine, and agriculture for the manufacture of gene therapy products. Thus, the produced gene therapy DNA vector containing the therapeutic gene can be used to deliver it to the cells of human beings and animals that experience reduced or insufficient expression of protein encoded by this gene, thus ensuring the desired therapeutic effect.

REFERENCE TO SEQUENCE LISTING

SEQ ID NO: 1 through SEQ ID NO: 20, incorporated fully by reference herein, are provided in ASCII format together in one separately enclosed .TXT file, submitted via EFS-Web—File name: U.S. Ser. No. 17/272,587.txt; Date of Creation: Jun. 14, 2021; File size: 26.46 KB.

BACKGROUND OF THE INVENTION

Gene therapy is an innovative approach in medicine aimed at treating inherited and acquired diseases by means of delivery of new genetic material into a patient's cells to compensate for or suppress the function of a mutant gene and/or treat a genetic disorder. The final product of gene expression may be an RNA molecule or a protein molecule. However, most physiological processes in the body are associated with the functional activity of protein molecules, while RNA molecules are either an intermediate product in the synthesis of proteins or perform regulatory functions. Thus, the objective of gene therapy in most cases is to inject the organism with genes that provide transcription and further translation of protein molecules encoded by these genes. Within the description of the invention, gene expression refers to the production of a protein molecule with amino acid sequence encoded by this gene.

SKI, TGFB3, FMOD, and TIMP2 genes included in the group of genes play a key role in several processes in human and animal organisms. These genes are involved in the TGF-beta (or TGFB) signalling cascade that is involved to one degree or another in most biological processes in the body. The correlations between low/insufficient concentrations of these proteins and different adverse human states in some cases confirmed by disturbances in normal gene expression encoding these proteins was demonstrated. Thus, the gene therapy increase of expression of a gene selected from the group of SKI, TGFB3, FMOD, and TIMP2 genes has potential to correct various conditions in humans and animals.

The SKI gene encodes a transcription protein-cofactor, in particular, it acts as a transcription corepressor and regulates the TGFB/Smad signalling cascade during embryogenesis and tissue homeostasis maintenance. Also, its coactivator role is shown in case of transcriptional factors of the NF1 family, as well as the MyoD transcription factor, the main function of which is the expression of genes involved in myogenesis. In addition to myogenesis, SKI is involved in the regulation of such processes as neurogenesis, haematopoiesis, fatty acid metabolism, apoptosis, and cell proliferation, as well as in the pathogenesis of various diseases. A number of adverse body states is accompanied by insufficient SKI expression. For example, SKI silencing is observed in hepatic fibrosis induced by ethyl alcohol metabolites. In systemic sclerosis, expression of the SKI protein is increased, but its functional activity is impaired. During tissue remodelling in treating liver disease, SKI suppresses a number of antiproliferative signals, whereas in the case of vascular regeneration, SKI inhibits cell proliferation. These observations indicate the versatile functions of SKI protein, depending on the conditions and contextual environment (Tecalco-Cruz et al. 2018).

Negative TGFB signalling cascade regulation by the SKI cofactor can potentially prevent tissue fibrosis. It is known that insufficient SKI expression is associated with kidney, lung, and liver fibrosis (Li X, et al. 2016; Tang H, et al. 2016; Chen J, et al. 2013; Tan R, et al. 2006). In experimental model of kidney fibrosis, it was shown that increased SKI expression prevents evolution of pathological changes associated with tissue fibrosis (Yang J, Zhang X, Li Y, Liu Y. 2003). Also, in case of wound injuries to the skin in animals with SKI protein overexpression obtained by injecting the DNA vector with SKI transgene, acceleration of wound healing and inhibition of scar formation at the site of damage was observed (Liu X, et al. 2006; Peng Y, et al. 2016). The increase in local SKI expression by introducing the plasmid vector expressing the SKI gene resulted in accelerated wound healing by stopping inflammation, accelerating re-epithelialisation and increasing the formation of granulation tissue. The reduction of scar formation due to the reduced collagen formation in the area of skin damage in rats was demonstrated (Li, P., et al.//J Pathol, 2011. 223(5): p. 659-71).

The role of SKI in carcinogenesis is poorly studied; there is evidence of both the pro-oncogenic and anti-oncogenic role of SKI. For example, in mice homozygous for one of the SKI gene mutations, an increased frequency of spontaneous lymphomas and susceptibility to carcinogens is observed (Shinagawa T, et al. 2001). The reduced SKI expression is observed in patients with certain types of dysplasia in the damage area compared to areas not affected by dysplasia (Villanacci V, et al. 2008). Some types of metastatic lung cancers feature reduced SKI expression (Yang H, et al. 2015), while increased SKI expression in breast cancer, on the contrary, potentiates the metastasis of tumour (Ritter M, et al. 2006).

Hereditary Shprintzen-Goldberg syndrome caused by a deletion mutation in the SKI gene and manifested by skeletal, neurological, cardiovascular, and other abnormalities is also described (Zhu X, et al. 2013).

The TGFB3 gene encodes the TGFB3 protein that constitutes a pleiotropic cytokine and one of the three isoforms of TGFB proteins involved in the signalling cascade of the same name. Together with other isoforms TGFB1 and TGFB2, TGFB3 plays a key role in the immune system and has both pro- and anti-inflammatory functions, participates in the regulation of antibody production and mucosal immunity. The association of TGFB3 mutations with a number of autoimmune diseases, for example, HLA-B7+spondyloarthropathies, is shown. It was also shown that mice with insufficient TGFB3 expression develop autoimmune disorders with lupus-like manifestations (Komai T et al. 2018).

Experimental study showed that mesenchymal stem cells overexpressing TGFB3 significantly improved wound healing in laboratory rabbits. This approach also allowed for changing the balance of different types of collagens, which contributed to the reduction of scar formation (Li M et al. 2018).

Another study showed that mesenchymal stem cells transduced with recombinant adenoviral vector expressing TGFB3 and recombinant adenoviral vector expressing BMP-2 promoted regeneration of damaged cartilage in the experimental pig model (Wang X et al. 2015).

A model of degenerative changes in vertebral discs in rabbits shows that the injection of a recombinant lentiviral vector expressing the survivin, TGFB3, and TIMP2 proteins, helps to slow the degenerative changes in the vertebral discs (Yue B et al. 2016).

Unlike other TGFB isoforms, TGFB3 has anti-fibrotic effect and inhibits the formation of scar tissue. Avotermin (Juvista®, Renovo; available in 2 forms—for intracutaneous injection and topical applications) that constitutes recombinant TGFB3 protein accelerated wound healing and helped preventing the formation of scars during phase I/II of clinical trials (McCollum P T et al. 2011).

Taking into account the short half-life of active TGFB3 protein form (2-3 minutes), the gene therapy approach is the most perspective direction for increasing the TGFB3 protein concentration in human and animal tissues.

The TIMP2 gene encodes the TIMP2 protein that constitutes an inhibitor of matrix metalloproteinases (MMP) and is involved in maintenance of tissue homeostasis. MMPs play an important role in physiological and pathological processes, including embryogenesis, tissue remodelling, wound healing, inflammation, arthritis, and cancer. The cells of some tumours themselves express MMP. By facilitating tumour invasion and metastasis, MMPs are also powerful stimulators of neoangiogenesis. Therefore, TIMP mediated inhibition of MMP can be one of the strategies for tumour therapy. TIMP-2 concentration in blood serum correlates with both the duration of remission and survival of patients with breast cancer. In ovarian cancer, a recombinant adenoviral vector expressing the TIMP2 gene has been shown to have an antitumour effect, both by inhibiting matrix metalloproteinases and by an MMP-independent mechanism of action (Yang S W et al. 2011).

Unlike other MMP inhibitors, TIMP2 has a direct inhibitory effect on the proliferation of endothelial cells, which potentially indicates the possibility of its use for the correction of conditions associated with pathological angiogenesis (Kim H J et al.//Cancer Lett. 2014 Feb. 28; 343(2):210-6).

Some alleles of TIMP2 gene are associated with the higher risk of developing osteoarthrosis of the knee joint (Xu P et al.//Oncotarget. 2017 Jan. 3; 8(1):1166-1176), quantity of active sperm (Kurzawski M et al.//Andrologia. 2017 June; 49(5)) and depressive disorders (Bobińska K et al.//J Affect Disord. 2016 Nov. 15; 205:119-129).

Insufficient expression of TIMP2 is associated with the development of myopia, while subconjunctival administration of TIMP2 protein prevented progression of this disease (Liu H H et al. 2017).

The enhanced migration of epidermal keratinocytes and accelerated wound healing in mice upon injection of the recombinant TIMP2 protein was demonstrated. It is also shown that TIMP2 inhibits collagen synthesis in fibroblast culture (Dohi, T., et al.//Plast Reconstr Surg Glob Open, 2015. 3(9): p. e520).

As was previously noted, a model of degenerative changes in vertebral discs in rabbits shows that the injection of a recombinant lentiviral vector expressing the survivin, TGFB3, and TIMP2 proteins helps slowing the degenerative changes in the vertebral discs (Yue B et al. 2016).

The FMOD gene encodes the FMOD protein (fibromodulin) that plays an important role in several normal and pathological processes. Fibromodulin protein belongs to the family of leucine-rich proteoglycans involved in scarless fetal wound healing (Soo, C., et al.//Am J Pathol, 2000. 157(2): p. 423-33). FMOD interacts with enzymes that form the structure of collagen fibers, thus participating in the process of extracellular matrix formation. It is also shown that FMOD is involved in the formation of muscle cells, cell reprogramming, and angiogenesis (Jan A T, Lee E J, Choi I.//Int J Biochem Cell Biol. 2016 November; 80:66-70).

It was shown that the expression level of fibromodullin is higher in fetus than in adult rat. The use of a recombinant adenoviral vector expressing FMOD results in the decrease in TGFB1 and TGFB2 expression and increase in TGFB3 expression in fibroblasts. Also, overexpression of fibromodullin results in the increase in TIMP2 expression, which results in the decrease in scar formation on the wound model in rabbits (Stoff, A., et al.//J Mol Med (Berl), 2007. 85(5): p. 481-96).

Thus, the background of the invention suggests that mutations in SKI, TGFB3, TIMP2, and FMOD genes or insufficient expression of proteins encoded by these genes are associated with the development of a spectrum of diseases, including, but not limited to, autoimmune diseases, hereditary and acquired pathological conditions, such as connective tissue damage, and other processes. This is why SKI, TGFB3, TIMP2, and FMOD genes are grouped within this patent. Genetic constructs that provide expression of proteins encoded by SKI, TGFB3, TIMP2, and FMOD genes can be used to develop drugs for the prevention and treatment of different diseases and pathological conditions.

Moreover, these data suggest that insufficient expression of proteins encoded by SKI, TGFB3, TIMP2, and FMOD genes included in the group of genes is associated not only with pathological conditions, but also with a predisposition to their development. Also, these data indicate that insufficient expression of these proteins may not appear explicitly in the form of a pathology that can be unambiguously described within the framework of existing clinical practice standards (for example, using the ICD code), but at the same time cause conditions that are unfavourable for humans and animals and associated with deterioration in the quality of life.

Analysis of approaches to increase the expression of therapeutic genes implies the practicability of use of different gene therapy vectors.

Gene therapy vectors are divided into viral, cell, and DNA vectors (Guideline on the quality, non-clinical, and clinical aspects of gene therapy medicinal Products EMA/CAT/80183/2014). Recently, gene therapy has paid increasingly more attention to the development of non-viral gene delivery systems with plasmid vectors topping the list. Plasmid vectors are free of limitations inherent in cell and viral vectors. In the target cell, they exist as an episome without being integrated into the genome, while producing them is quite cheap, and there is no immune response or side effects caused by the administration of plasmid vectors, which makes them a convenient tool for gene therapy and prevention of the genetic diseases (DNA vaccination) (Li L, Petrovsky N.//Expert Rev Vaccines. 2016; 15(3):313-29).

However, limitations of plasmid vectors use in gene therapy are: 1) presence of antibiotic resistance genes for the production of constructs in bacterial strains; 2) the presence of various regulatory elements represented by sequences of viral genomes; 3) length of therapeutic plasmid vector that determines the efficiency of vector delivery to the target cell.

It is known that the European Medicines Agency deems it necessary to refrain from adding antibiotic resistance marker genes to newly engineered plasmid vectors for gene therapy (Reflection paper on design modifications of gene therapy medicinal products during development/14 Dec. 2011 EMA/CAT/GTWP/44236/2009 Committee for advanced therapies). This recommendation is primarily related to the potential danger of the DNA vector penetration or horizontal antibiotic resistance gene transfer into the cells of bacteria found in the body as part of normal or opportunistic microflora. Furthermore, the presence of antibiotic resistance genes significantly increases the length of DNA vector, which reduces the efficiency of its penetration into eukaryotic cells.

It is important to note that antibiotic resistance genes also make a fundamental contribution to the method of production of DNA vectors. If antibiotic resistance genes are present, strains for the production of DNA vectors are usually cultured in medium containing a selective antibiotic, which poses risk of antibiotic traces in insufficiently purified DNA vector preparations. Thus, production of DNA vectors for gene therapy without antibiotic resistance genes is associated with the production of strains with such distinctive feature as the ability for stable amplification of therapeutic DNA vectors in the antibiotic-free medium.

In addition, the European Medicines Agency recommends avoiding the presence of regulatory elements in therapeutic plasmid vectors to increase the expression of therapeutic genes (promoters, enhancers, post-translational regulatory elements) that constitute nucleotide sequences of genomes of various viruses (Draft Guideline on the quality, non-clinical and clinical aspects of gene therapy medicinal products, www.ema.europa.eu/docs/en_GB/document library/Scientific guideline/2015/05/WC500187020.pdf). Although these sequences can increase the expression level of the therapeutic transgene, however, they pose risk of recombination with the genetic material of wild-type viruses and integration into the eukaryotic genome. Moreover, the relevance of overexpression of the particular gene for therapy remains an unresolved issue.

The size of the therapy vector is also essential. It is known that modern plasmid vectors often have unnecessary, non-functional sites that increase their length substantially (Mairhofer J, Grabherr R.//Mol Biotechnol. 2008.39(2):97-104). For example, ampicillin resistance gene in pBR322 series vectors, as a rule, consists of at least 1000 bp, which is more than 20% of the length of the vector itself. A reverse relationship between the vector length and its ability to penetrate into eukaryotic cells is observed; DNA vectors with a small length effectively penetrate into human and animal cells. For example, in a series of experiments on transfection of HELA cells with 383-4548 bp DNA vectors it was shown that the difference in penetration efficiency can be up to two orders of magnitude (100 times different) (Hornstein B D et al.//PLoS ONE. 2016; 11(12): e0167537).

Thus, when selecting a DNA vector, for reasons of safety and maximum effectiveness, preference should be given to those constructs that do not contain antibiotic resistance genes, the sequences of viral origin and length of which allows for the effective penetration into eukaryotic cells. A strain for production of such DNA vector in quantities sufficient for the purposes of gene therapy should ensure the possibility of stable DNA vector amplification using antibiotic-free nutrient media.

Example of usage of the recombinant DNA vectors for gene therapy is the method of producing a recombinant vector for genetic immunisation (U.S. Pat. No. 9,550,998 B2. The plasmid vector is a supercoiled plasmid DNA vector that is used for the expression of cloned genes in human and animal cells. The vector contains an origin of replication, regulatory elements comprising human cytomegalovirus promoter and enhancer, and regulatory sequences from the human T-cell lymphotropic virus.

The vector is accumulated in a dedicated *E. coli* strain free of antibiotics through antisense complementation of sacB gene inserted into the strain by means of bacteriophage. The disadvantage of this invention is the presence of regulatory elements in the composition of DNA vector that constitute sequences of viral genomes.

Application No. CN101818171A that describes a method for enhancing the expression of the SKI gene using the gene therapy DNA vector pUC118-Ski for healing human wounds is known. The disadvantage of this invention is the use of a DNA vector containing sequences of viral origin (CMV promoter) and ampicillin resistance gene, as well as the limited scope of application.

Application No. WO1996039196A1 that describes a method for modulating connective tissue by injecting a DNA vector or autologous chondrocytes transformed with a DNA vector expressing a gene selected from the group of genes, including TGFB3 and TIMP2 genes is known. The disadvantage of this invention is the limited use and the vague safety requirements applied to the DNA vectors.

Application No. CN102448983A that proposes the use of recombinant FMOD protein for the correction of conditions associated with insufficient FMOD function is known. The disadvantage of this invention is the use of recombinant protein instead of gene therapy approach in order to increase the FMOD gene expression.

The prototype of this invention in terms of using gene therapy approaches to increase the expression level of genes from the SKI, TGFB3, TIMP2, and FMOD group is Application No. JP2018512876A that describes the use of oligonucleotides, in particular non-coding RNA, to increase the expression of genes, including genes from the SKI, TGFB3, TIMP2, and FMOD group. One of the methods for delivering non-coding RNAs proposed in this application is the use of vectors, including DNA vectors represented by plasmids. The disadvantage of this prototype is the mechanism of increase of gene expression that involves the mediated action of non-coding RNA.

SUMMARY

The purpose of this invention is to construct the gene therapy DNA vectors in order to increase the expression level of a group of SKI, TGFB3, TIMP2, and FMOD genes in human and animal organisms that combine the following properties:

Efficiency of gene therapy DNA vector in order to increase the expression level of therapeutic genes in eukaryotic cells.

Possibility of safe use in gene therapy of human beings and animals due to the absence of regulatory elements representing the nucleotide sequences of viral genomes in the gene therapy DNA vector.

Possibility of safe use in the gene therapy of human beings and animals due to the absence of antibiotic resistance genes in the gene therapy DNA vector.

Producibility and constructability of gene therapy DNA vector on an industrial scale.

Item II and III are provided for herein in line with the recommendations of the state regulators for gene therapy medicines and, specifically, the requirement of the European Medicines Agency to refrain from adding antibiotic resistance marker genes to newly engineered plasmid vectors for gene therapy (Reflection paper on design modifications of gene therapy medicinal products during development/14 Dec. 2011 EMA/CAT/GTWP/44236/2009 Committee for advanced therapies) and refrain from adding viral genomes to newly engineered plasmid vectors for gene therapy (Guideline on the quality, non-clinical and clinical aspects of gene therapy medicinal products/23 Mar. 2015, EMA/CAT/80183/2014, Committee for Advanced Therapies).

The purpose of the invention also includes the construction of strains carrying these gene therapy DNA vectors for the development and production of these gene therapy DNA vectors on an industrial scale.

The specified purpose is achieved by using the produced gene therapy DNA vector based on the gene therapy DNA vector VTvaf17 for treatment of diseases associated with development of fibrosis of tissues, formation of scars, connective tissue damage, and for acceleration of acceleration of wound healing, reepithelialisation, for increasing the formation of granulation tissue, and inhibition of scar formation via the increase of expression of SKI, TGFB3, TIMP2, and FMOD therapeutic genes in humans and animals.

This is gene therapy DNA vector based on the gene therapy DNA vector VTvaf17 that has the coding region of SKI therapeutic gene cloned to gene therapy DNA vector VTvaf17 resulting in gene therapy DNA vector VTvaf17-SKI that has nucleotide sequence SEQ ID NO: 1,
  gene therapy DNA vector based on the gene therapy DNA vector VTvaf17 that has the coding region of TGFB3 therapeutic gene cloned to gene therapy DNA vector VTvaf17 resulting in gene therapy DNA vector VTvaf17-TGFB3 that has nucleotide sequence SEQ ID NO: 2,
  gene therapy DNA vector based on the gene therapy DNA vector VTvaf17 that has the coding region of TIMP2 therapeutic gene cloned to gene therapy DNA vector VTvaf17 resulting in gene therapy DNA vector VTvaf17-TIMP2 that has nucleotide sequence SEQ ID NO: 3,
  gene therapy DNA vector based on the gene therapy DNA vector VTvaf17 that has the coding region of FMOD therapeutic gene cloned to gene therapy DNA vector VTvaf17 resulting in gene therapy DNA vector VTvaf17-FMOD that has nucleotide sequence SEQ ID NO: 4.

Each of the constructed gene therapy DNA vectors based on gene therapy DNA vector VTvaf17 carrying the SKI, or TGFB3, or TIMP2, or FMOD therapeutic gene, namely gene therapy DNA vectors VTvaf17-SKI, or VTvaf17-TGFB3, or VTvaf17-TIMP2, or VTvaf17-FMOD due to the limited size of VTvaf17 vector part not exceeding 3200 bp has the ability to efficiently penetrate into human and animal cells and express the SKI, or TGFB3, or TIMP2, or FMOD therapeutic gene cloned to it.

At the same time, nucleotide sequences that are not antibiotic resistance genes, virus genes, or regulatory elements of viral genomes are used as structure elements, which ensures its safe use for gene therapy in humans and animals.

A method of gene therapy DNA vector production based on gene therapy DNA vector VTvaf17 carrying the SKI, or TGFB3, or TIMP2, or FMOD therapeutic gene has been also developed that involves obtaining each of gene therapy DNA vectors: VTvaf17-SKI, or VTvaf17-TGFB3, or VTvaf17-TIMP2, or VTvaf17-FMOD as follows: the coding region of the SKI, or TGFB3, or TIMP2, or FMOD therapeutic gene is cloned to DNA vector VTvaf17, and gene therapy DNA vector VTvaf17-SKI, SEQ ID NO: 1, or VTvaf17-TGFB3, SEQ ID NO: 2 or VTvaf17-TIMP2, SEQ ID NO: 3, or VTvaf17-FMOD, SEQ ID NO: 4, respectively, is obtained.

The method of use of the constructed gene therapy DNA vector based on gene therapy DNA vector VTvaf17 carrying the SKI, or TGFB3, or TIMP2, or FMOD therapeutic gene for treatment of diseases associated with development of fibrosis of tissues, formation of scars, connective tissue damage, and for acceleration of acceleration of wound healing, reepithelialisation, for increasing the formation of granulation tissue, and inhibition of scar formation via the increase of expression of SKI, TGFB3, TIMP2, and FMOD therapeutic genes in humans and animals is to transfect the cells of human or animal organs and tissues with the selected gene therapy DNA vector carrying the therapeutic gene based on gene therapy DNA vector VTvaf17 or several selected gene therapy DNA vectors carrying the therapeutic genes based on gene therapy DNA vector VTvaf17 of the constructed gene therapy DNA vectors carrying therapeutic genes based on gene therapy DNA vector VTvaf17, namely VTvaf17-SKI, or VTvaf17-TGFB3, or VTvaf17-TIMP2, or VTvaf17-FMOD, and/or to inject human or animal autologous cells of said patient or animal transfected with the selected gene therapy DNA vector carrying the therapeutic gene based on gene therapy DNA vector VTvaf17 or several selected gene therapy DNA vectors carrying the therapeutic genes based on gene therapy DNA vector VTvaf17 of the constructed gene therapy DNA vectors carrying therapeutic genes into human or animal organs and tissues, or to use a combination of the indicated methods.

The method of production of strain for construction of a gene therapy DNA vector for treatment of diseases associated with development of fibrosis of tissues, formation of scars, connective tissue damage, and for acceleration of acceleration of wound healing, reepithelialisation, for increasing the formation of granulation tissue, and inhibition of scar formation via the increase of expression of SKI, or TGFB3, or TIMP2, or FMOD therapeutic genes in humans and animals involves making electrocompetent cells of *Escherichia coli* strain SCS110-AF and subjecting these cells to electroporation with the constructed gene therapy DNA vector and subsequent selection of stable clones of the strain using selective medium.

*Escherichia coli* strains SCS110-AF/VTvaf17-SKI, or *Escherichia coli* strain CS110-AF/VTvaf17-TGFB3, or *Escherichia coli* strain SCS110-AF/VTvaf17-TIMP2, or *Escherichia coli* strain SCS110-AF/VTvaf17-FMOD carrying gene therapy DNA vector VTvaf17s VTvaf17-SKI, or VTvaf17-TGFB3, or VTvaf17-TIMP2, or VTvaf17-FMOD, respectively, for production thereof are claimed.

The method of production on an industrial scale of gene therapy DNA vector based on gene therapy DNA vector VTvaf17 carrying the SKI, or TGFB3, or TIMP2, or FMOD therapeutic gene for treatment of diseases associated with development of fibrosis of tissues, formation of scars, connective tissue damage, and for acceleration of acceleration of wound healing, reepithelialisation, for increasing the formation of granulation tissue, and inhibition of scar formation via the increase of expression of SKI, TGFB3, TIMP2, and FMOD therapeutic genes in humans and animals involves scaling-up the bacterial culture of the strain to the quantities necessary for increasing the bacterial biomass in an industrial fermenter, after which the biomass is used to extract a fraction containing the therapeutic DNA product, i.e. the gene therapy DNA vector VTvaf17-SKI, or VTvaf17-TGFB3, or VTvaf17-TIMP2, or VTvaf17-FMOD, respectively.

BRIEF DESCRIPTION OF THE DRAWINGS

The essence of the invention is explained in the drawings, where:

FIGS. 1A-1D show shews the structures corresponding to:
- A—gene therapy DNA vector VTvaf17-SKI,
- B—gene therapy DNA vector VTvaf17-TGFB3,
- C—gene therapy DNA vector VTvaf17-TIMP2,
- D—gene therapy DNA vector VTvaf17-FMOD.

The following structural elements of the vector are indicated in the structures:
- EF1aprom—the promoter region of human elongation factor EF1A with an intrinsic enhancer contained in the first intron of the gene. It ensures efficient transcription of the recombinant gene in most human tissues,
- The reading frame of the therapeutic gene corresponding to the coding region of the SKI gene (FIG. 1A), or TGFB3 (FIG. 1B), or TIMP2 (FIG. 1C), or FMOD (FIG. 1D), respectively,
- hGH-TAterm—the transcription terminator and the polyadenylation site of the human growth factor gene,
- pBR322 on—the origin of replication for autonomous replication with a single nucleotide substitution to increase plasmid production in the cells of most *Escherichia coli* strains.

Unique restriction sites are marked.

Figure 2:
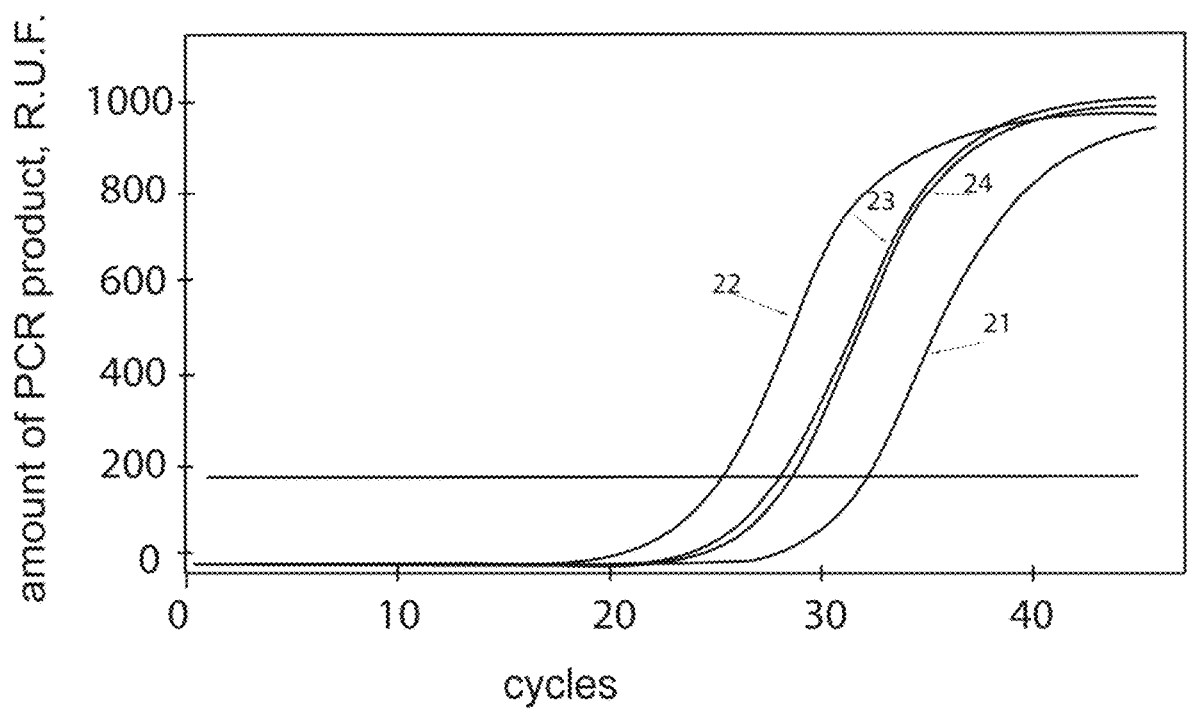

FIG. 2 shows diagrams of cDNA amplicon accumulation of the therapeutic gene, namely the SKI gene, in HDFa primary human dermal fibroblast cell culture (ATCC PCS-201-01) before its transfection and 48 hours after transfection of these cells with gene therapy DNA vector VTvaf17-SKI in order to assess the ability to penetrate into eukaryotic cells and functional activity, i.e. expression of the therapeutic gene at the mRNA level.

Curves of accumulation of amplicons during the reaction are shown in FIG. 2 corresponding to:
- 21—cDNA of SKI gene in HDFa primary human dermal fibroblast cell culture before transfection with DNA vector VTvaf17-SKI,
- 22—cDNA of SKI gene in HDFa primary human dermal fibroblast cell culture after transfection with DNA vector VTvaf17-SKI,
- 23—cDNA of B2M gene in HDFa primary human dermal fibroblast cell culture before transfection with DNA vector VTvaf17-SKI,
- 24—cDNA of B2M gene in HDFa primary human dermal fibroblast cell culture after transfection with DNA vector VTvaf17-SKI.

B2M (beta-2-microgobuline) gene listed in the GenBank database under number NM 004048.2 was used as a reference gene.

Figure 3:
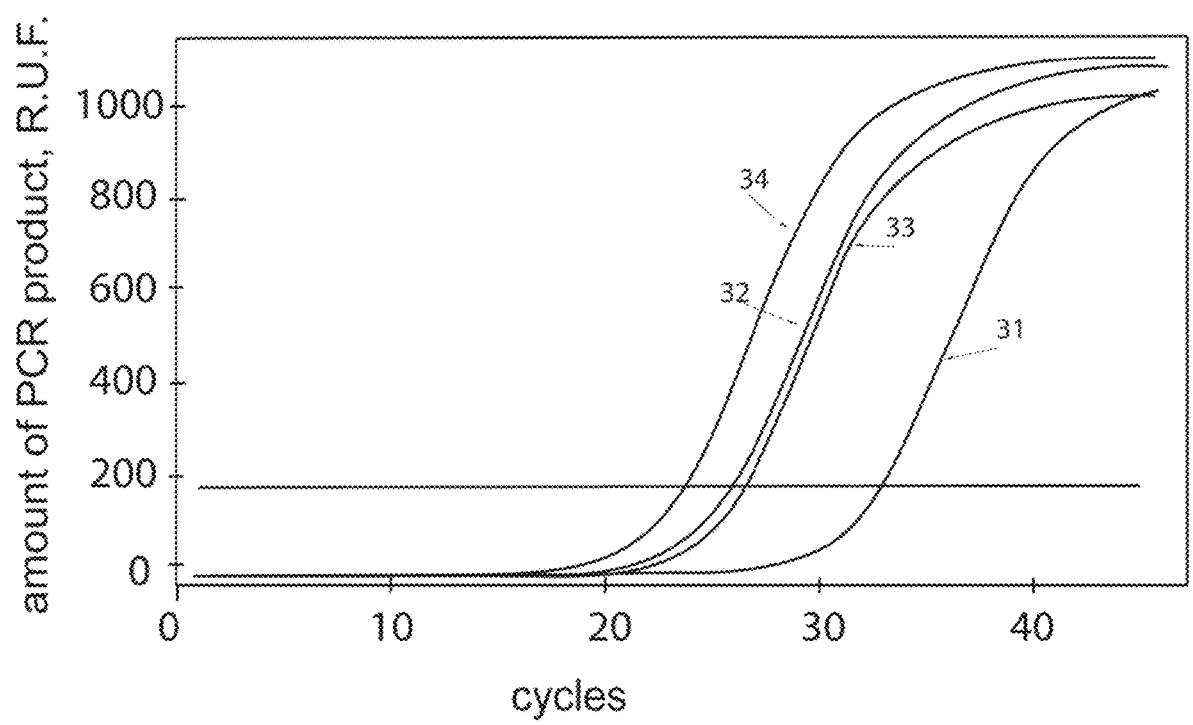

FIG. 3 shows diagrams of cDNA amplicon accumulation of the therapeutic gene, namely the TGFB3 gene, in HEKa primary human epidermal keratinocyte cell culture (ATCC PCS-200-01) before its transfection and 48 hours after transfection of these cells with gene therapy DNA vector VTvaf17-TGFB3 in order to assess the ability to penetrate into eukaryotic cells and functional activity, i.e. expression of the therapeutic gene at the mRNA level.

Curves of accumulation of amplicons during the reaction are shown in FIG. 3 corresponding to:
- 31—cDNA of TGFB3 gene in HEKa primary human epidermal keratinocyte cell culture before transfection with DNA vector VTvaf17-TGFB3,
- 32—cDNA of TGFB3 gene in HEKa primary human epidermal keratinocyte cell culture after transfection with DNA vector VTvaf17-TGFB3,
- 33—cDNA of B2M gene in HEKa primary human epidermal keratinocyte cell culture before transfection with DNA vector VTvaf17-TGFB3,
- 34—cDNA of B2M gene in HEKa primary human epidermal keratinocyte cell culture after transfection with DNA vector VTvaf17-TGFB3.

B2M (beta-2-microgobuline) gene listed in the GenBank database under number NM 004048.2 was used as a reference gene.

Figure 4:
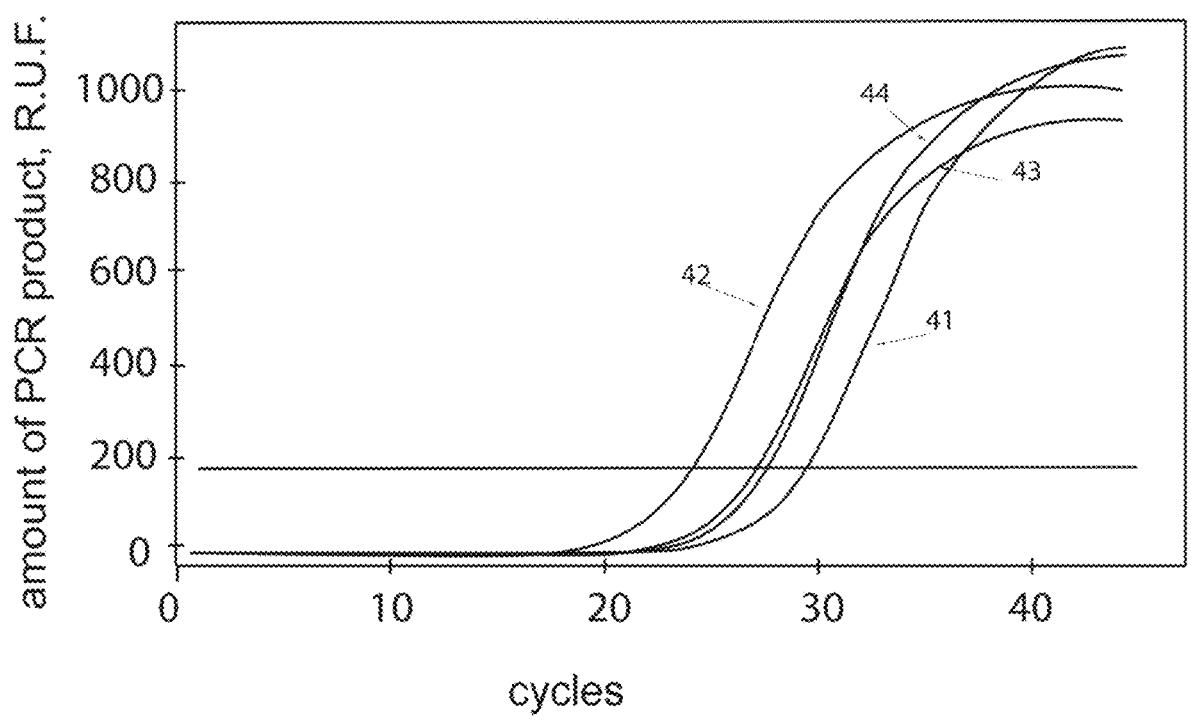

FIG. 4 shows diagrams of cDNA amplicon accumulation of the therapeutic gene, namely the TIMP2 gene, in Hs27 human primary foreskin fibroblast cell line (ATCC CRL-1634) before its transfection and 48 hours after transfection of these cells with gene therapy DNA vector VTvaf17-TIMP2 in order to assess the ability to penetrate into eukaryotic cells and functional activity, i.e. expression of the therapeutic gene at the mRNA level.

Curves of accumulation of amplicons during the reaction are shown in FIG. 4 corresponding to:
- 41—cDNA of TIMP2 gene in Hs27 human primary foreskin fibroblast cell line before transfection with DNA vector VTvaf17-TIMP2,
- 42—cDNA of TIMP2 gene in Hs27 human primary foreskin fibroblast cell line after transfection with DNA vector VTvaf17-TIMP2,
- 43—cDNA of B2M gene in Hs27 human primary foreskin fibroblast cell line before transfection with DNA vector VTvaf17-TIMP2,
- 44—cDNA of B2M gene in Hs27 human primary foreskin fibroblast cell line after transfection with DNA vector VTvaf17-TIMP2.

B2M (beta-2-microgobuline) gene listed in the GenBank database under number NM 004048.2 was used as a reference gene.

Figure 5:
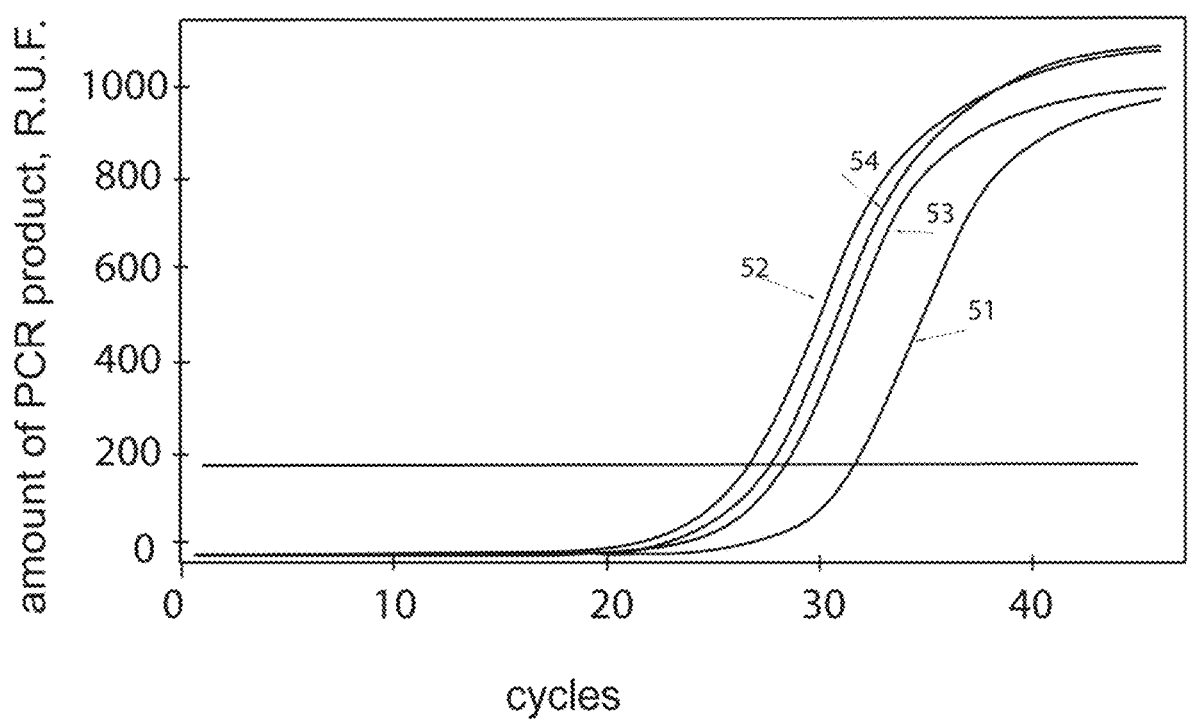

FIG. 5 shows diagrams of cDNA amplicon accumulation of the therapeutic gene, namely the FMOD gene, in HMEC-1 human dermal microvascular endothelial cell line (ATCC CRL-3243) before their transfection and 48 hours after transfection of these cells with gene therapy DNA vector VTvaf17-FMOD in order to assess the ability to penetrate into eukaryotic cells and functional activity, i.e. expression of the therapeutic gene at the mRNA level.

Curves of accumulation of amplicons during the reaction are shown in FIG. 5 corresponding to:
- 51—cDNA of FMOD gene in HMEC-1 human dermal microvascular endothelial cell line before transfection with DNA vector VTvaf17-FMOD,
- 52—cDNA of FMOD gene in HMEC-1 human dermal microvascular endothelial cell line after transfection with DNA vector VTvaf17-FMOD,
- 53—cDNA of B2M gene in HMEC-1 human dermal microvascular endothelial cell line before transfection with DNA vector VTvaf17-FMOD,
- 54—cDNA of B2M gene in HMEC-1 human dermal microvascular endothelial cell line after transfection with DNA vector VTvaf17-FMOD.

B2M (beta-2-microgobuline) gene listed in the GenBank database under number NM 004048.2 was used as a reference gene.

Figure 6:
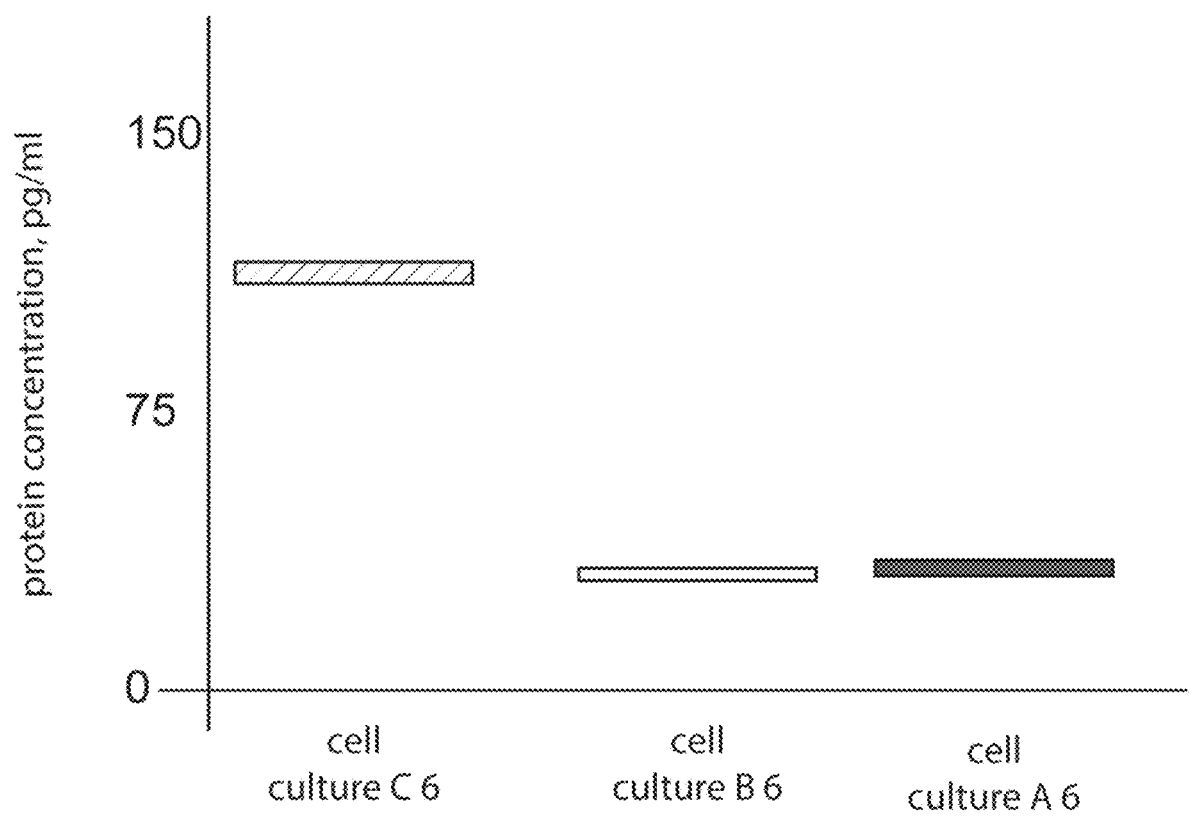

FIG. 6 shows the plot of SKI protein concentration in the cell lysate of HDFa human primary dermal fibroblasts (ATCC PCS-201-01) after transfection of these cells with DNA vector VTvaf17-SKI in order to assess the functional activity, i.e. expression at the protein level based on the SKI protein concentration change in the cell lysate.

The following elements are indicated in FIG. 6:
culture A 6—HDFa human primary dermal fibroblast cell culture transfected with aqueous dendrimer solution without plasmid DNA (reference),
culture B 6—HDFa human primary dermal fibroblast cell culture transfected with DNA vector VTvaf17,
culture C 6—HDFa human primary dermal fibroblast cell culture transfected with DNA vector VTvaf17-SKI.

Figure 7:
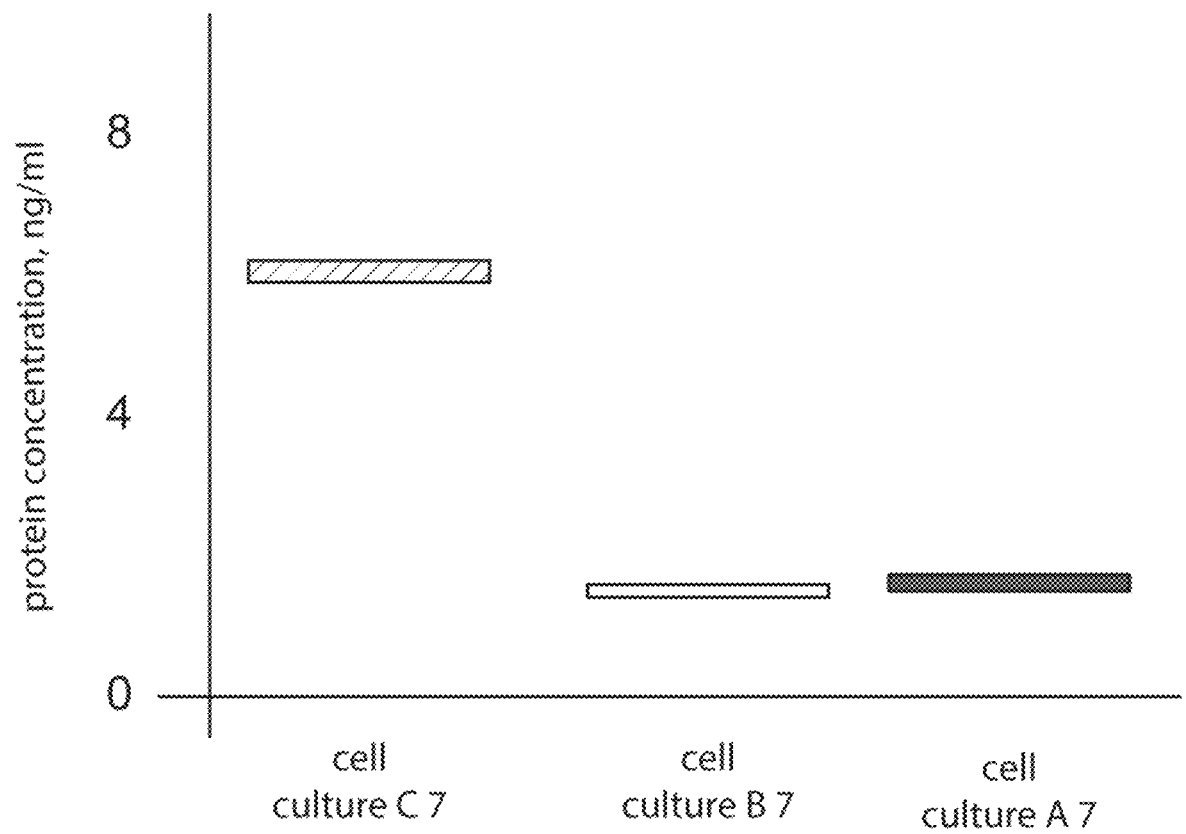

FIG. 7 shows the plot of TGFB3 protein concentration in the lysate of HEKa primary human epidermal keratinocyte cells (ATCC PCS-200-01) after transfection of these cells with gene therapy DNA vector VTvaf17-TGFB3 in order to assess the functional activity, i.e. the therapeutic gene expression at the protein level, and the possibility of increasing the level of protein expression by gene therapy DNA vector based on gene therapy vector VTvaf17 carrying the TGFB3 therapeutic gene.

The following elements are indicated in FIG. 7:
culture A 7—HEKa primary human epidermal keratinocyte cell culture transfected with aqueous dendrimer solution without plasmid DNA (reference),
culture B 7—HEKa primary human epidermal keratinocyte cell culture transfected with DNA vector VTvaf17,
culture C 7—HEKa primary human epidermal keratinocyte cell culture transfected with DNA vector VTvaf17-TGFB3.

Figure 8:
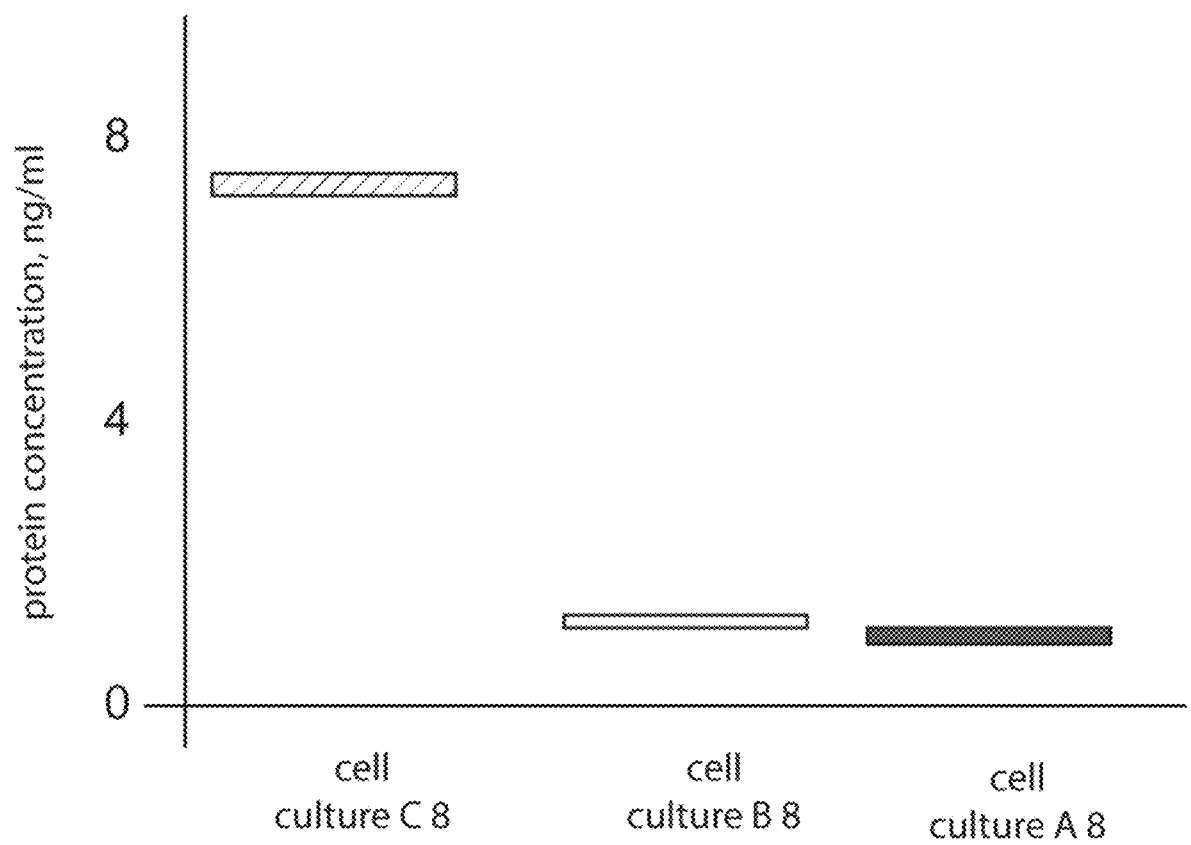

FIG. 8 shows the plot of TIMP2 protein concentration in the lysate of Hs27 human primary foreskin fibroblast cell line (ATCC CRL-1634) after transfection of these cells with DNA vector VTvaf17-TIMP2 in order to assess the functional activity, i.e. the therapeutic gene expression at the protein level, and the possibility of increasing the level of protein expression by gene therapy DNA vector based on gene therapy DNA vector VTvaf17 carrying the TIMP2 therapeutic gene.

The following elements are indicated in FIG. 8:
culture A8—Hs27 human foreskin fibroblast cell culture transfected with aqueous dendrimer solution without plasmid DNA (reference),
culture B 8—Hs27 human foreskin fibroblast cell culture transfected with DNA vector VTvaf17,
culture C 8—Hs27 human foreskin fibroblast cell culture transfected with DNA vector VTvaf17-TIMP2.

Figure 9:
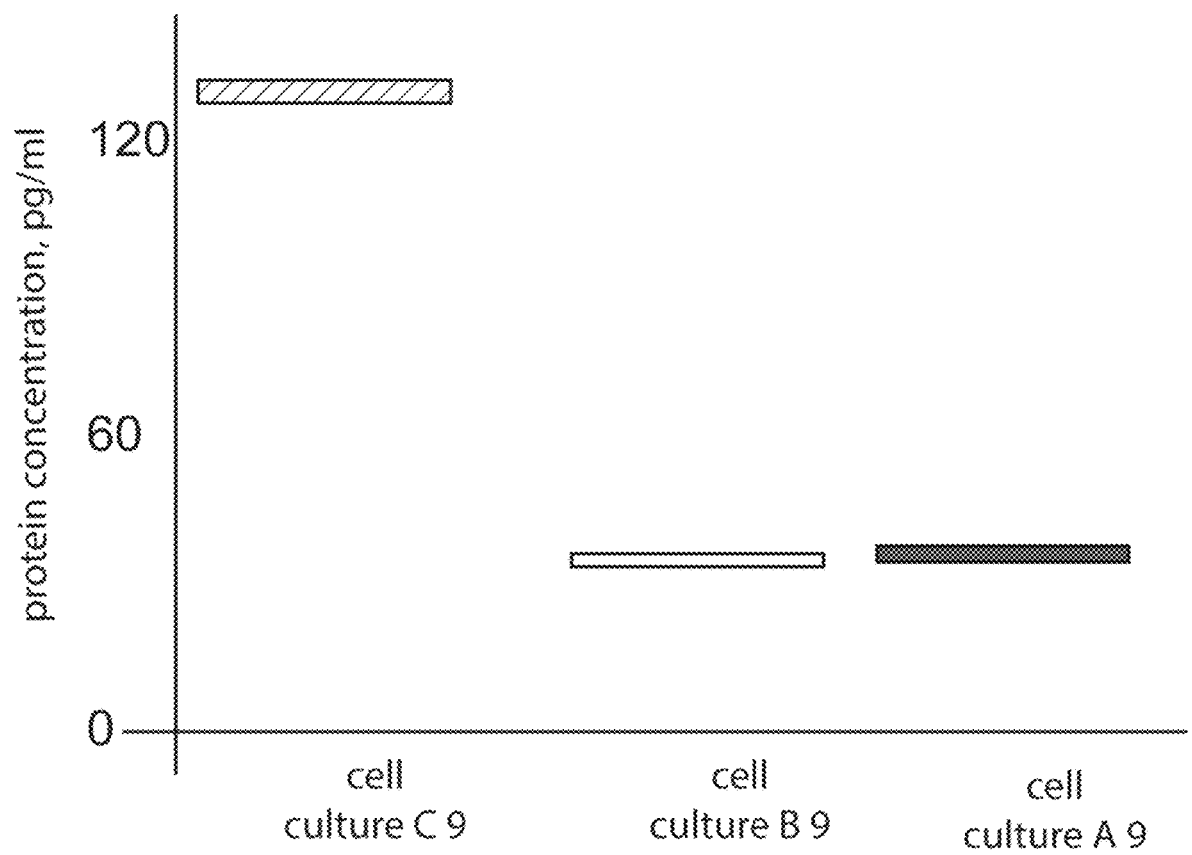

FIG. 9 shows the plot of FMOD protein concentration in the lysate of HMEC-1 human dermal microvascular endothelial cell line (ATCC CRL-3243) after transfection of these cells with DNA vector VTvaf17-FMOD in order to assess the functional activity, i.e. the therapeutic gene expression at the protein level, and the possibility of increasing the level of protein expression by gene therapy DNA vector based on gene therapy DNA vector VTvaf17 carrying the FMOD therapeutic gene.

The following elements are indicated in FIG. 9:
culture A 9—HMEC-1 human dermal microvascular endothelial cell line transfected with aqueous dendrimer solution without plasmid DNA (reference),
culture B 9—HMEC-1 human dermal microvascular endothelial cell line transfected with DNA vector VTvaf17,
culture C 9—HMEC-1 human dermal microvascular endothelial cell line transfected with DNA vector VTvaf17-FMOD.

Figure 10:
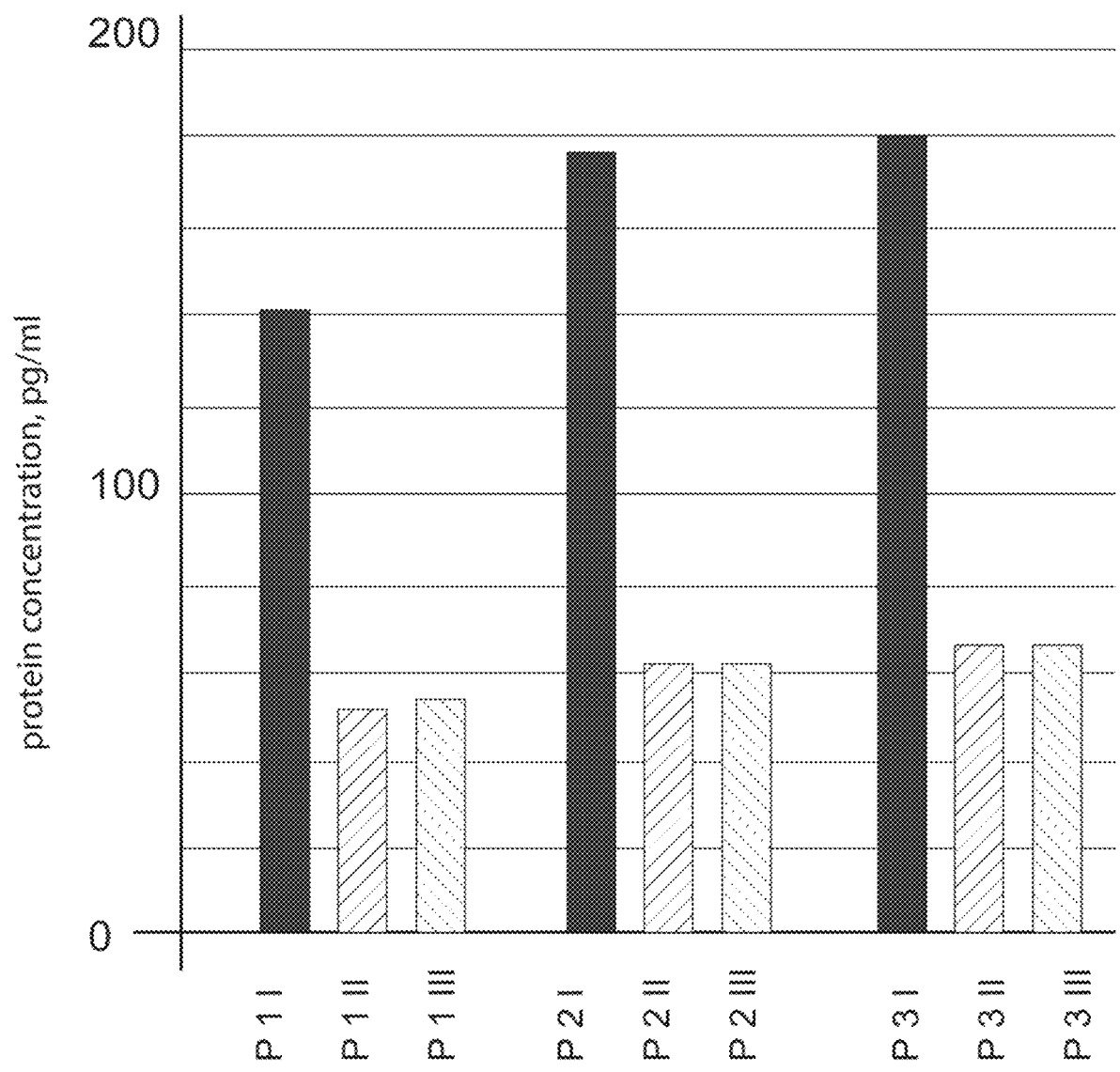

FIG. 10 shows the plot of FMOD protein concentration in the skin biopsy specimens of three patients after injection of gene therapy DNA vector VTvaf17-FMOD into the skin of these patients in order to assess the functional activity, i.e. the expression of the therapeutic gene at the protein level, and the possibility of increasing the level of protein expression using gene therapy DNA vector based on gene therapy vector VTvaf17 carrying the FMOD therapeutic gene.

The following elements are indicated in FIG. 10:
P1I—patient P1 skin biopsy in the region of injection of gene therapy DNA vector VTvaf17-FMOD,
P1II—patient P1 skin biopsy in the region of injection of gene therapy DNA vector VTvaf17 (placebo),
P1III—patient P1 skin biopsy from intact site,
P2I—patient P2 skin biopsy in the region of injection of gene therapy DNA vector VTvaf17-FMOD,
P2II—patient P2 skin biopsy in the region of injection of gene therapy DNA vector VTvaf17 (placebo),
P2III—patient P2 skin biopsy from intact site,
P3I—patient P3 skin biopsy in the region of injection of gene therapy DNA vector VTvaf17-FMOD,
P3II—patient P3 skin biopsy in the region of injection of gene therapy DNA vector VTvaf17 (placebo),
P3III—patient P3 skin biopsy from intact site.

Figure 11:
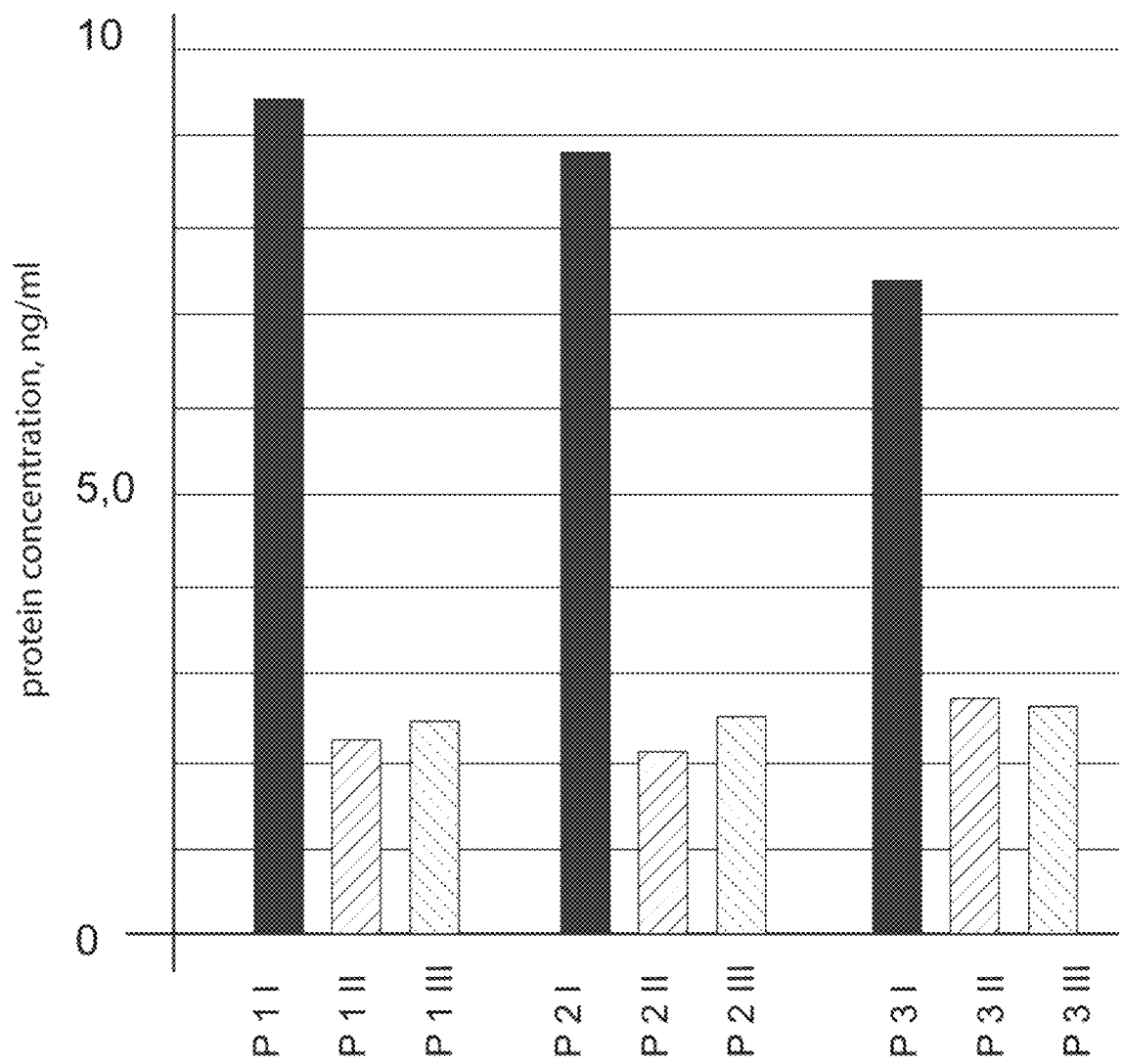

FIG. 11 shows the plot of TIMP2 protein concentration in the gastrocnemius muscle biopsy specimens of three patients after injection of gene therapy DNA vector VTvaf17-TIMP2 into the gastrocnemius muscle of these patients in order to assess the functional activity, i.e. the therapeutic gene expression at the protein level, and the possibility of increasing the level of protein expression using gene therapy DNA vector based on gene therapy DNA vector VTvaf17 carrying the TIMP2 therapeutic gene.

The following elements are indicated in FIG. 11:
P1I—patient P1 gastrocnemius muscle biopsy in the region of injection of gene therapy DNA vector VTvaf17-TIMP2,
P1II—patient P1 gastrocnemius muscle biopsy in the region of injection of gene therapy DNA vector VTvaf17 (placebo),
P1III—patient P1 gastrocnemius muscle biopsy from intact site,
P2I—patient P2 gastrocnemius muscle biopsy in the region of injection of gene therapy DNA vector VTvaf17-TIMP2,
P2II—patient P2 gastrocnemius muscle biopsy in the region of injection of gene therapy DNA vector VTvaf17 (placebo),
P2III—patient P2 gastrocnemius muscle biopsy from intact site,
P3I— patient P3 gastrocnemius muscle biopsy in the region of injection of gene therapy DNA vector VTvaf17-TIMP2,
P3II—patient P3 gastrocnemius muscle biopsy in the region of injection of gene therapy DNA vector VTvaf17 (placebo),
P3III—patient P3 gastrocnemius muscle biopsy from intact site.

Figure 12:
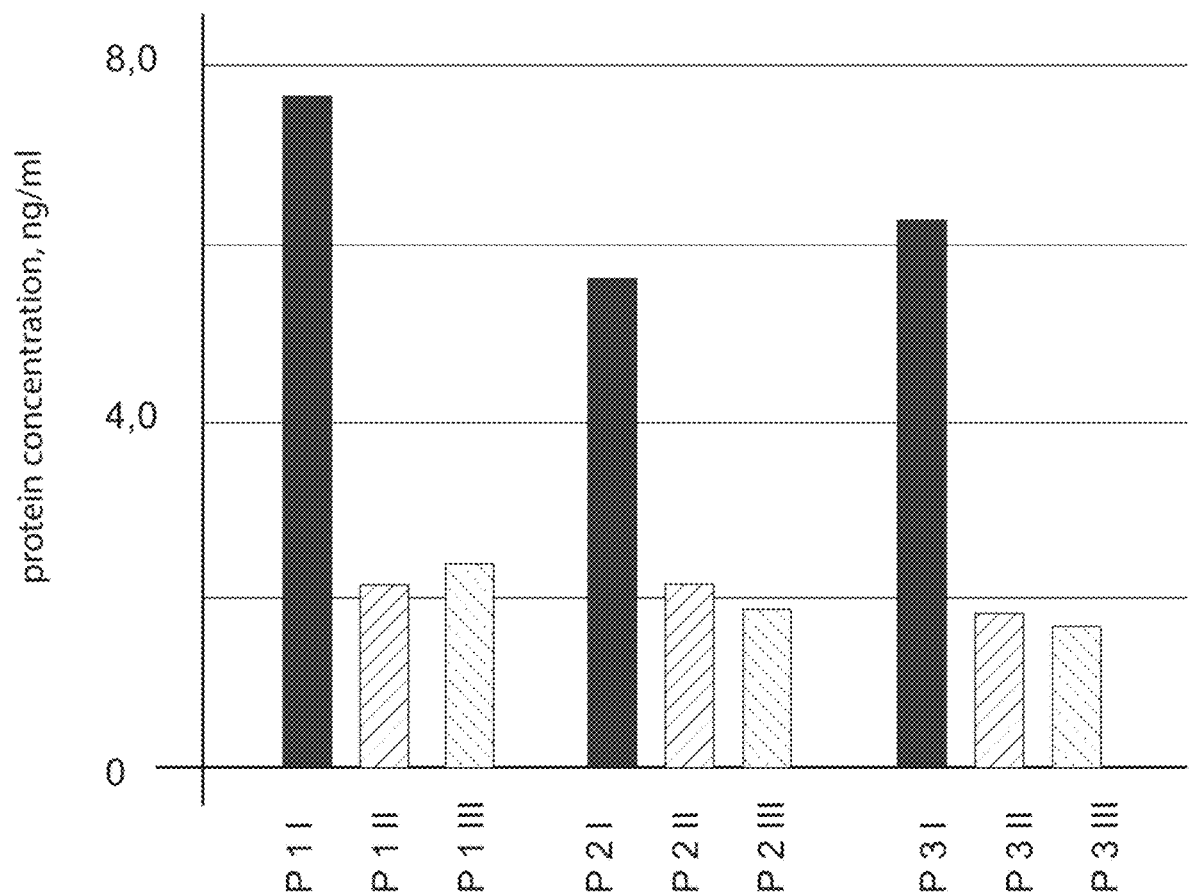

FIG. 12 shows the plot of TGFB3 protein concentration in the skin biopsy specimens of three patients after injection of gene therapy DNA vector VTvaf17-TGFB3 into the skin of these patients in order to assess the functional activity, i.e. the expression of the therapeutic gene at the protein level, and the possibility of increasing the level of protein expression using gene therapy DNA vector based on gene therapy vector VTvaf17 carrying the-TGFB3 therapeutic gene.

The following elements are indicated in FIG. 12:
P1I—patient P1 skin biopsy in the region of injection of gene therapy DNA vector VTvaf17-TGFB3,
P1II—patient P1 skin biopsy in the region of injection of gene therapy DNA vector VTvaf17 (placebo),
P1III—patient P1 skin biopsy from intact site,
P2I—patient P2 skin biopsy in the region of injection of gene therapy DNA vector VTvaf17-TGFB3,
P2II—patient P2 skin biopsy in the region of injection of gene therapy DNA vector VTvaf17 (placebo),
P2III—patient P2 skin biopsy from intact site,
P3I—patient P3 skin biopsy in the region of injection of gene therapy DNA vector VTvaf17-TGFB3,
P3II—patient P3 skin biopsy in the region of injection of gene therapy DNA vector VTvaf17 (placebo),
P3III—patient P3 skin biopsy from intact site.

Figure 13:
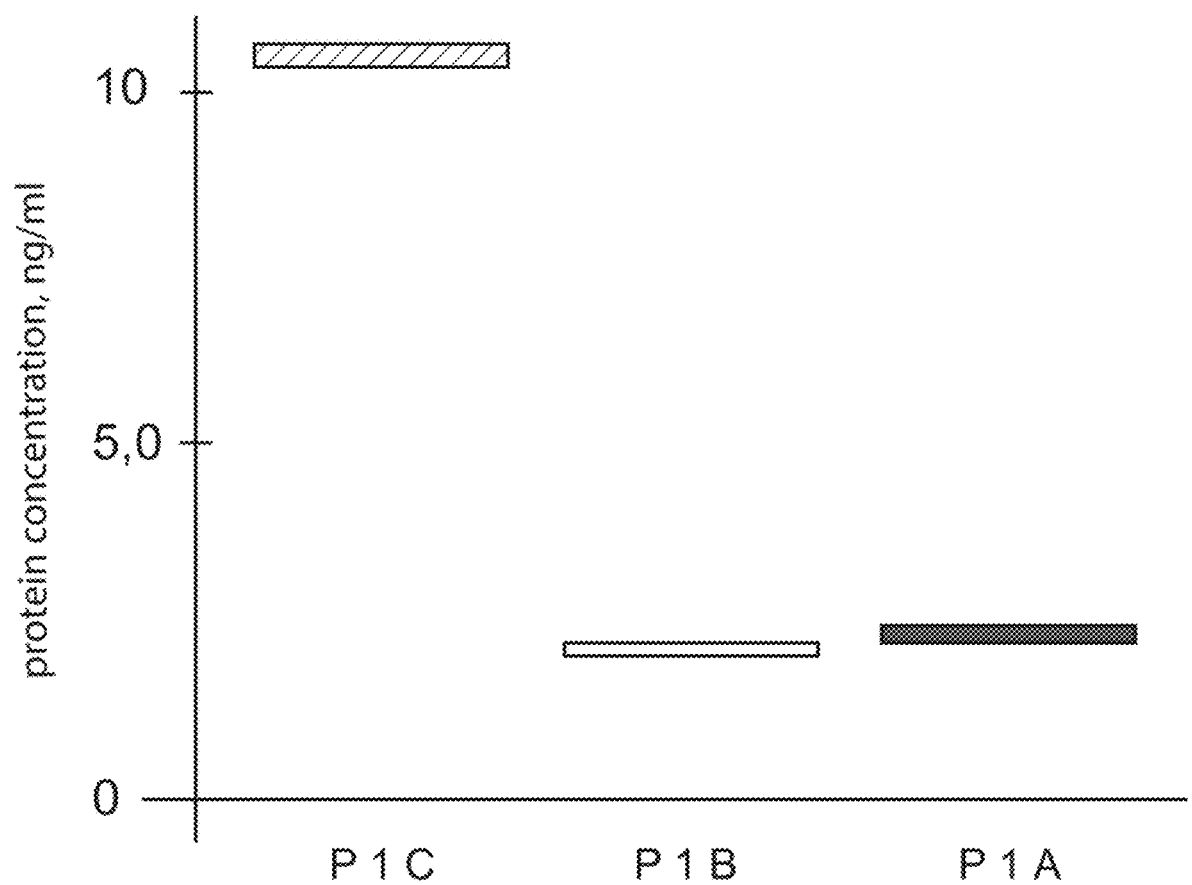

FIG. 13 shows the plot of TGFB3 protein concentration in human skin biopsy samples after subcutaneous injection of autologous fibroblast cell culture transfected with the gene therapy DNA vector VTvaf17-TGFB3 in order to demonstrate the method of use by injecting autologous cells transfected with the gene therapy DNA vector VTvaf17-TGFB3.

The following elements are indicated in FIG. 13:
P1A—patient P1 skin biopsy in the region of injection of autologous fibroblast culture of the patient transfected with gene therapy DNA vector VTvaf17-TGFB3,
P1B—patient P1 skin biopsy in the region of injection of autologous fibroblasts of the patient transfected with gene therapy DNA vector VTvaf17,
P1C—patient P1 skin biopsy from intact site.

Figure 14A:
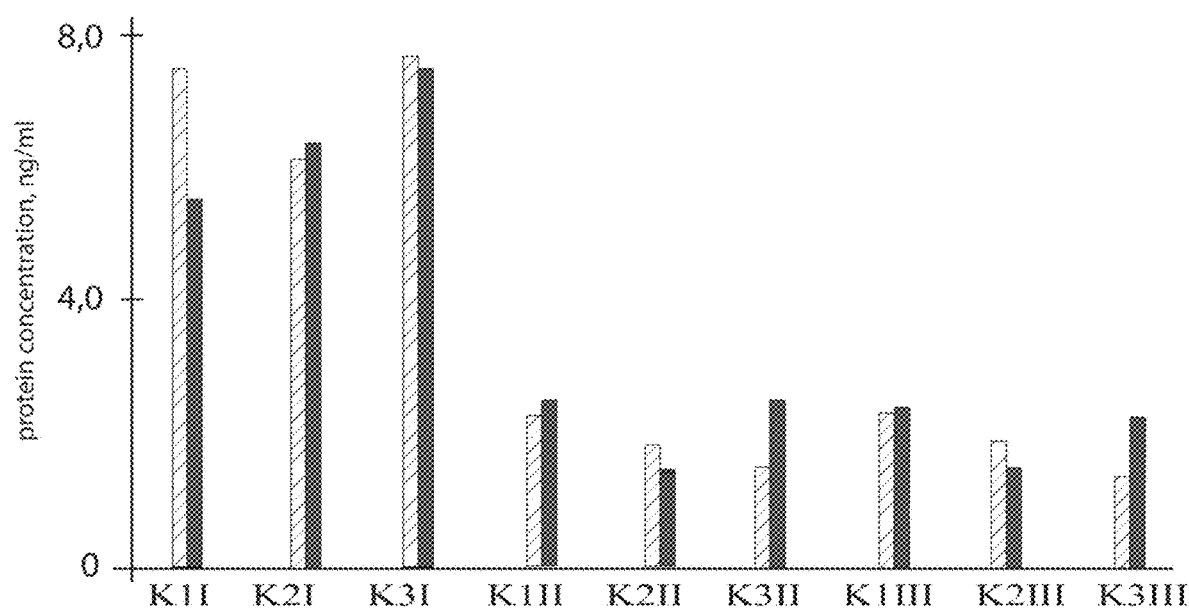
Figure 14B:
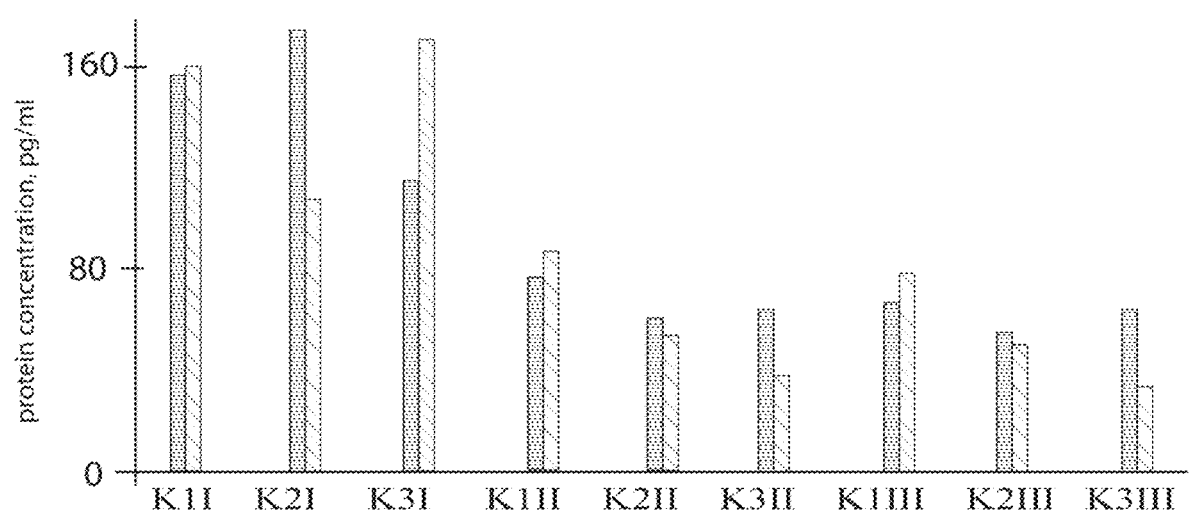

FIGS. 14A and 14B show the plot of concentrations of human SKI protein, human TGFB3 protein, human TIMP2 protein, and human FMOD protein in biopsy samples of three Wistar rats in the site of preliminary surgically modelled flat wound scar after injection of a mixture of gene therapy vectors: gene therapy DNA vector VTvaf17-SKI, gene therapy DNA vector VTvaf17-TGFB3, gene therapy DNA vector VTvaf17-TIMP2, and gene therapy DNA vector VTvaf17-FMOD in order to demonstrate the method of use of a mixture of gene therapy DNA vectors.

The following elements are indicated in FIGS. 14 A and 14B:
K1I—rat K1 skin biopsy sample in the region of injection of a mixture of gene therapy DNA vectors: VTvaf17-SKI, VTvaf17-TGFB3, VTvaf17-TIMP2, and VTvaf17-FMOD,
K1II—rat K1 skin biopsy sample in the region of injection of gene therapy DNA vector VTvaf17 (placebo),
K1 III—rat K1 skin biopsy sample of the reference intact site,
K2I—rat K2 skin biopsy sample in the region of injection of a mixture of gene therapy DNA vectors: VTvaf17-SKI, VTvaf17-TGFB3, VTvaf17-TIMP2, and VTvaf17-FMOD,
K2II—rat K2 skin biopsy sample in the region of injection of gene therapy DNA vector VTvaf17 (placebo),
K2III—rat K2 skin biopsy sample of the reference intact site,
K3I—rat K3 skin biopsy sample in the region of injection of a mixture of gene therapy DNA vectors: VTvaf17-SKI, VTvaf17-TGFB3, VTvaf17-TIMP2, and VTvaf17-FMOD,
K3II—rat K3 skin biopsy sample in the region of injection of gene therapy DNA vector VTvaf17 (placebo),
K3III—rat K3 skin biopsy sample of the reference intact site.

Figure 15:
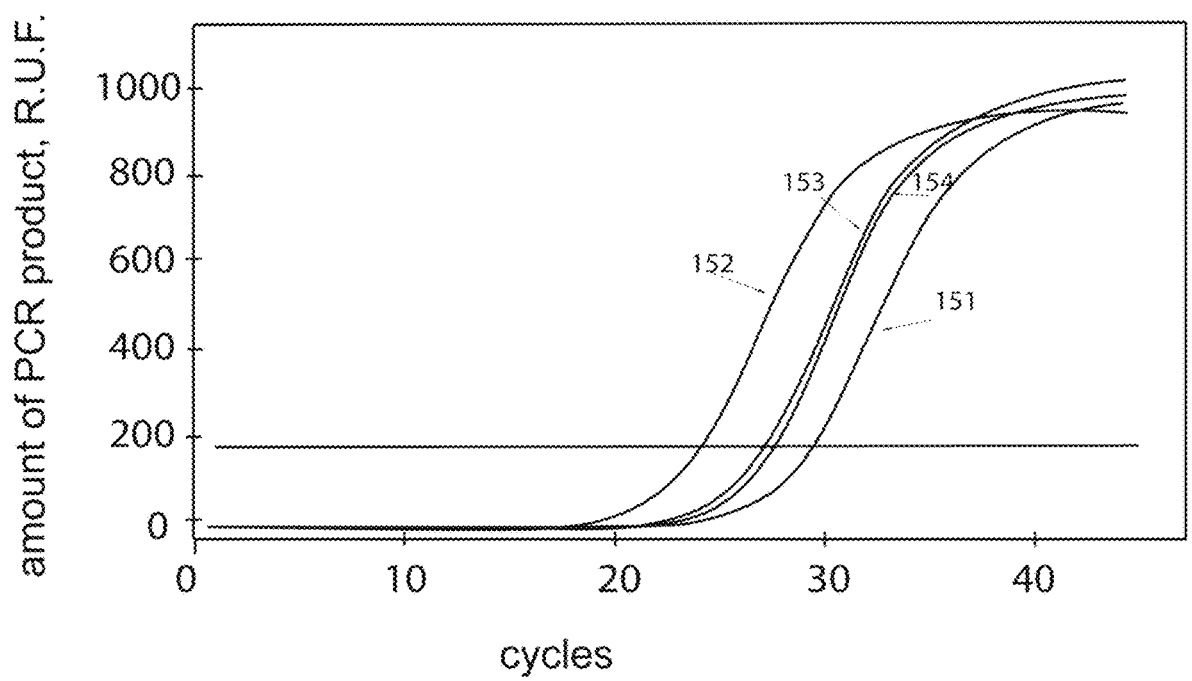

FIG. 15 shows diagrams of cDNA amplicon accumulation of the TIMP2 therapeutic gene in bovine dermal fibroblast cells (ScienCell, Cat. #B2300) before and 48 hours after transfection of these cells with the DNA vector VTvaf17-TIMP2 in order to demonstrate the method of use by injecting the gene therapy DNA vector in animals.

Curves of accumulation of amplicons during the reaction are shown in FIG. 15 corresponding to:
151—cDNA of TIMP2 gene in bovine dermal fibroblast cells before transfection with gene therapy DNA vector VTvaf17-TIMP2,
152—cDNA of TIMP2 gene in bovine dermal fibroblast cells after transfection with gene therapy DNA vector VTvaf17-TIMP2,
153—cDNA of ACT gene in bovine dermal fibroblast cells before transfection with gene therapy DNA vector VTvaf17-TIMP2,
154—cDNA of ACT gene in bovine dermal fibroblast cells after transfection with gene therapy DNA vector VTvaf17-TIMP2.

Bull/cow actin gene (ACT) listed in the GenBank database under number AH001130.2 was used as a reference gene.

EMBODIMENT OF THE INVENTION

Gene therapy DNA vectors carrying the human therapeutic genes designed to increase the expression level of these therapeutic genes in human and animal tissues were constructed based on 3165 bp DNA vector VTvaf17. The method of production of each gene therapy DNA vector carrying the therapeutic genes is to clone the protein coding sequence of the therapeutic gene selected from the group of the following genes: human SKI gene (encodes SKI protein), human TGFB3 gene (encodes TGFB3 protein), human TIMP2 gene (encodes TIMP2 protein), human FMOD gene (encodes FMOD protein) to the polylinker of gene therapy DNA vector VTvaf17. It is known that the ability of DNA vectors to penetrate into eukaryotic cells is due mainly to the vector size. DNA vectors with the smallest size have higher penetration capability. Thus, the absence of elements in the vector that bear no functional load, but at the same time increase the vector DNA size is preferred. These features of DNA vectors were taken into account during the production of gene therapy DNA vectors based on gene therapy DNA vector VTvaf17 carrying the therapeutic gene selected from the group of SKI, TGFB3, TIMP2, and FMOD genes with no large non-functional sequences and antibiotic resistance genes in the vector, which, in addition to technological advantages and safe use, allowed for the significant reduction of size of the produced gene therapy DNA vector VTvaf17 carrying the therapeutic gene selected from the group of SKI, TGFB3, TIMP2, and FMOD genes. Thus, the ability of the obtained gene therapy DNA vector to penetrate into eukaryotic cells is due to its small length.

Each of the following gene therapy DNA vectors: DNA vector VTvaf17-SKI, or VTvaf17-TGFB3, or VTvaf17-TIMP2, or VTvaf17-FMOD was produced as follows: the coding region of the therapeutic gene from the group of SKI, or TGFB3, or TIMP2, or FMOD genes was cloned to gene therapy DNA vector VTvaf17 and gene therapy DNA vector VTvaf17-SKI, SEQ ID NO: 1, or VTvaf17-TGFB3, SEQ ID NO: 2, or VTvaf17-TIMP2, SEQ ID NO: 3, or VTvaf17-FMOD, SEQ ID NO: 4, respectively, was obtained. The coding region of SKI gene (2228 bp), or TGFB3 gene (1252 bp), or TIMP2 gene (704 bp), or FMOD gene (1146 bp) was produced by extracting total RNA from the biological normal human tissue sample. The reverse transcription reaction was used for the synthesis of the first chain cDNA of human SKI, TGFB3, TIMP2, and FMOD genes. Amplification was performed using oligonucleotides produced for this purpose by the chemical synthesis method. The amplification product was cleaved by specific restriction endonucleases taking into account the optimal procedure for further cloning, and cloning to the gene therapy DNA vector VTvaf17 was performed by BamHI, EcoRI, and HindIII restriction sites located in the VTvaf17 vector polylinker. The selection of restriction sites was carried out in such a way that the cloned fragment entered the reading frame of expression cassette of the vector VTvaf17, while the protein coding sequence did not contain restriction sites for the selected endonucleases. Experts in this field realise that the methodological implementation of gene therapy DNA vector VTvaf17-SKI, or VTvaf17-TGFB3, or VTvaf17-TIMP2, or VTvaf17-FMOD production can vary within the framework of the selection of known methods of molecular gene cloning and these methods are included in the scope of this invention. For example, different oligonucleotide sequences can be used to amplify SKI, or TGFB3, or TIMP2, or FMOD gene, different restriction endonucleases or laboratory techniques, such as ligation independent cloning of genes.

Gene therapy DNA vector VTvaf17-SKI, or VTvaf17-TGFB3, or VTvaf17-TIMP2, or VTvaf17-FMOD has the nucleotide sequence SEQ ID NO: 1, or SEQ ID NO: 2, or SEQ ID NO: 3, or SEQ ID NO: 4, respectively. At the same time, degeneracy of genetic code is known to the experts in this field and means that the scope of this invention also includes variants of nucleotide sequences differing by insertion, deletion, or replacement of nucleotides that do not result in a change in the polypeptide sequence encoded by the therapeutic gene, and/or do not result in a loss of functional activity of the regulatory elements of VTvaf17 vector. At the same time, genetic polymorphism is known to the experts in this field and means that the scope of this invention also includes variants of nucleotide sequences of genes from the group of SKI, TGFB3, TIMP2, and FMOD genes that also encode different variants of the amino acid sequences of SKI, TGFB3, TIMP2, and FMOD proteins that do not differ from those listed in their functional activity under physiological conditions.

The ability to penetrate into eukaryotic cells and express functional activity, i.e. the ability to express the therapeutic gene of the obtained gene therapy DNA vector VTvaf17-SKI, or VTvaf17-TGFB3, or VTvaf17-TIMP2, or VTvaf17-FMOD is confirmed by introducing the obtained vector into eukaryotic cells and subsequent analysis of the expression of specific mRNA and/or protein product of the therapeutic gene. The presence of specific mRNA in cells into which the gene therapy DNA vector VTvaf17-SKI, or VTvaf17-TGFB3, or VTvaf17-TIMP2, or VTvaf17-FMOD was introduced shows the ability of the obtained vector to both penetrate into eukaryotic cells and express mRNA of the therapeutic gene. Furthermore, it is known to the experts in this field that the presence of mRNA gene is a mandatory condition, but not an evidence of the translation of protein encoded by the therapeutic gene. Therefore, in order to confirm properties of the gene therapy DNA vector VTvaf17-SKI, or VTvaf17-TGFB3, or VTvaf17-TIMP2, or VTvaf17-FMOD to express the therapeutic gene at the protein level in eukaryotic cells into which the gene therapy DNA vector was introduced, analysis of the concentration of proteins encoded by the therapeutic genes was carried out using immunological methods. The presence of SKI, or TGFB3, or TIMP2, or FMOD protein confirms the efficiency of expression of therapeutic genes in eukaryotic cells and the possibility of increasing the protein concentration using the gene therapy DNA vector based on gene therapy DNA vector VTvaf17 carrying the therapeutic gene selected from the group of SKI, TGFB3, TIMP2, and FMOD genes. Thus in order to confirm the expression efficiency of the constructed gene therapy DNA vector VTvaf17-SKI carrying the therapeutic gene, namely the SKI gene, gene therapy DNA vector VTvaf17-TGFB3 carrying the therapeutic gene, namely the TGFB3 gene, gene therapy DNA vector VTvaf17-TIMP2 carrying the therapeutic gene, namely the TIMP2 gene, gene therapy DNA vector VTvaf17-FMOD carrying the therapeutic gene, namely the FMOD gene the following methods were used:

A) real-time PCR, i.e. change in mRNA accumulation of therapeutic genes in human and animal cell lysate after transfection of different human and animal cell lines with gene therapy DNA vectors, B) Enzyme-linked immunosorbent assay, i.e. change in the quantitative level of therapeutic proteins in the human cell lysate after transfection of different human cell lines with gene therapy DNA vectors, C) Enzyme-linked immunosorbent assay, i.e. change in the quantitative level of therapeutic proteins in the supernatant of human and animals tissue biopsy specimens after the injection of gene therapy DNA vectors into these tissues, D) Enzyme-linked immunosorbent assay, i.e. change in the quantitative level of therapeutic proteins in the supernatant of human tissue biopsies after the injection of these tissues with autologous cells of this human transfected with gene therapy DNA vectors.

In order to confirm the practicability of use of the constructed gene therapy DNA vector VTvaf17-SKI carrying the therapeutic gene, namely the SKI gene, gene therapy DNA vector VTvaf17-TGFB3 carrying the therapeutic gene, namely the TGFB3 gene, gene therapy DNA vector VTvaf17-TIMP2 carrying the therapeutic gene, namely the TIMP2 gene, gene therapy DNA vector VTvaf17-FMOD carrying the therapeutic gene, namely the FMOD gene, the following was performed:

A) transfection of different human and animal cell lines with gene therapy DNA vectors, B) injection of gene therapy DNA vectors into different human and animal tissues, C) injection of a mixture of gene therapy DNA vectors into animal tissues, D) injection of autologous cells transfected with gene therapy DNA vectors into human tissues.

These methods of use lack potential risks for gene therapy of humans and animals due to the absence of regulatory elements in the gene therapy DNA vector that constitute the nucleotide sequences of viral genomes and absence of antibiotic resistance genes in the gene therapy DNA vector as confirmed by the lack of regions homologous to the viral genomes and antibiotic resistance genes in the nucleotide sequences of gene therapy DNA vector VTvaf17-SKI, or gene therapy DNA VTvaf17-TGFB3, or gene therapy DNA vector VTvaf17-TIMP2, or gene therapy DNA vector VTvaf17-FMOD (SEQ ID NO: 1, or SEQ ID NO: 2, or SEQ ID NO: 3, or SEQ ID NO: 4, respectively).

It is known to the experts in this field that antibiotic resistance genes in the gene therapy DNA vectors are used to obtain these vectors in preparative quantities by increasing bacterial biomass in a nutrient medium containing a selective antibiotic. Within the framework of this invention, in order to ensure the safe use of gene therapy DNA vector VTvaf17 carrying SKI, or TGFB3, or TIMP2, or FMOD therapeutic genes, the use of selective nutrient media containing an antibiotic is not possible. A method for obtaining strains for production of these gene therapy vectors based on *Escherichia coli* strain SCS110-AF is proposed as a technological solution for obtaining the gene therapy DNA vector VTvaf17 carrying a therapeutic gene selected from the group of SKI, TGFB3, TIMP2, and FMOD genes in order to scale up the production of gene therapy vectors to an industrial scale. The method of *Escherichia coli* strain SCS110-AF/VTvaf17-SKI, or *Escherichia coli* strain SCS110-AF/VTvaf17-TGFB3, or *Escherichia coli* strain SCS110-AF/VTvaf17-TIMP2, or *Escherichia coli* strain SCS110-AF/VTvaf17-FMOD production involves production of competent cells of *Escherichia coli* strain SCS110-AF with the injection of gene therapy DNA vector VTvaf17-SKI, or DNA vector VTvaf17-TGFB3, or DNA vector VTvaf17-TIMP2, or DNA vector VTvaf17-FMOD into these cells, respectively, using transformation (electroporation) methods well-known to the experts in this field. The obtained *Escherichia coli* strain SCS110-AF/VTvaf17-SKI, or *Escherichia coli* strain SCS110-AF/VTvaf17-TGFB3, or *Escherichia coli* strain SCS110-AF/VTvaf17-TIMP2, or *Escherichia coli* strain SCS110-AF/VTvaf17-FMOD is used to produce the gene therapy DNA vector VTvaf17-SKI, or VTvaf17-TGFB3, or VTvaf17-TIMP2, or VTvaf17-FMOD, respectively, allowing for the use of antibiotic-free media.

In order to confirm the production of *Escherichia coli* strain SCS110-AF/VTvaf17-SKI, or *Escherichia coli* strain SCS110-AF/VTvaf17-TGFB3, or *Escherichia coli* strain SCS110-AF/VTvaf17-TIMP2, or *Escherichia coli* strain SCS110-AF/VTvaf17-FMOD, transformation, selection, and subsequent biomass growth with extraction of plasmid DNA were performed.

To confirm the producibility and constructability and scale up of the production of gene therapy DNA vector VTvaf17-SKI carrying the therapeutic gene, namely SKI gene, gene therapy DNA vector VTvaf17-TGFB3 carrying the therapeutic gene, namely TGFB3 gene, gene therapy DNA vector VTvaf17-TIMP2 carrying the therapeutic gene, namely TIMP2 gene, gene therapy DNA vector VTvaf17-FMOD carrying the therapeutic gene, namely FMOD gene, to an industrial scale, the fermentation on an industrial scale of *Escherichia coli* strain SCS110-AF/VTvaf17-SKI, or *Escherichia coli* strain SCS110-AF/VTvaf17-TGFB3, or *Escherichia coli* strain SCS110-AF/VTvaf17-TIMP2, or *Escherichia coli* strain SCS110-AF/VTvaf17-FMOD each containing gene therapy DNA vector VTvaf17 carrying the therapeutic gene, namely SKI, or TGFB3, or TIMP2, or FMOD gene was performed.

The method of scaling the production of bacterial mass to an industrial scale for the isolation of gene therapy DNA vector VTvaf17 carrying the therapeutic gene selected from the group of SKI, TGFB3, TIMP2, and FMOD genes involves incubation of the seed culture of *Escherichia coli* strain SCS110-AF/VTvaf17-SKI, or *Escherichia coli* strain SCS110-AF/VTvaf17-TGFB3 strain, or *Escherichia coli* strain SCS110-AF/VTvaf17-TIMP2 strain, or *Escherichia coli* strain SCS110-AF/VTvaf17-FMOD in the antibiotic-free nutrient medium that provides suitable biomass accumulation dynamics. Upon reaching a sufficient amount of biomass in the logarithmic phase, the bacterial culture is transferred to an industrial fermenter and then grown to a stationary phase, then the fraction containing the therapeutic DNA product, i.e. gene therapy DNA vector VTvaf17-SKI, or gene therapy DNA vector VTvaf17-TGFB3, or gene therapy DNA vector VTvaf17-TIMP2, or gene therapy DNA vector VTvaf17-FMOD, is extracted, multi-stage filtered, and purified by chromatographic methods. It is known to the experts in this field that culture conditions of strains, composition of nutrient media (except for antibiotic-free), equipment used, and DNA purification methods may vary within the framework of standard operating procedures depending on the particular production line, but known approaches to scaling, industrial production, and purification of DNA vectors using *Escherichia coli* strain SCS110-AF/VTvaf17-SKI, or *Escherichia coli* strain SCS110-AF/VTvaf17-TGFB3, or *Escherichia coli* strain SCS110-AF/VTvaf17-TIMP2, or *Escherichia coli* strain SCS110-AF/VTvaf17-FMOD fall within the scope of this invention.

The described disclosure of the invention is illustrated by examples of the embodiment of this invention.

The essence of the invention is explained in the following examples.

Example 1

Production of gene therapy DNA vector VTvaf17-SKI carrying the therapeutic gene, namely the SKI gene.

Gene therapy DNA vector VTvaf17-SKI was constructed by cloning the coding region of SKI gene (2228 bp) to a 3165 bp DNA vector VTvaf17 by BamHI and HindIII restriction sites. The coding region of SKI gene (2228 bp) was obtained by isolating total RNA from the biological human tissue sample followed by reverse transcription reaction using commercial kit Mint-2 (Evrogen, Russia) and PCR amplification using the following oligonucleotides:

SKI_F CAGGATCCGCGGGAGCGGCCGGGGGAG,
SKI_R TATAAGCTTACGGCTCCAGCTCCGCAG
and commercially available kit Phusion® High-Fidelity DNA Polymerase (New England Biolabs, USA).

Gene therapy DNA vector VTvaf17 was constructed by consolidating six fragments of DNA derived from different sources:

(a) the origin of replication was produced by PCR amplification of a region of commercially available plasmid pBR322 with a point mutation,
(b) EF1a promoter region was produced by PCR amplification of a site of human genomic DNA,
(c) hGH-TA transcription terminator was produced by PCR amplification of a site of human genomic DNA,
(d) the RNA-OUT regulatory site of transposon Tn10 was synthesised from oligonucleotides,
(e) kanamycin resistance gene was produced by PCR amplification of a site of commercially available human plasmid pET-28,
(f) the polylinker was produced by annealing two synthetic oligonucleotides.

PCR amplification was performed using the commercially available kit Phusion® High-Fidelity DNA Polymerase (New England Biolabs, USA) as per the manufacturer's instructions. The fragments have overlapping regions allowing for their consolidation with subsequent PCR amplification. Fragments (a) and (b) were consolidated using oligonucleotides Ori-F and EF1-R, and fragments (c), (d), and (e) were consolidated using oligonucleotides hGH-F and Kan-R. Afterwards, the produced fragments were consolidated by restriction with subsequent ligation by sites BamHI and NcoI. This resulted in a plasmid still devoid of the polylinker. To add it, the plasmid was cleaved by BamHI and EcoRI sites followed by ligation with fragment (f). Therefore, a vector was constructed carrying the kanamycin resistance gene flanked by SpeI restriction sites. Then this gene was cleaved by SpeI restriction sites and the remaining fragment was ligated to itself. This resulted in a 3165 bp gene therapy DNA vector VTvaf17 that is recombinant and allows for antibiotic-free selection.

The amplification product of the coding region of SKI gene and DNA vector VTvaf17 was cleaved by BamHI and HindIII restriction endonucleases (New England Biolabs, USA).

Figure 1A:
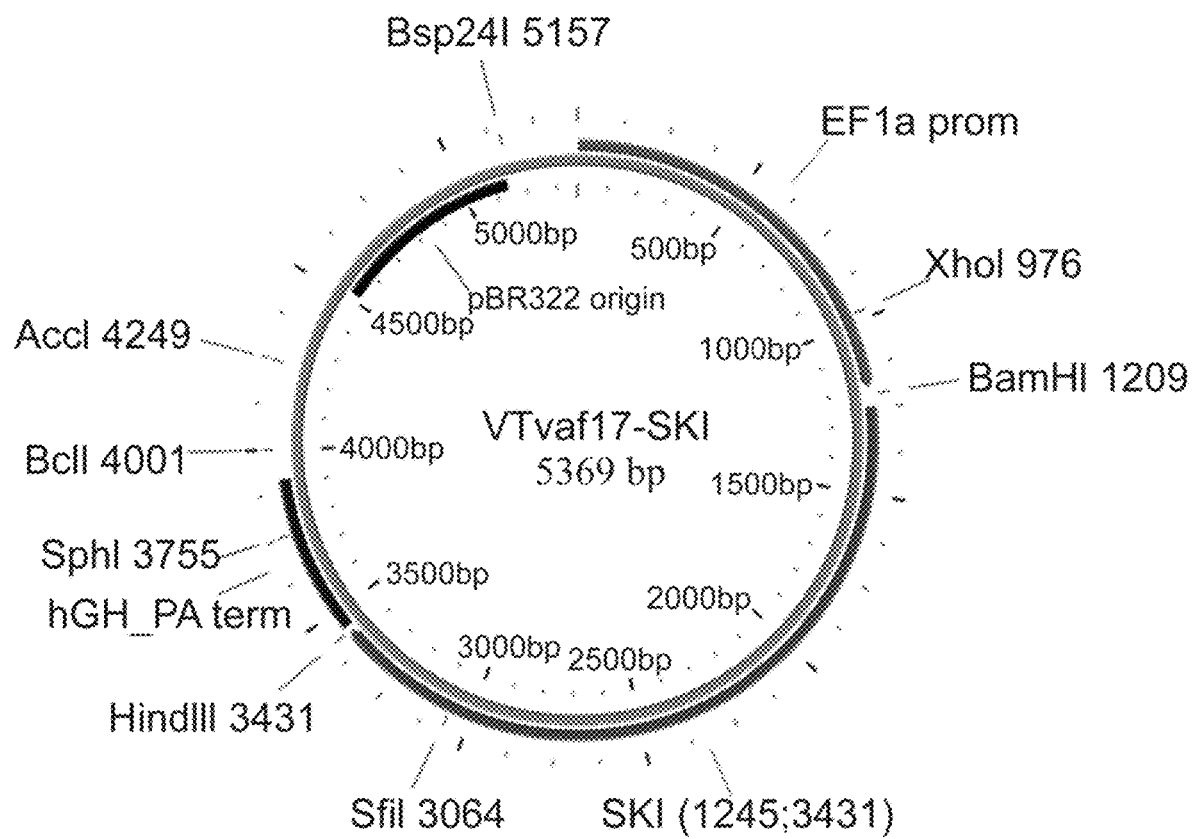
FIGS. 1A-1D show the structure of gene therapy DNA vector VTvaf17 carrying the therapeutic gene selected from the group of SKI, TGFB3, TIMP2, and FMOD genes that constitutes a circular double-stranded DNA molecule capable of autonomous replication in *Escherichia coli* cells.

This resulted in a 5369 bp DNA vector VTvaf17-SKI with the nucleotide sequence SEQ ID NO: 1 and general structure shown in FIG. 1A.

Example 2

Production of gene therapy DNA vector VTvaf17-TGFB3 carrying the therapeutic gene, namely the TGFB3 gene.

Gene therapy DNA vector VTvaf17-TGFB3 was constructed by cloning the coding region of TGFB3 gene (1252 bp) to a 3165 bp DNA vector VTvaf17 by BamHI and HindIII restriction sites. The coding region of TGFB3 gene (1252 bp) was obtained by isolating total RNA from the biological human tissue sample followed by reverse transcription reaction using commercial kit Mint-2 (Evrogen, Russia) and PCR amplification using the following oligonucleotides:

TGFB3_F GGATCCACCATGAAGATGCACTTGCAAAGG,
TGFB3_R TATAAGCTTAGCTACATTTACAAGACTTCACCA and commercially available kit Phusion® High-Fidelity DNA Polymerase (New England Biolabs, USA); amplification product and DNA vector VTvaf17 were cleaved by restriction endonucleases BamHI and HindIII (New England Biolabs, USA).

Figure 1B:
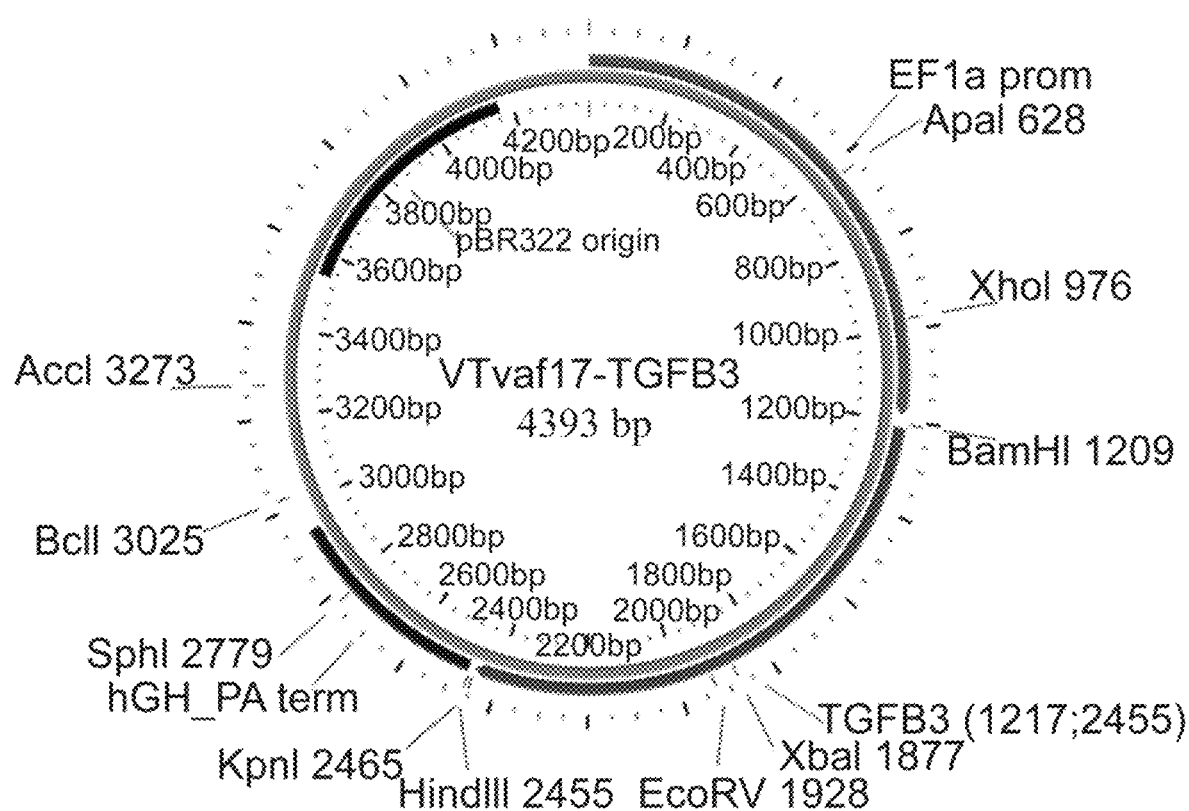

This resulted in a 4393 bp DNA vector VTvaf17-TGFB3 with the nucleotide sequence SEQ ID NO: 2 and general structure shown in FIG. 1B.

Gene therapy DNA vector VTvaf17 was constructed as described in Example 1.

Example 3

Production of gene therapy DNA vector VTvaf17-TIMP2 carrying the therapeutic gene, namely the human TIMP2 gene.

Gene therapy DNA vector VTvaf17-TIMP2 was constructed by cloning the coding region of TIMP2 gene (704 bp) to a 3165 bp DNA vector VTvaf17 by BamHI and HindIII restriction sites. The coding region of TIMP2 gene (704 bp) was obtained by isolating total RNA from the biological human tissue sample followed by reverse transcription reaction using commercial kit Mint-2 (Evrogen, Russia) and PCR amplification using the following oligonucleotides:

TIMP2_F CAGGATCCGGCCCCCGCCCGCCCAGC,
TIMP2_R TATAAGCTTATGGGTCCTCGATGTCGAGA and commercially available kit Phusion® High-Fidelity DNA Polymerase (New England Biolabs, USA); amplification product and DNA vector VTvaf17 were cleaved by restriction endonucleases BamHI and HindIII (New England Biolabs, USA).

Figure 1C:
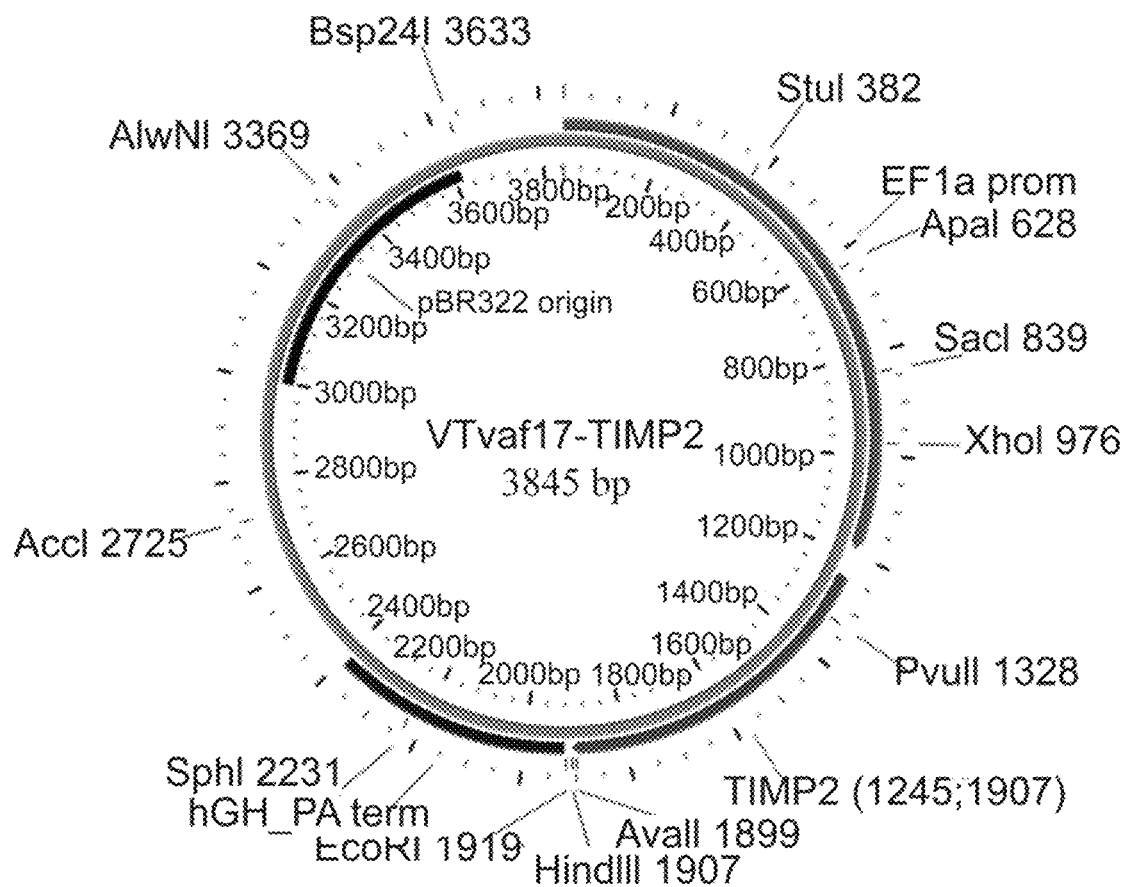

This resulted in a 3845 bp DNA vector VTvaf17-TIMP2 with the nucleotide sequence SEQ ID NO: 3 and general structure shown in FIG. 1C.

Gene therapy DNA vector VTvaf17 was constructed as described in Example 1.

Example 4

Production of gene therapy DNA vector VTvaf17-FMOD carrying the therapeutic gene, namely the FMOD gene.

Gene therapy DNA vector VTvaf17-FMOD was constructed by cloning the coding region of FMOD gene (1146 bp) to a 3165 bp DNA vector VTvaf17 by BamHII and EcoRI restriction sites. The coding region of FMOD gene (1146 bp) was obtained by isolating total RNA from the biological human tissue sample followed by reverse transcription reaction using commercial kit Mint-2 (Evrogen) and PCR amplification using the following oligonucleotides:

FMOD_F GGATCCACCATGCAGTGGACCTCCCTCCT,
FMOD_R TATGAATTCTTAGATCTCGATGAGGCTGGCA and commercially available kit Phusion® High-Fidelity DNA Polymerase (New England Biolabs, USA); amplification product and DNA vector VTvaf17 were cleaved by restriction endonucleases BamHII and EcoRI (New England Biolabs, USA).

Figure 1D:
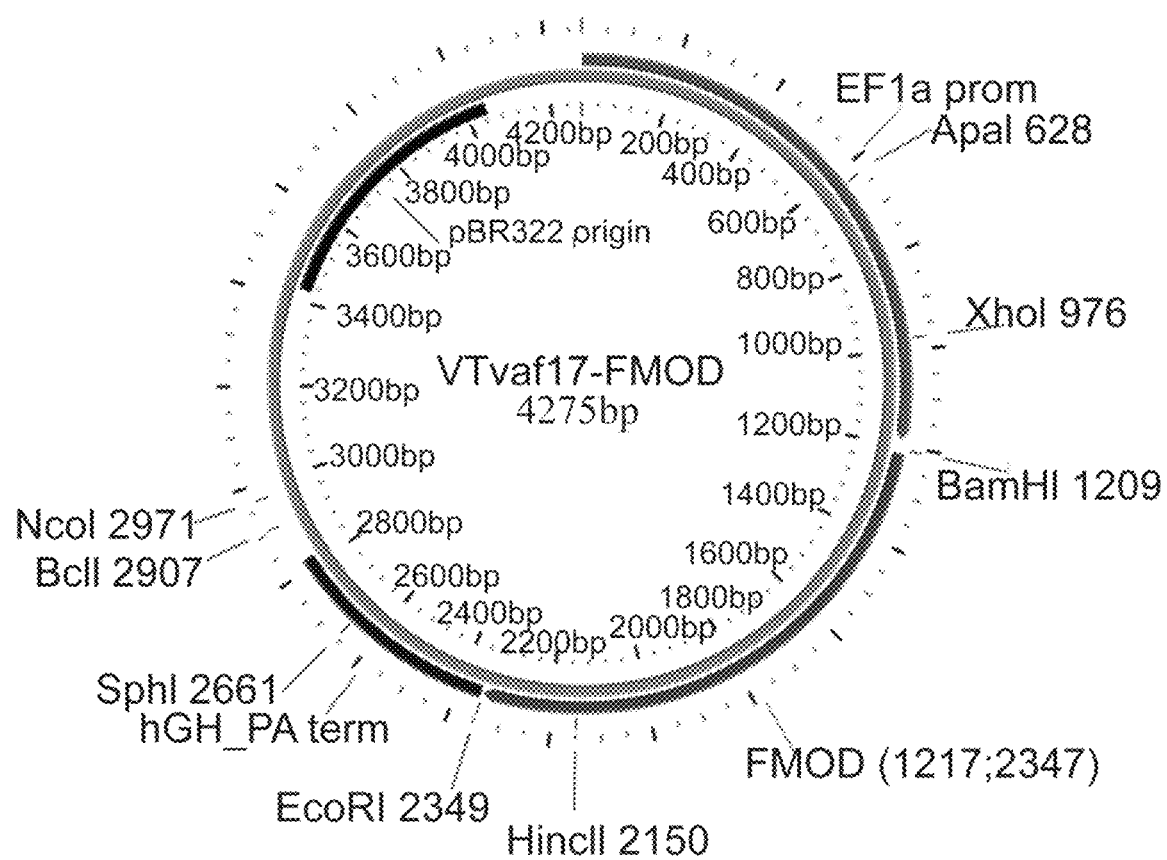

This resulted in a 4275 bp DNA vector VTvaf17-FMOD with the nucleotide sequence SEQ ID NO: 4 and general structure shown in FIG. 1D.

Gene therapy DNA vector VTvaf17 was constructed as described in Example 1.

Example 5

Proof of the ability of gene therapy DNA vector VTvaf17-SKI carrying the therapeutic gene, namely SKI gene, to penetrate eukaryotic cells and its functional activity at the level of therapeutic gene mRNA expression. This example also demonstrates practicability of use of gene therapy DNA vector carrying the therapeutic gene.

Changes in the mRNA accumulation of the SKI therapeutic gene were assessed in HDFa primary human dermal fibroblast cell culture (ATCC PCS-201-01) 48 hours after its transfection with gene therapy DNA vector VTvaf17-SKI carrying the human SKI gene. The amount of mRNA was determined by the dynamics of accumulation of cDNA amplicons in the real-time PCR.

HDFa primary human dermal fibroblast cell culture was used for the assessment of changes in the therapeutic SKI mRNA accumulation. HDFa cell culture was grown under standard conditions (37° C., 5% CO2) using the Fibroblast Growth Kit-Serum-Free (ATCC® PCS-201-040). The growth medium was replaced every 48 hours during the cultivation process.

To achieve 90% confluence, 24 hours before the transfection procedure, the cells were seeded into a 24-well plate in the quantity of $5 \times 10^4$ cells per well. Transfection with gene therapy DNA vector VTvaf17-SKI expressing the human SKI gene was performed using Lipofectamine 3000 (ThermoFisher Scientific, USA) according to the manufacturer's recommendations. In test tube 1, 1 µl of DNA vector VTvaf17-SKI solution (concentration 500 ng/µl) and 1 µl of reagent P3000 was added to 25 µl of medium Opti-MEM (Gibco, USA). The preparation was mixed by gentle shaking. In test tube 2, 1 µl of Lipofectamine 3000 solution was added to 25 µl of medium Opti-MEM (Gibco, USA). The preparation was mixed by gentle shaking. The contents from test tube 1 were added to the contents of test tube 2, and the mixture was incubated at room temperature for 5 minutes. The resulting solution was added dropwise to the cells in the volume of 40 µl.

HDFa cells transfected with the gene therapy DNA vector VTvaf17 devoid of the inserted therapeutic gene (cDNA of SKI gene before and after transfection with gene therapy DNA vector VTvaf17 devoid of the inserted therapeutic gene is not shown in the figures) were used as a reference. Reference vector VTvaf17 for transfection was prepared as described above.

Total RNA from HDFa cells was extracted using Trizol Reagent (Invitrogen, USA) according to the manufacturer's recommendations. 1 ml of Trizol Reagent was added to the well with cells and homogenised and heated for 5 minutes at 65° C. Then the sample was centrifuged at 14,000 g for 10 minutes and heated again for 10 minutes at 65° C. Then 200 µl of chloroform was added, and the mixture was gently stirred and centrifuged at 14,000 g for 10 minutes. Then the water phase was isolated and mixed with ⅒ of the volume of 3M sodium acetate, pH 5.2, and an equal volume of isopropyl alcohol. The sample was incubated at −20° C. for 10 minutes and then centrifuged at 14,000 g for 10 minutes. The precipitated RNA were rinsed in 1 ml of 70% ethyl alcohol, air-dried and dissolved in 10 µl of RNase-free water. The level of SKI mRNA expression after transfection was determined by assessing the dynamics of the accumulation of cDNA amplicons by real-time PCR. For the production and amplification of cDNA specific for the human SKI gene, the following SKI_SF and SKI_SR oligonucleotides were used:

SKI_SF TGGACACCAAGGAAGCCAAAG,
SKI_SR GCTGTTCCTGCAGCTCCTTCAC.

The length of amplification product is 468 bp.

Reverse transcription reaction and PCR amplification was performed using SYBR GreenQuantitect RT-PCR Kit (Qiagen, USA) for real-time PCR.

The reaction was carried out in a volume of 20 µl, containing: 25 µl of QuantiTect SYBR Green RT-PCR Master Mix, 2.5 mM of magnesium chloride, 0.5 µM of each primer, and 5 µl of RNA. For the reaction, CFX96 amplifier (Bio-Rad, USA) was used under the following conditions: 1 cycle of reverse transcription at 42° C. for 30 minutes, denaturation at 98° C. for 15 minutes, followed by 40 cycles comprising denaturation at 94° C. for 15 s, annealing of primers at 60° C. for 30 s and elongation at 72° C. for 30 s. B2M (beta-2-microglobuline) gene listed in the GenBank database under number NM 004048.2 was used as a reference gene. Positive control included amplicons from PCR on matrices represented by plasmids in known concentrations containing cDNA sequences of SKI and B2M genes. Negative control included deionised water. Real-time quantification of the dynamics of accumulation of cDNA amplicons of SKI and B2M genes was conducted using the Bio-Rad CFX Manager 2.1 software (Bio-Rad, USA). Diagrams resulting from the assay are shown in FIG. 2.

FIG. 2 shows that the level of specific mRNA of human SKI gene has grown massively as a result of transfection of HDFa primary human fibroblast cell culture with gene therapy DNA vector VTvaf17-SKI, which confirms the ability of the vector to penetrate eukaryotic cells and express the SKI gene at the mRNA level. The presented results also confirm the practicability of use of gene therapy DNA vector VTvaf17-SKI in order to increase the expression level of SKI gene in eukaryotic cells.

Example 6

Proof of the ability of gene therapy DNA vector VTvaf17-TGFB3 carrying the therapeutic gene, namely TGFB3 gene, to penetrate eukaryotic cells and its functional activity at the level of therapeutic gene mRNA expression. This example also demonstrates practicability of use of gene therapy DNA vector carrying the therapeutic gene.

Changes in the mRNA accumulation of the TGFB3 therapeutic gene were assessed in HEKa primary human epidermal keratinocyte cell culture (ATCC PCS-200-011) 48 hours after its transfection with gene therapy DNA vector VTvaf17-TGFB3 carrying the human TGFB3 gene. The amount of mRNA was determined by the dynamics of accumulation of cDNA amplicons in the real-time PCR.

HEKa primary human epidermal keratinocyte cell culture was grown in Keratinocyte Growth Kit (ATCC® PCS-200-040™) under standard conditions (37° C., 5% CO2). To achieve 90% confluence, 24 hours before the transfection procedure, the cells were seeded into a 24-well plate in the quantity of $5 \times 10^4$ cells per well. Lipofectamine 3000 (ThermoFisher Scientific, USA) was used as a transfection reagent. The transfection with gene therapy DNA vector VTvaf17-TGFB3 expressing the human TGFB3 gene was performed according to the procedure described in Example 5. B2M (beta-2-microglobuline) gene listed in the GenBank database under number NM 004048.2 was used as a reference gene. HEKa cell culture transfected with the gene therapy DNA vector VTvaf17 devoid of the therapeutic gene (cDNA of TGFB3 gene before and after transfection with gene therapy DNA vector VTvaf17 devoid of the inserted therapeutic gene is not shown in the figures) was used as a reference. RNA isolation, reverse transcription reaction, and real-time PCR were performed as described in Example 5, except for oligonucleotides with sequences different from Example 5. For the amplification of cDNA specific for the human TGFB3 gene, the following TGFB3_SF and TGFB3_SR oligonucleotides were used:

TGFB3_SF TGAGCACATTGCCAAACAGC,
TGFB3_SR GAGGCAGATGCTTCAGGGTT.

The length of amplification product is 594 bp.

Positive control included amplicons from PCR on matrices represented by plasmids in known concentrations containing cDNA sequences of TGFB3 and B2M genes. Negative control included deionised water. Real-time quantification of the PCR products, i.e. TGFB3 and B2M gene cDNAs obtained by amplification, was conducted using the Bio-Rad CFX Manager 2.1 software (Bio-Rad, USA). Diagrams resulting from the assay are shown in FIG. 3.

FIG. 3 shows that the level of specific mRNA of human TGFB3 gene has grown massively as a result of transfection of HEKa cell culture with gene therapy DNA vector VTvaf17-TGFB3, which confirms the ability of the vector to penetrate eukaryotic cells and express the TGFB3 gene at the mRNA level. The presented results also confirm the practicability of use of gene therapy DNA vector VTvaf17-TGFB3 in order to increase the expression level of TGFB3 gene in eukaryotic cells.

Example 7

Proof of the ability of gene therapy DNA vector VTvaf17-TIMP2 carrying the therapeutic gene, namely TIMP2 gene, to penetrate eukaryotic cells and its functional activity at the level of therapeutic gene mRNA expression. This example also demonstrates practicability of use of gene therapy DNA vector carrying the therapeutic gene.

Changes in the mRNA accumulation of the TIMP2 therapeutic gene were assessed in Hs27 human foreskin fibroblast cell line (ATCC CRL-1634) 48 hours after its transfection with gene therapy DNA vector VTvaf17-TIMP2 carrying the human TIMP2 gene. The amount of mRNA was determined by the dynamics of accumulation of cDNA amplicons in the real-time PCR.

Hs27 human foreskin fibroblast cell line was grown in Dulbecco's Modified Eagle's Medium (DMEM) (ATCC® 30-2020™) with the addition of 10% of bovine serum (ATCC® 30-2020™) under standard conditions (37° C., 5% $CO_2$). To achieve 90% confluence, 24 hours before the transfection procedure, the cells were seeded into a 24-well plate in the quantity of $5 \times 10^4$ cells per well. Lipofectamine 3000 (ThermoFisher Scientific, USA) was used as a transfection reagent. The transfection with gene therapy DNA vector VTvaf17-TIMP2 expressing the human TIMP2 gene was performed according to the procedure described in Example 5. B2M (beta-2-microglobuline) gene listed in the GenBank database under number NM 004048.2 was used as a reference gene. Hs27 cell line transfected with the gene therapy DNA vector VTvaf17 devoid of the therapeutic gene (cDNA of TIMP2 gene before and after transfection with gene therapy DNA vector VTvaf17 devoid of the inserted therapeutic gene is not shown in the figures) was used as a reference. RNA isolation, reverse transcription reaction, and real-time PCR were performed as described in Example 5, except for oligonucleotides with sequences different from Example 5. For the amplification of cDNA specific for the human TIMP2 gene, the following TIMP2_SF and TIMP2_SR oligonucleotides were used:

TIMP2_SF GCAACAGGCGTTTTGCAATG,
TIMP2_SR AGGGCACGATGAAGTCACAG

The length of amplification product is 296 bp.

Positive control included amplicons from PCR on matrices represented by plasmids in known concentrations containing cDNA sequences of TIMP2 and B2M genes. Negative control included deionised water. Real-time quantification of the PCR products, i.e. TIMP2 and B2M gene cDNAs obtained by amplification, was conducted using the Bio-Rad CFX Manager 2.1 software (Bio-Rad, USA). Diagrams resulting from the assay are shown in FIG. 4.

FIG. 4 shows that the level of specific mRNA of human TIMP2 gene has grown massively as a result of transfection of Hs27 human foreskin fibroblast cell line with gene therapy DNA vector VTvaf17-TIMP2, which confirms the ability of the vector to penetrate eukaryotic cells and express the TIMP2 gene at the mRNA level. The presented results also confirm the practicability of use of gene therapy DNA vector VTvaf17-TIMP2 in order to increase the expression level of TIMP2 gene in eukaryotic cells.

Example 8

Proof of the ability of gene therapy DNA vector VTvaf17-FMOD carrying the therapeutic gene, namely FMOD gene, to penetrate eukaryotic cells and its functional activity at the level of therapeutic gene mRNA expression. This example also demonstrates practicability of use of gene therapy DNA vector carrying the therapeutic gene.

Changes in the mRNA accumulation of the therapeutic FMOD gene were assessed in HMEC-1 human dermal microvascular endothelial cell line (ATCC CRL-3243) 48 hours after its transfection with gene therapy DNA vector VTvaf17-FMOD carrying the human FMOD gene. The amount of mRNA was determined by the dynamics of accumulation of cDNA amplicons in the real-time PCR.

HMEC-1 human dermal microvascular endothelial cell culture was grown in MCDB131 medium (Gibco™, Cat. 10372019) without glutamine and with the addition of 10 ng/ml of recombinant EGF (Sigma, E9644, USA), 10 mM glutamine (Paneco, Russia), 1 μg/ml hydrocortisone (Sigma H0888, USA), 10% HyClone™ Fetal Bovine Serum (Hyclone Laboratories Inc SH30068.03H1, USA) under standard conditions (37° C., 5% $CO_2$). To achieve 90% confluence, 24 hours before the transfection procedure, the cells were seeded into a 24-well plate in the quantity of $5 \times 10^4$ cells per well. Lipofectamine 3000 (ThermoFisher Scientific, USA) was used as a transfection reagent. The transfection with gene therapy DNA vector VTvaf17-FMOD expressing the human FMOD gene was performed according to the procedure described in Example 5. HMEC-1 cell culture transfected with the gene therapy DNA vector VTvaf17 devoid of the therapeutic gene (cDNA of FMOD gene before and after transfection with gene therapy DNA vector VTvaf17 devoid of the inserted therapeutic gene is not shown in the figures) was used as a reference. RNA isolation, reverse transcription reaction, and real-time PCR were performed as described in Example 5, except for oligonucleotides with sequences different from Example 5. For the amplification of cDNA specific for the human FMOD gene, the following FMOD_SF and FMOD_SR oligonucleotides were used:

FMOD_SF CCTACACCTACGGCTCTCCA,
FMOD_SR CATCCGGGTCAGGTTGTTGT

The length of amplification product is 326 bp.

Positive control included amplicons from PCR on matrices represented by plasmids in known concentrations containing cDNA sequences of FMOD and B2M genes. B2M (beta-2-microglobuline) gene listed in the GenBank database under number NM 004048.2 was used as a reference gene. Negative control included deionised water. Real-time quantification of the PCR products, i.e. FMOD and B2M gene cDNAs obtained by amplification, was conducted using the Bio-Rad CFX Manager 2.1 software (Bio-Rad, USA). Diagrams resulting from the assay are shown in FIG. 5.

FIG. 5 shows that the level of specific mRNA of human FMOD gene has grown massively as a result of transfection of HMEC-1 human dermal microvascular endothelial cell culture with gene therapy DNA vector VTvaf17-FMOD, which confirms the ability of the vector to penetrate eukaryotic cells and express the FMOD gene at the mRNA level. The presented results also confirm the practicability of use of gene therapy DNA vector VTvaf17-FMOD in order to increase the expression level of FMOD gene in eukaryotic cells.

Example 9

Proof of the efficiency and practicability of use of gene therapy DNA vector VTvaf17-SKI carrying the SKI gene in order to increase the expression of SKI protein in mammalian cells.

The change in the SKI protein concentration in the lysate of HDFa human dermal fibroblast (ATCC PCS-201-01) was assessed after transfection of these cells with DNA vector VTvaf17-SKI carrying the human SKI gene.

Human dermal fibroblast cell culture was grown as described in Example 5.

To achieve 90% confluence, 24 hours before the transfection procedure, the cells were seeded into a 24-well plate in the quantity of $5 \times 10^4$ cells per well. The 6th generation SuperFect Transfection Reagent (Qiagen, Germany) was used for transfection. The aqueous dendrimer solution without DNA vector (A) and DNA vector VTvaf17 devoid of cDNA of SKI gene (B) were used as a reference, and DNA vector VTvaf17-SKI carrying the human SKI gene was used as the transfected agent. The DNA-dendrimer complex was prepared according to the manufacturer's procedure (QIAGEN, SuperFect Transfection Reagent Handbook, 2002) with some modifications. For cell transfection in one well of a 24-well plate, the culture medium was added to 1 µg of DNA vector dissolved in TE buffer to a final volume of 60 µl, then 5 µl of SuperFect Transfection Reagent was added and gently mixed by pipetting five times. The complex was incubated at room temperature for 10-15 minutes. Then the culture medium was taken from the wells, the wells were rinsed with 1 ml of PBS buffer. 350 µl of medium containing 10 µg/ml of gentamicin was added to the resulting complex, mixed gently, and added to the cells. The cells were incubated with the complexes for 2-3 hours at 37° C. in the presence of 5% CO2.

The medium was then removed carefully, and the live cell array was rinsed with 1 ml of PBS buffer. Then, medium containing 10 µg/ml of gentamicin was added and incubated for 24-48 hours at 37° C. in the presence of 5% CO2.

After transfection, cells were rinsed three times with PBS, and then 1 ml of PBS was added to the cells and the cells were subjected to freezing/thawing three times. Then the suspension was centrifuged for 15 minutes at 15,000 rpm, and supernatant was collected and used for the quantification and assay of the therapeutic protein.

The SKI protein was assayed by enzyme-linked immunosorbent assay (ELISA) using the SKI ELISA Kit (Human) (Aviva Systems Biology Cat. OKCA01520, USA) according to the manufacturer's method with optical density detection using ChemWell Automated EIA and Chemistry Analyser (Awareness Technology Inc., USA).

To measure the numerical value of concentration, the calibration curve constructed using the reference samples from the kit with known concentrations of SKI protein was used. The sensitivity was at least 7.8 µg/ml, measurement range—from 31.25 µg/ml to 2000 µg/ml. R-3.0.2 was used for the statistical treatment of the results and data visualization (www.r-project.org/). Diagrams resulting from the assay are shown in FIG. 6.

FIG. 6 shows that the transfection of HDFa human dermal fibroblast cells with gene therapy DNA vector VTvaf17-SKI results in increased SKI protein concentration compared to reference samples, which confirms the ability of the vector to penetrate eukaryotic cells and express the SKI gene at the protein level. The presented results also confirm the practicability of use of gene therapy DNA vector VTvaf17-SKI in order to increase the expression level of SKI gene in eukaryotic cells.

Example 10

Proof of the efficiency and practicability of use of gene therapy DNA vector VTvaf17-TGFB3 carrying the TGFB3 gene in order to increase the expression of TGFB3 protein in mammalian cells.

The change in the TGFB3 protein concentration in the conditioned medium of the cell lysate of HEKa primary human epidermal keratinocyte cell culture (ATCC PCS-200-01) was assessed after transfection of these cells with the DNA vector VTvaf17-TGFB3 carrying the human TGFB3 gene. Cells were grown as described in Example 6.

The 6th generation SuperFect Transfection Reagent (Qiagen, Germany) was used for transfection. The aqueous dendrimer solution without DNA vector (A) and DNA vector VTvaf17 devoid of cDNA of TGFB3 gene (B) were used as a reference, and DNA vectorVTvaf17-TGFB3 carrying the human TGFB3 gene (C) was used as the transfected agent. Preparation of the DNA dendrimer complex and transfection of HEKa cells were performed according to the procedure described in Example 9.

After transfection, 0.1 ml of 1N HCl were added to 0.5 ml of the culture broth, mixed thoroughly, and incubated for 10 minutes at room temperature. Then, the mixture was neutralised by adding 0.1 ml of 1.2M NaOH/0.5M HEPES (pH 7-7.6) and stirred thoroughly. Supernatant was collected and used to assay the therapeutic protein. The TGFB3 protein was assayed by enzyme-linked immunosorbent assay (ELISA) using the Human TGF-β3 (Transforming Growth Factor Beta 3) ELISA Kit (Elabscience Cat. E-EL-H2339, USA) according to the manufacturer's method with optical density detection using ChemWell Automated EIA and Chemistry Analyser (Awareness Technology Inc., USA).

To measure the numerical value of concentration, the calibration curve constructed using the reference samples from the kit with known concentrations of TGFB3 protein was used. The sensitivity was at least 9.38 µg/ml, measurement range—from 15.63 µg/ml to 1000 µg/ml. R-3.0.2 was used for the statistical treatment of the results and data visualization (www.r-project.org/). Diagrams resulting from the assay are shown in FIG. 7.

FIG. 7 shows that the transfection of primary human uterine endometrial cells with gene therapy DNA vector VTvaf17-TGFB3 results in increased TGFB3 protein concentration compared to reference samples, which confirms the ability of the vector to penetrate eukaryotic cells and express the TGFB3 gene at the protein level. The presented results also confirm the practicability of use of gene therapy DNA vector VTvaf17-TGFB3 in order to increase the expression level of TGFB3 gene in eukaryotic cells.

Example 11

Proof of the efficiency and practicability of use of gene therapy DNA vector VTvaf17-TIMP2 carrying the TIMP2 gene in order to increase the expression of TIMP2 protein in mammalian cells.

Changes in the TIMP2 protein concentration in the lysate of Hs27 human foreskin fibroblast cell line (ATCC CRL-1634) were assessed after transfection of these cells with gene therapy DNA vector VTvaf17-TIMP2 carrying the human TIMP2 gene. Cells were cultured as described in Example 7.

The 6th generation SuperFect Transfection Reagent (Qiagen, Germany) was used for transfection. The aqueous dendrimer solution without DNA vector (A) and DNA vector VTvaf17 devoid of cDNA of TIMP2 gene (B) were used as a reference, and DNA vectorVTvaf17-TIMP2 carrying the human TIMP2 gene was used as the transfected agent. Preparation of the DNA dendrimer complex and transfection of Hs27 cells were performed according to the procedure described in Example 9.

After transfection, 0.1 ml of 1N HCl were added to 0.5 ml of the culture broth, mixed thoroughly, and incubated for 10 minutes at room temperature. Then, the mixture was neutralised by adding 0.1 ml of 1.2M NaOH/0.5M HEPES (pH 7-7.6) and stirred thoroughly. Supernatant was collected and used to assay the therapeutic protein. The TIMP2 protein was assayed by enzyme-linked immunosorbent assay (ELISA) using the Human TIMP2 ELISA Kit (Sandwich ELISA) (LifeSpan Bio Cat. LS-F196, USA) according to the manufacturer's method with optical density detection using ChemWell Automated EIA and Chemistry Analyser (Awareness Technology Inc., USA).

To measure the numerical value of concentration, the calibration curve constructed using the reference samples from the kit with known concentrations of TIMP2 protein was used. The sensitivity was at least 9.6 µg/ml, measurement range—from 9.6 µg/ml to 2333 µg/ml. R-3.0.2 was used for the statistical treatment of the results and data visualization (www.r-project.org/). Diagrams resulting from the assay are shown in FIG. 8.

FIG. 8 shows that the transfection of Hs27 human foreskin fibroblast cell line with gene therapy DNA vector VTvaf17-TIMP2 results in increased TIMP2 protein concentration compared to reference samples, which confirms the ability of the vector to penetrate eukaryotic cells and express the TIMP2 gene at the protein level. The presented results also confirm the practicability of use of gene therapy DNA vector VTvaf17-TIMP2 in order to increase the expression level of TIMP2 gene in eukaryotic cells.

Example 12

Proof of the efficiency and practicability of use of gene therapy DNA vector VTvaf17-FMOD carrying the FMOD gene in order to increase the expression of FMOD protein in mammalian cells.

Changes in the FMOD protein concentration in the lysate of HMEC-1 human dermal microvascular endothelial cell line (ATCC CRL-3243) were assessed after transfection of these cells with gene therapy DNA vector VTvaf17-FMOD carrying the human FMOD gene. Cells were cultured as described in Example 7.

The 6th generation SuperFect Transfection Reagent (Qiagen, Germany) was used for transfection. The aqueous dendrimer solution without DNA vector (A) and DNA vector VTvaf17 devoid of cDNA of FMOD gene (B) were used as a reference, and DNA vector VTvaf17-FMOD carrying the human FMOD gene was used as the transfected agent. Preparation of the DNA dendrimer complex and transfection of HMEC-1 cells were performed according to the procedure described in Example 9.

After transfection, 0.1 ml of 1N HCl were added to 0.5 ml of the culture broth, mixed thoroughly, and incubated for 10 minutes at room temperature. Then, the mixture was neutralised by adding 0.1 ml of 1.2M NaOH/0.5M HEPES (pH 7-7.6) and stirred thoroughly. Supernatant was collected and used to assay the therapeutic protein.

The FMOD protein was assayed by enzyme-linked immunosorbent assay (ELISA) using the Human FMOD/Fibromodulin ELISA Kit (Sandwich ELISA) (LifeSpan Bio Cat. LS-F4730, USA) according to the manufacturer's method with optical density detection using ChemWell Automated EIA and Chemistry Analyser (Awareness Technology Inc., USA).

To measure the numerical value of concentration, the calibration curve constructed using the reference samples from the kit with known concentrations of FMOD protein was used. The sensitivity was at least 14.3 µg/ml, measurement range—from 31.25 µg/ml to 2000 µg/ml. R-3.0.2 was used for the statistical treatment of the results and data visualization (www.r-project.org/). Diagrams resulting from the assay are shown in FIG. 9.

FIG. 9 shows that the transfection of HMEC-1 human dermal microvascular endothelial cell line with gene therapy DNA vector VTvaf17-FMOD results in increased FMOD protein concentration compared to reference samples, which confirms the ability of the vector to penetrate eukaryotic cells and express the FMOD gene at the protein level. The presented results also confirm the practicability of use of gene therapy DNA vector VTvaf17-FMOD in order to increase the expression level of FMOD gene in eukaryotic cells.

Example 13

Proof of the efficiency and practicability of use of gene therapy DNA vector VTvaf17-FMOD carrying the FMOD gene in order to increase the expression of FMOD protein in human tissues.

To confirm the efficiency of gene therapy DNA vector VTvaf17-FMOD carrying the therapeutic gene, namely the FMOD gene, and practicability of its use, changes in FMOD protein concentration in human skin upon injection of gene therapy DNA vector VTvaf17-FMOD carrying the human FMOD gene were assessed.

To analyse changes in the FMOD protein concentration, gene therapy DNA vector VTvaf17-FMOD carrying the FMOD gene was injected into the forearm skin of three patients with concurrent injection of a placebo being gene therapy DNA vector VTvaf17 devoid of cDNA of FMOD gene.

Patient 1, woman, 59 y.o. (P1); Patient 2, woman, 56 y.o. (P2); Patient 3, man, 52 y.o. (P3). Polyethyleneimine Transfection reagent cGMP grade in-vivo-jetPEI (Polyplus Transfection, France) was used as a transport system. Gene therapy DNA vector VTvaf17-FMOD containing cDNA of FMOD gene and gene therapy DNA vector VTvaf17 used as a placebo not containing cDNA of FMOD gene were dissolved in sterile nuclease-free water. To obtain a gene construct, DNA-cGMP grade in-vivo-jetPEI complexes were prepared according to the manufacturer recommendations.

Gene therapy DNA vector VTvaf17 (placebo) and gene therapy DNA vector VTvaf17-FMOD carrying the FMOD gene were injected in the quantity of 1 mg for each genetic construct using the tunnel method with a 30G needle to the depth of 3 mm. The injectate volume of gene therapy DNA vector VTvaf17 (placebo) and gene therapy DNA vector VTvaf17-FMOD carrying the FMOD gene was 0.3 ml for each genetic construct. The points of injection of each genetic construct were located at 8 to 10 cm intervals at the forearm site.

The biopsy samples were taken on the 2nd day after the injection of the genetic constructs of gene therapy DNA vectors. The biopsy samples were taken from the patients' skin in the site of injection of gene therapy DNA vector VTvaf17-FMOD carrying the FMOD gene (I), gene therapy DNA vector VTvaf17 (placebo) (II), and from intact skin (III) using the skin biopsy device Epitheasy 3.5 (Medax SRL, Italy). The skin of patients in the biopsy site was preliminarily rinsed with sterile saline and anaesthetised with a lidocaine solution. The biopsy sample size was ca. 10 mm3, and the weight was approximately 11 mg. The sample was placed in a buffer solution containing 50 mM of Tris-HCl, pH 7.6, 100 mM of NaCl, 1 mM of EDTA, and 1 mM of phenylmethylsulfonyl fluoride, and homogenised to obtain a homogenised suspension. The suspension was then centrifuged for 10 minutes at 14,000 g. Supernatant was collected and used in order to assay the therapeutic protein by enzyme-linked immunosorbent assay (ELISA) using Human FMOD/Fibromodulin ELISA Kit (Sandwich ELISA) (LifeSpan Bio Cat. LS-F4730, USA) according to the manufacturer's method with optical density detection using ChemWell Automated EIA and Chemistry Analyser (Awareness Technology Inc., USA).

To measure the numerical value of concentration, the calibration curve constructed using the reference samples from the kit with known concentrations of FMOD protein was used. The sensitivity was at least 14.3 µg/ml, measurement range—from 31.25 µg/ml to 2000 µg/ml. R-3.0.2 was used for the statistical treatment of the results and data visualization (www.r-project.org/). Diagrams resulting from the assay are shown in FIG. 10.

FIG. 10 shows the increased FMOD protein concentration in the skin of all three patients in the injection site of gene therapy DNA vector VTvaf17-FMOD carrying the human FMOD therapeutic gene compared to the FMOD protein concentration in the injection site of gene therapy DNA vector VTvaf17 (placebo) devoid of the human FMOD gene, which indicates the efficiency of gene therapy DNA vector VTvaf17-FMOD and confirms the practicability of its use, in particular upon intracutaneous injection of gene therapy DNA vector in human tissues.

Example 14

Proof of the efficiency and practicability of use of gene therapy DNA vector VTvaf17-TIMP carrying the TIMP gene in order to increase the expression of TIMP protein in human tissues.

To confirm the efficiency of gene therapy DNA vector VTvaf17-TIMP carrying the TIMP therapeutic gene and practicability of its use, the change in the TIMP protein concentration in human muscle tissues upon injection of gene therapy DNA vector VTvaf17-TIMP carrying the therapeutic gene, namely the human TIMP gene, was assessed.

To analyse changes in the concentration of TIMP protein, gene therapy DNA vector VTvaf17-TIMP carrying the TIMP gene with transport molecule was injected into the gastrocnemius muscle of three patients with concurrent injection of a placebo being gene therapy DNA vector VTvaf17 devoid of cDNA of TIMP gene with transport molecule.

Patient 1, woman, 51 y.o. (P1); Patient 2, woman, 42 y.o. (P2); Patient 3, man, 62 y.o. (P3). Polyethyleneimine Transfection reagent cGMP grade in-vivo-jetPEI (Polyplus Transfection, France) was used as a transport system; sample preparation was carried out in accordance with the manufacturer's recommendations.

Gene therapy DNA vector VTvaf17 (placebo) and gene therapy DNA vector VTvaf17-TIMP carrying the TIMP gene were injected in the quantity of 1 mg for each genetic construct using the tunnel method with a 30G needle to the depth of around 10 mm. The injectate volume of gene therapy DNA vector VTvaf17 (placebo) and gene therapy DNA vector VTvaf17-TIMP carrying the TIMP gene was 0.3 ml for each genetic construct. The points of injection of each genetic construct were located medially at 8 to 10 cm intervals.

The biopsy samples were taken on the 2nd day after the injection of the genetic constructs of gene therapy DNA vectors. The biopsy samples were taken from the patients' muscle tissues in the site of injection of gene therapy DNA vector VTvaf17-TIMP carrying the TIMP gene (I), gene therapy DNA vector VTvaf17 (placebo) (II), and intact site of gastrocnemius muscle (III) using the skin biopsy device MAGNUM (BARD, USA). The skin of patients in the biopsy site was preliminarily rinsed with sterile saline and anaesthetised with a lidocaine solution. The biopsy sample size was ca. 20 mm3, and the weight was up to 22 mg. The sample was placed in a buffer solution containing 50 mM of Tris-HCl, pH 7.6, 100 mM of NaCl, 1 mM of EDTA, and 1 mM of phenylmethylsulfonyl fluoride, and homogenised to obtain a homogenised suspension. The suspension was then centrifuged for 10 minutes at 14,000 g. Supernatant was collected and used to assay the therapeutic protein.

The TIMP protein was assayed by enzyme-linked immunosorbent assay (ELISA) using the Human TIMP2 ELISA Kit (Sandwich ELISA) (LifeSpan Bio Cat. LS-F196, USA) according to the manufacturer's method with optical density detection using ChemWell Automated EIA and Chemistry Analyser (Awareness Technology Inc., USA).

To measure the numerical value of concentration, the calibration curve constructed using the reference samples from the kit with known concentrations of TIMP2 protein was used. The sensitivity was at least 9.6 µg/ml, measurement range—from 9.6 µg/ml to 2333 µg/ml. R-3.0.2 was used for the statistical treatment of the results and data visualization (www.r-project.org/). Diagrams resulting from the assay are shown in FIG. 11.

FIG. 11 shows the increased TIMP protein concentration in the gastrocnemius muscle of all three patients in the injection site of gene therapy DNA vector VTvaf17-TIMP carrying the therapeutic gene, namely human TIMP gene, compared to the TIMP protein concentration in the injection site of gene therapy DNA vector VTvaf17 (placebo) devoid of the human TIMP gene, which indicates the efficiency of gene therapy DNA vector VTvaf17-TIMP and confirms the practicability of its use, in particular upon intramuscular injection of gene therapy DNA vector in human tissues.

Example 15

Proof of the efficiency and practicability of use of gene therapy DNA vector VTvaf17-TGFB3 carrying the TGFB3 gene in order to increase the expression of TGFB3 protein in human tissues.

To confirm the efficiency of gene therapy DNA vector VTvaf17-TGFB3 carrying the therapeutic gene, namely the TGFB3 gene, and practicability of its use, changes in TGFB3 protein concentration in human skin upon injection of gene therapy DNA vector VTvaf17-TGFB3 carrying the human TGFB3 gene were assessed.

To analyse changes in the TGFB3 protein concentration, gene therapy DNA vector VTvaf17-TGFB3 carrying the TGFB3 gene was injected into the forearm skin of three patients with concurrent injection of a placebo being gene therapy DNA vector VTvaf17 devoid of cDNA of TGFB3 gene.

Patient 1, woman, 48 y.o. (P1); Patient 2, man, 49 y.o. (P2); Patient 3, man, 57 y.o. (P3). Polyethyleneimine Transfection reagent cGMP grade in-vivo-jetPEI (Polyplus Transfection, France) was used as a transport system. Gene therapy DNA vector VTvaf17-TGFB3 containing cDNA of TGFB3 gene and gene therapy DNA vector VTvaf17 used as a placebo not containing cDNA of TGFB3 gene were dissolved in sterile nuclease-free water. To obtain a gene construct, DNA-cGMP grade in-vivo-jetPEI complexes were prepared according to the manufacturer recommendations.

Gene therapy DNA vector VTvaf17 (placebo) and gene therapy DNA vector VTvaf17-TGFB3 carrying the TGFB3 gene were injected in the quantity of 1 mg for each genetic construct using the tunnel method with a 30G needle to the depth of 3 mm. The injectate volume of gene therapy DNA vector VTvaf17 (placebo) and gene therapy DNA vector VTvaf17-TGFB3 carrying the TGFB3 gene was 0.3 ml for each genetic construct. The points of injection of each genetic construct were located at 8 to 10 cm intervals at the forearm site.

The biopsy samples were taken on the 2nd day after the injection of the genetic constructs of gene therapy DNA vectors. The biopsy samples were taken from the patients' skin in the site of injection of gene therapy DNA vector VTvaf17-TGFB3 carrying the TGFB3 gene (I), gene therapy DNA vector VTvaf17 (placebo) (II), and from intact skin (III) using the skin biopsy device Epitheasy 3.5 (Medax SRL, Italy). The skin of patients in the biopsy site was preliminarily rinsed with sterile saline and anaesthetised with a lidocaine solution. The biopsy sample size was ca. 10 mm3, and the weight was approximately 11 mg. The sample was placed in a buffer solution containing 50 mM of Tris-HCl, pH 7.6, 100 mM of NaCl, 1 mM of EDTA, and 1 mM of phenylmethylsulfonyl fluoride, and homogenised to obtain a homogenised suspension. The suspension was then centrifuged for 10 minutes at 14,000 g. Supernatant was collected and used in order to assay the therapeutic protein by enzyme-linked immunosorbent assay (ELISA) using Human TGF-β3 (Transforming Growth Factor Beta 3) ELISA Kit (Elabscience Cat. E-EL-H2339, USA) according to the manufacturer's method with optical density detection using ChemWell Automated EIA and Chemistry Analyser (Awareness Technology Inc., USA).

To measure the numerical value of concentration, the calibration curve constructed using the reference samples from the kit with known concentrations of TGFB3 protein was used. The sensitivity was at least 9.38 μg/ml, measurement range—from 15.63 μg/ml to 1000 μg/ml. R-3.0.2 was used for the statistical treatment of the results and data visualization (www.r-project.org/). Diagrams resulting from the assay are shown in FIG. 12.

FIG. 12 shows the increased TGFB3 protein concentration in the skin of all three patients in the injection site of gene therapy DNA vector VTvaf17-TGFB3 carrying the human TGFB3 therapeutic gene compared to the TGFB3 protein concentration in the injection site of gene therapy DNA vector VTvaf17 (placebo) devoid of the human TGFB3 gene, which indicates the efficiency of gene therapy DNA vector VTvaf17-TGFB3 and confirms the practicability of its use, in particular upon intracutaneous injection of gene therapy DNA vector in human tissues.

Example 16

Proof of the efficiency of gene therapy DNA vector VTvaf17-TGFB3 carrying the TGFB3 gene and practicability of its use in order to increase the expression level of the TGFB3 protein in human tissues by injecting autologous fibroblasts transfected with gene therapy DNA vector VTvaf17-TGFB3.

To confirm the efficiency of gene therapy DNA vector VTvaf17-TGFB3 carrying the TGFB3 gene and practicability of its use, changes in the TGFB3 protein level in human skin upon injection of patient's skin with autologous fibroblast culture of the same patient transfected with gene therapy DNA vector VTvaf17-TGFB3 were assessed.

The appropriate autologous fibroblast culture transfected with the gene therapy DNA vector VTvaf17-TGFB3 carrying the TGFB3 gene was injected into the patient's forearm skin with concurrent injection of a placebo in the form of autologous fibroblast culture transfected with gene therapy DNA vector VTvaf17 not carrying the TGFB3 gene.

The human primary fibroblast culture was isolated from the patient skin biopsy specimens. Biopsy specimens of the skin from the area protected by ultraviolet, namely behind the ear or on the inner lateral side of the elbow, were taken using the skin biopsy device Epitheasy 3.5 (Medax SRL, Italy). The biopsy sample was ca. 10 mm and ca. 11 mg. The patient's skin was preliminarily rinsed with sterile saline and anaesthetised with a lidocaine solution. The primary cell culture was cultivated at 37° C. in the presence of 5% CO2, in the DMEM medium with 10% fetal bovine serum and 100 U/ml of ampicillin. The passage and change of culture medium was performed every 2 days. Total duration of culture growth did not exceed 25-30 days. Then an aliquot of $5 \times 10^4$ cells was taken from the cell culture. The patient's fibroblast culture was transfected with the gene therapy DNA vector VTvaf17-TGFB3 carrying the TGFB3 gene or placebo, i.e. VTvaf17 vector not carrying the TGFB3 therapeutic gene.

The transfection was carried out using a cationic polymer such as polyethyleneimine JETPEI (Polyplus transfection, France), according to the manufacturer's instructions. The cells were cultured for 72 hours and then injected into the patient. Injection of autologous fibroblast culture of the patient transfected with gene therapy DNA vector VTvaf17-TGFB3, and autologous fibroblast culture of the patient non-transfected with gene therapy DNA vector VTvaf17 as a placebo was performed in the forearm using the tunnel method with a 13 mm long 30G needle to the depth of approximately 3 mm. The concentration of the modified autologous fibroblasts in the introduced suspension was approximately 5 mln cells per 1 ml of the suspension, the dose of the injected cells did not exceed 15 mln. The points of injection of the autologous fibroblast culture were located at 8 to 10 cm intervals.

Biopsy samples were taken on the 4th day after the injection of autologous fibroblast culture transfected with the gene therapy DNA vector VTvaf17-TGFB3 carrying the therapeutic gene, namely TGFB3 gene, and placebo. Biopsy was taken from the patient's skin in the site of injection of autologous fibroblast culture transfected with gene therapy DNA vector VTvaf17-TGFB3 carrying the therapeutic gene, namely TGFB3 gene (C), autologous fibroblast culture transfected with gene therapy DNA vector VTvaf17 not carrying the TGFB3 therapeutic gene (placebo) (B), as well as from intact skin site (A) using the skin biopsy device Epitheasy 3.5 (Medax SRL, Italy). The skin of patients in the biopsy site was preliminarily rinsed with sterile saline and anaesthetised with a lidocaine solution. The biopsy sample size was ca. 10 mm3, and the weight was approximately 11 mg. The sample was placed in a buffer solution containing 50 mM of Tris-HCl, pH 7.6, 100 mM of NaCl, 1 mM of EDTA, and 1 mM of phenylmethylsulfonyl fluoride, and homogenised to obtain a homogenised suspension. The suspension was then centrifuged for 10 minutes at 14,000 g. Supernatant was collected and used to assay the therapeutic protein as described in Example 15.

Diagrams resulting from the assay are shown in FIG. 13.

FIG. 13 shows the increased concentration of TGFB3 protein in the area of the patient's skin in the injection site of autologous fibroblast culture transfected with the gene therapy DNA vector VTvaf17-TGFB3 carrying the TGFB3 gene compared to the TGFB3 protein concentration in the injection site of autologous fibroblast culture transfected with the gene therapy DNA vector VTvaf17 not carrying the TGFB3 gene (placebo), which indicates the efficiency of gene therapy DNA vector VTvaf17-TGFB3 and practicability of its use in order to increase the expression level of TGFB3 in human organs, in particular upon injection of autologous fibroblasts transfected with the gene therapy DNA vector VTvaf17-TGFB3 into the skin.

Example 17

Proof of the efficiency and practicability of combined use of gene therapy DNA vector VTvaf17-SKI carrying the SKI gene, gene therapy DNA vector VTvaf17-TGFB3 carrying the TGFB3 gene, gene therapy DNA vector VTvaf17-TIMP2 carrying the TIMP2 gene, gene therapy DNA vector VTvaf17-FMOD carrying the FMOD gene for the increase of expression level of SKI, TGFB3, TIMP2, and FMOD proteins in mammalian tissues.

The change in the SKI, TGFB3, TIMP2, and FMOD protein concentration in the site of preliminary surgically modelled flat wound scar of rat skin was assessed when a mixture of gene therapy vectors was injected into this site.

A scar was formed in Wistar rats under general anaesthesia by surgical excision of the skin on the dorsal surface with the formation of 2 cm in diameter round wound. The procedure was performed according to the description known from the literature (Li, P., et al.//J Pathol, 2011. 223(5): p. 659-71).

Polyethyleneimine Transfection reagent cGMP grade in-vivo-jetPEI (Polyplus Transfection, France) was used as a transport system. Equimolar mixture of gene therapy DNA vectors was dissolved in sterile nuclease-free water. To obtain a gene construct, DNA-cGMP grade in-vivo-jetPEI complexes were prepared according to the manufacturer recommendations. The injectate volume was 0.3 ml with a total quantity of DNA equal to 100 µg. The solution was injected by tunnel method with a 30G needle to the depth of 2-3 mm in the site of preliminary surgically modelled flat wound scar of the rat 48 hours after the scar formation.

The biopsy samples were taken on the 2nd day after the injection of the gene therapy DNA vectors. The biopsy sample was taken from the scar areas on the skin of animals in the injection site of a mixture of four gene therapy DNA vectors carrying the genes SKI, TGFB3, TIMP2, and FMOD (site 1), gene therapy DNA vector VTvaf17 (placebo) (site II), as well as from the similar model scar area, not subjected to any manipulations (site III), using the skin biopsy device Epitheasy 3.5 (Medax SRL). The biopsy sample site was preliminarily rinsed with sterile saline and anaesthetised with a lidocaine solution. The biopsy sample size was ca. 10 mm3, and the weight was approximately 11 mg. Each sample was placed in a buffer solution containing 50 mM of Tris-HCl, pH 7.6, 100 mM of NaCl, 1 mM of EDTA, and 1 mM of phenylmethylsulfonyl fluoride, and homogenised to obtain a homogenised suspension. The suspension was then centrifuged for 10 minutes at 14,000 g. Supernatant was collected and used to assay the therapeutic proteins as described in Example 9 (quantification of SKI protein), Example 10 (quantification of TGFB3 protein), Example 11 (quantification of TIMP2 protein), and Example 12 (quantification of FMOD protein). Diagrams resulting from the assay are shown in FIG. 12.

FIGS. 14A and 14B demonstrate that the concentration of SKI, TGFB3, TIMP2, and FMOD proteins was increased in the site of preliminary surgically modelled flat wound scar of rats (site 1) where a mixture of gene therapy DNA vector VTvaf17-SKI carrying the SKI therapeutic gene, gene therapy DNA vector VTvaf17-TGFB3 carrying the TGFB3 therapeutic gene, gene therapy DNA vector VTvaf17-TIMP2 carrying the TIMP2 therapeutic gene, gene therapy DNA vector VTvaf17-FMOD carrying the FMOD therapeutic gene were injected compared to site II (placebo site) and site III (intact site). The obtained results show the efficiency of combined use of gene therapy DNA vectors and practicability of use for the increase of the expression level of therapeutic proteins in mammalian tissues.

Example 18

Proof of the efficiency of gene therapy DNA vector VTvaf17-TIMP2 carrying the TIMP2 gene and practicability of its use in order to increase the expression level of TIMP2 protein in mammalian cells.

To confirm the efficiency of gene therapy DNA vector VTvaf17-TIMP2 carrying the TIMP2 gene, changes in mRNA accumulation of the TIMP2 therapeutic gene in bovine dermal fibroblast cells (ScienCell, Cat. #B2300) 48 hours after their transfection with gene therapy DNA vector VTvaf17-TIMP2 carrying the human TIMP2 gene were assessed.

Bovine dermal fibroblast cells BDF (ScienCell, Cat. #B2300) were grown in the FM-2 medium (ScienCell, Cat. #2331). Transfection with gene therapy DNA vector VTvaf17-TIMP2 carrying the human TIMP2 gene and DNA vector VTvaf17 not carrying the human TIMP2 gene (reference), RNA extraction, reverse transcription reaction, PCR amplification, and data analysis were performed as described in Example 7. Bull/cow actin gene (ACT) listed in the GenBank database under number AH001130.2 was used as a reference gene. Positive control included amplicons from PCR on matrices represented by plasmids in known concentrations containing cDNA sequences of TIMP2 and ACT genes. Negative control included deionised water. Real-time quantification of the PCR products, i.e. TIMP2 and ACT gene cDNAs obtained by amplification, was conducted using the Bio-Rad CFX Manager 2.1 software (Bio-Rad, USA).

Diagrams resulting from the assay are shown in FIG. 15.

FIG. 15 shows that the level of specific mRNA of human TIMP2 gene has grown massively as a result of transfection of bovine dermal fibroblast cells BDF with gene therapy DNA vector VTvaf17-TIMP2, which confirms the ability of the vector to penetrate eukaryotic cells and express the TIMP2 gene at the mRNA level. The presented results confirm the practicability of use of gene therapy DNA vector VTvaf17-TIMP2 in order to increase the expression level of TIMP2 gene in mammalian cells.

Example 19

*Escherichia coli* strain SCS110-AF/VTvaf17-SKI, or *Escherichia coli* strain SCS110-AF/VTvaf17-TGFB3, or *Escherichia coli* strain SCS110-AF/VTvaf17-TIMP2, or *Escherichia coli* strain SCS110-AF/VTvaf17-FMOD carrying gene therapy DNA vector, method of production thereof.

The construction of strain for the production of gene therapy DNA vector based on gene therapy DNA vector VTvaf17 carrying the therapeutic gene on an industrial scale selected from the group of the following genes: SKI, TGFB3, TIMP2, and FMOD, namely *Escherichia coli* strain SCS110-AF/VTvaf17-SKI, or *Escherichia coli* strain SCS110-AF/VTvaf17-TGFB3, or *Escherichia coli* strain SCS110-AF/VTvaf17-TIMP2, or *Escherichia coli* strain SCS110-AF/VTvaf17-FMOD carrying the gene therapy DNA vector VTvaf17-SKI, or VTvaf17-TGFB3, or VTvaf17-TIMP2, or VTvaf17-FMOD, respectively, for its production allowing for antibiotic-free selection involves making electrocompetent cells of *Escherichia coli* strain SCS110-AF and subjecting these cells to electroporation with gene therapy DNA vector VTvaf17-SKI, or DNA vector VTvaf17-TGFB3, or DNA vector VTvaf17-TIMP2, or DNA vector VTvaf17-FMOD. After that, the cells were poured into agar plates (Petri dishes) with a selective medium containing yeastrel, peptone, 6% sucrose, and 10 μg/ml of chloramphenicol. At the same time, production of *Escherichia coli* strain SCS110-AF for the production of gene therapy DNA vector VTvaf17 or gene therapy DNA vectors based on it allowing for antibiotic-free positive selection involves constructing a 64 bp linear DNA fragment that contains regulatory element RNA-IN of transposon Tn10 allowing for antibiotic-free positive selection, a 1422 bp levansucrase gene sacB, the product of which ensures selection within a sucrose-containing medium, a 763 bp chloramphenicol resistance gene catR required for the selection of strain clones in which homologous recombination occurs, and two homologous sequences, 329 bp and 233 bp, ensuring homologous recombination in the region of gene recA concurrent with gene inactivation, and then the *Escherichia coli* cells are transformed by electroporation, and clones surviving in a medium containing 10 μg/ml of chloramphenicol are selected.

The obtained strains for production were included in the collection of the National Biological Resource Centre—Russian National Collection of Industrial Microorganisms (NBRC RNCIM), RF and NCIMB Patent Deposit Service, UK under the following registration numbers:

*Escherichia coli* strain SCS110-AF/VTvaf17-SKI—registered at the Russian National Collection of Industrial Microorganisms (VKPM), accession number B-13198, located in Russia, 117545, Moscow, 1st Dorozhny proezd, 1, and described as "cellular organisms; Bacteria; Proteobacteria; Gammaproteobacteria; Enterobacterales; Enterobacteriaceae; *Escherichia; Escherichia coli*", also deposited at the INTERNATIONAL DEPOSITARY AUTHORITY of National Collections of Industrial, Food and Marine Bacteria (NCIMB), located at Ferguson Building, Craibstone Estate, Bucksburn, Aberdeen AB29 9YA, Scotland, as accession No. NCIMB 43083, deposited on Jun. 21, 2018, and described as "cellular organisms; Bacteria; Proteobacteria; Gammaproteobacteria; Enterobacterales; Enterobacteriaceae; *Escherichia; Escherichia coli*",

*Escherichia coli* strain SCS110-AF/VTvaf17-TGFB3—registered at the Russian National Collection of Industrial Microorganisms under number B-13197, INTERNATIONAL DEPOSITARY AUTHORITY No. NCIMB 43084,

*Escherichia coli* strain SCS110-AF/VTvaf17-TIMP2—registered at the Russian National Collection of Industrial Microorganisms under number B-13196, INTERNATIONAL DEPOSITARY AUTHORITY No. NCIMB 43085,

*Escherichia coli* strain SCS110-AF/VTvaf17-FMOD—registered at the Russian National Collection of Industrial Microorganisms under number B-13199, INTERNATIONAL DEPOSITARY AUTHORITY No. NCIMB 43082.

Example 20

The method for scaling up of the gene therapy DNA vector based on gene therapy DNA vector VTvaf17 carrying the therapeutic gene selected from the group of SKI, TGFB3, TIMP2, and FMOD genes to an industrial scale.

To confirm the producibility and constructability of gene therapy DNA vector VTvaf17-SKI (SEQ ID NO: 1), or VTvaf17-TGFB3 (SEQ ID NO: 2), or VTvaf17-TIMP2 (SEQ ID NO: 3), or VTvaf17-FMOD (SEQ ID NO: 4) on an industrial scale, large-scale fermentation of *Escherichia coli* strain SCS110-AF/VTvaf17-SKI, or *Escherichia coli* strain SCS110-AF/VTvaf17-TGFB3, or *Escherichia coli* strain SCS110-AF/VTvaf17-TIMP2, or *Escherichia coli* strain SCS110-AF/VTvaf17-FMOD each containing gene therapy DNA vector VTvaf17 carrying the therapeutic gene, namely SKI, or TGFB3, or TIMP2, or FMOD, was performed. Each *Escherichia coli* strain SCS110-AF/VTvaf17-SKI, or *Escherichia coli* strain SCS110-AF/VTvaf17-TGFB3, or *Escherichia coli* strain SCS110-AF/VTvaf17-TIMP2, or *Escherichia coli* strain SCS110-AF/VTvaf17-FMOD was produced based on *Escherichia coli* strain SCS110-AF (Cell and Gene Therapy LLC, United Kingdom) as described in Example 21 by electroporation of competent cells of this strain with the gene therapy DNA vector VTvaf17-SKI, or VTvaf17-TGFB3, or VTvaf17-TIMP2, or VTvaf17-FMOD carrying the therapeutic gene, namely SKI, or TGFB3, or TIMP2, or FMOD with further inoculation of transformed cells into agar plates (Petri dishes) with a selective medium containing yeastrel, peptone, and 6% sucrose, and selection of individual clones.

Fermentation of *Escherichia coli* SCS110-AF/VTvaf17-SKI carrying gene therapy DNA vector VTvaf17-SKI was performed in a 10l fermenter with subsequent extraction of gene therapy DNA vector VTvaf17-SKI.

For the fermentation of *Escherichia coli* strain SCS110-AF/VTvaf17-SKI, a medium was prepared containing (per 10l of volume): 100 g of tryptone and 50 g of yeastrel (Becton Dickinson, USA); then the medium was diluted with water to 8800 ml and autoclaved at 121° C. for 20 minutes, and then 1200 ml of 50% (w/v) sucrose was added. After that, the seed culture of *Escherichia coli* strain SCS110-AF/VTvaf17-SKI was inoculated into a culture flask in the volume of 100 ml. The culture was incubated in an incubator shaker for 16 hours at 30° C. The seed culture was transferred to the Techfors S bioreactor (Infors HT, Switzerland) and grown to a stationary phase. The process was controlled by measuring optical density of the culture at 600 nm. The cells were pelleted for 30 minutes at 5,000-10,000 g. Supernatant was removed, and the cell pellet was re-suspended in 10% (by volume) phosphate buffered saline. The cells were centrifuged again for 30 minutes at 5,000-10,000 g. Supernatant was removed, a solution of 20 mM TrisCl, 1 mM EDTA, 200 g/l sucrose, pH 8.0 was added to the cell pellet in the volume of 1000 ml, and the mixture was stirred thoroughly to a homogenised suspension. Then egg lysozyme solution was added to the final concentration of 100 μg/ml. The mixture was incubated for 20 minutes on ice while stirring gently. Then 2500 ml of 0.2M NaOH, 10 g/l sodium dodecyl sulphate (SDS) was added, the mixture was incubated for 10 minutes on ice while stirring gently, then 3500 ml of 3M sodium acetate, 2M acetic acid, pH 5-5.5 was added, and the mixture was incubated for 10 minutes on ice while stirring gently. The resulting sample was centrifuged for 20-30 minutes at 15,000 g or a greater value. The solution was decanted delicately, and residual precipitate was removed by passing through a coarse filter (filter paper). Then, RNase A (Sigma, USA) was added to the final concentration of 20 μg/ml, and the solution was incubated overnight for 16 hours at room temperature. The solution was then centrifuged for 20-30 minutes at 15,000 g and passed through a 0.45 μm membrane filter (Millipore, USA). Then, ultrafiltration was performed with a 100 kDa membrane (Millipore, USA) and the mixture was diluted to the initial volume with a buffer solution of 25 mM TrisCl, pH 7.0. This manipulation was performed three to four times. The solution was applied to the column with 250 ml of DEAE Sepharose HP (GE, USA), equilibrated with 25 mM TrisCl, pH 7.0. After the application of the sample, the column was washed with three volumes of the same solution and then gene therapy DNA vector VTvaf17-SKI was eluted using a linear gradient of 25 mM TrisCl, pH 7.0, to obtain a solution of 25 mM TrisCl, pH 7.0, 1M NaCl, five times the volume of the column. The elution process was controlled by measuring optical density of the run-off solution at 260 nm. Chromatographic fractions containing gene therapy DNA vector VTvaf17-SKI were joined together and subjected to gel filtration using Superdex 200 (GE, USA). The column was equilibrated with phosphate buffered saline. The elution process was controlled by measuring optical density of the run-off solution at 260 nm, and the fractions were analysed by agarose gel electrophoresis. The fractions containing gene therapy DNA vector VTvaf17-SKI were joined together and stored at −20° C. To assess the process reproducibility, the indicated processing operations were repeated five times. All processing operations for *Escherichia coli* strain SCS110-AF/VTvaf17-TGFB3, or *Escherichia coli* strain SCS110-AF/VTvaf17-TIMP2, or *Escherichia coli* strain SCS110-AF/VTvaf17-FMOD were performed in a similar way.

The process reproducibility and quantitative characteristics of final product yield confirm the producibility and constructability of gene therapy DNA vector VTvaf17-SKI, or VTvaf17-TGFB3, or VTvaf17-TIMP2, or VTvaf17-FMOD on an industrial scale.

Thus, the purpose set in this invention, namely the construction of the gene therapy DNA vectors in order to increase the expression level of SKI, TGFB3, TIMP2, and FMOD genes that combine the following properties:
- The effectiveness of increase of the expression of therapeutic genes in eukaryotic cells due to the obtained gene therapy vectors with a minimum length,
- Possibility of safe use in gene therapy of human beings and animals due to the absence of regulatory elements representing the nucleotide sequences of viral genomes and antibiotic resistance genes in the gene therapy DNA vector,
- Producibility and constructability in the strains on an industrial scale,
- as well as the purpose of the construction of strains carrying these gene therapy DNA vectors for the production of these gene therapy DNA vectors is achieved, which is supported by the following examples:
    - for I—Example 1, 2, 3, 4, 5; 6; 7; 8; 9; 10; 11; 12; 13; 14; 15; 16; 17; 18
    - for II—Example 1, 2, 3, 4
    - for III and Item IV—Example 19, 20.

INDUSTRIAL APPLICABILITY

All the examples listed above confirm the industrial applicability of the proposed gene therapy DNA vector based on gene therapy DNA vector VTvaf17 carrying the therapeutic gene selected from the group of SKI, TGFB3, TIMP2, and FMOD genes in order to increase the expression level of these therapeutic genes, method of its production and use, *Escherichia coli* strain SCS110-AF/VTvaf17-SKI, or *Escherichia coli* strain SCS110-AF/VTvaf17-TGFB3, or *Escherichia coli* strain SCS110-AF/VTvaf17-TIMP2, or *Escherichia coli* strain SCS110-AF/VTvaf17-FMOD carrying gene therapy DNA vector, and method of its production on an industrial scale.

List of Oligonucleotide Sequences:

SKI_F SEQ ID NO: 5
CAGGATCCGCGGGAGCGGCCGGGGAG

SKI_R SEQ ID NO: 6
TATAAGCTTACGGCTCCAGCTCCGCAG

SKI_SF SEQ ID NO: 7
TGGACACCAAGGAAGCCAAAG

SKI_SR SEQ ID NO: 8
GCTGTTCCTGCAGCTCCTTCAC

TGFB3_F SEQ ID NO: 9
GGATCCACCATGAAGATGCACTTGCAAAGG

TGFB3_R SEQ ID NO: 10
TATAAGCTTAGCTACATTTACAAGACTTCACCA

TGFB3_SF SEQ ID NO: 11
TGAGCACATTGCCAAACAGC

TGFB3_SR SEQ ID NO: 12
GAGGCAGATGCTTCAGGGTT

TIMP2_F SEQ ID NO: 13
CAGGATCCGGCCCCCGCCCGCCCAGC

TIMP2_R SEQ ID NO: 14
TATAAGCTTATGGGTCCTCGATGTCGAGA

TIMP2_SF SEQ ID NO: 15
GCAACAGGCGTTTTGCAATG

TIMP2_SR SEQ ID NO: 16
AGGGCACGATGAAGTCACAG

FMOD_F SEQ ID NO: 17
GGATCCACCATGCAGTGGACCTCCCTCCT

FMOD_R SEQ ID NO: 18
TATGAATTCTTAGATCTCGATGAGGCTGGCA

FMOD_SF SEQ ID NO: 19
CCTACACCTACGGCTCTCCA

FMOD_SR SEQ ID NO: 20
CATCCGGGTCAGGTTGTTGT

List of Abbreviations
- VTvaf17—Gene therapy vector devoid of sequences of viral genomes and antibiotic resistance markers (vector therapeutic virus-antibiotic-free)
- DNA—Deoxyribonucleic acid
- cDNA—Complementary deoxyribonucleic acid
- RNA—Ribonucleic acid
- mRNA—Messenger ribonucleic acid
- bp—base pair
- PCR—Polymerase chain reaction
- ml—millilitre, μl—microlitre
- mm3—cubic millimetre
- l—litre μg—microgram
mg—milligram
g—gram
μM—micromol
mM—millimol
min—minute
s—second rpm—rotations per minute
nm—nanometre
cm—centimetre
mW—milliwatt
RFU—Relative fluorescence unit
PBS—Phosphate buffered saline

What is claimed is:

1. A DNA vector comprising DNA vector VTvaf17-SKI that has the nucleotide sequence of SEQ ID NO: 1.

2. A method of producing a DNA vector, comprising cloning a coding region of SKI into gene therapy DNA vector VTvaf17 to produce DNA vector VTvaf17-SKI that has the nucleotide sequence of SEQ ID NO: 1.

3. A method for treatment of diseases with fibrosis of tissues, formation of scars, connective tissue damage, the method for acceleration of wound healing, re-epithelisation, for increasing the formation of granulation tissue, and for inhibition of scar formation of a patient, comprising:
treating the patient with DNA vector VTvaf17-SKI that has the nucleotide sequence of SEQ ID NO: 1.

4. An *Escherichia coli* strain comprising SCS110-AF/VTvaf17-SKI, deposited at the National Collections of Industrial, Food and Marine Bacteria (NCIMB) as accession number NCIMB 43083.

* * * * *